United States Patent
Gagnon et al.

(10) Patent No.: US 10,391,073 B2
(45) Date of Patent: Aug. 27, 2019

(54) SUBSTITUTED AROMATIC COMPOUNDS AND PHARMACEUTICAL COMPOSITIONS FOR TISSUE SELF-REPAIR AND REGENERATION

(71) Applicant: PROMETIC PHARMA SMT LIMITED, Comberton, Cambridge (GB)

(72) Inventors: Lyne Gagnon, Laval (CA); Pierre Laurin, Ville Mont-Royal (CA)

(73) Assignee: Prometic Pharma SMT Limited, Comberton, Cambridge (GB)

( * ) Notice: Subject to any disclaimer, the term of this patent is extended or adjusted under 35 U.S.C. 154(b) by 0 days.

(21) Appl. No.: 15/526,405

(22) PCT Filed: Nov. 12, 2015

(86) PCT No.: PCT/CA2015/000572
§ 371 (c)(1),
(2) Date: May 12, 2017

(87) PCT Pub. No.: WO2016/074068
PCT Pub. Date: May 19, 2016

(65) Prior Publication Data
US 2017/0312237 A1  Nov. 2, 2017

Related U.S. Application Data

(60) Provisional application No. 62/078,704, filed on Nov. 12, 2014.

(51) Int. Cl.
| | |
|---|---|
| *A61K 8/36* | (2006.01) |
| *A61K 8/365* | (2006.01) |
| *A61P 17/02* | (2006.01) |
| *A61P 19/08* | (2006.01) |
| *A61Q 19/08* | (2006.01) |
| *C07C 57/30* | (2006.01) |
| *C07C 57/32* | (2006.01) |
| *C07C 57/58* | (2006.01) |
| *C07C 59/52* | (2006.01) |
| *C07C 59/84* | (2006.01) |
| *A61K 31/192* | (2006.01) |

(52) U.S. Cl.
CPC .............. *A61K 31/192* (2013.01); *A61K 8/36* (2013.01); *A61K 8/365* (2013.01); *A61P 17/02* (2018.01); *A61P 19/08* (2018.01); *A61Q 19/08* (2013.01); *C07C 57/30* (2013.01); *C07C 57/32* (2013.01); *C07C 57/58* (2013.01); *C07C 59/52* (2013.01); *C07C 59/84* (2013.01)

(58) Field of Classification Search
CPC ...... A61K 31/192; A61K 8/365; A61Q 19/08; C07C 57/30; C07C 57/22; C07C 57/58; C07C 59/52; C07C 59/84; A61P 17/02; A61P 19/08
See application file for complete search history.

(56) References Cited

FOREIGN PATENT DOCUMENTS

| WO | WO 2010127440 | * 11/2010 |
|---|---|---|
| WO | 2014/138906 A1 | 9/2014 |
| WO | 2014/138907 A1 | 9/2014 |

OTHER PUBLICATIONS

Eto et al. (Laboratory Investigation (2012) 92, 214-223).*

(Continued)

*Primary Examiner* — Shirley V Gembeh
(74) *Attorney, Agent, or Firm* — Pepper Hamilton LLP

(57) ABSTRACT

Described herein are compounds of Formula I, or pharmaceutically acceptable salts thereof, or combinations thereof, as well as uses thereof. Such uses include promoting tissue self-repair or tissue regeneration of an organ, stimulating the generation of tissue growth, modulating (e.g. increasing) the level of a tissue-repair marker, treating physical injury in an organ, tissue, or cell, promoting wound healing as well as anti-aging applications. Corresponding compositions, methods and uses are also described. Formula I wherein A is $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4; $R_1$ is H, F of OH; $R_2$ is H, F, OH, $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4; $R_3$ is H, F, OH, or $CH_2Ph$; $R_4$ is H, F or OH; Q is 1) $(CH_2)_mC(O)OH$ wherein m is 1 or 2 2) $CH(CH_3)C(O)OH$, 3) $C(CH_3)_2C(O)OH$, 4) $CH(F)-C(O)OH$, 5) $CF_2-C(O)OH$ or 6) $C(O)-C(O)OH$.

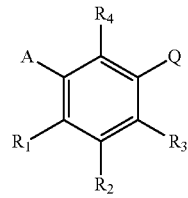

Formula I

19 Claims, 4 Drawing Sheets

(56) References Cited

OTHER PUBLICATIONS

Monfort et al (J. of Cosmtic, Dermatological Sciences and Agriculture (2012), 2, 93-107).*
Sugimuru et al. (Renal Failure, 23(3&4), 597-603 (2001)).*
International Search Report and Written Opinion for corresponding Application No. PCT/CA2015/000572 dated Feb. 24, 2016).

* cited by examiner

SUBSTITUTED AROMATIC COMPOUNDS AND PHARMACEUTICAL COMPOSITIONS FOR TISSUE SELF-REPAIR AND REGENERATION

This application is a national stage application under 35 U.S.C. § 371 of PCT Application No. PCT/CA2015/000572, filed Nov. 12, 2015, which claims the priority benefit of U.S. Provisional Patent Application Ser. No. 62/078,704, filed Nov. 12, 2014.

FIELD OF INVENTION

The present invention relates to the field of medicine. Particular aspects of the invention relates to compounds, pharmaceutical compositions and uses thereof for the tissue self-repair and/or the tissue regeneration of an injured organ, for stimulating the generation of tissue growth, and/or for modulating the expression of tissue self-repair markers and/or tissue regeneration markers such as metalloproteinases and growth factors.

BACKGROUND OF INVENTION

Tissue regeneration involves known markers such as metalloproteinases and growth factors, including without limitation HGF (hepatocyte growth factor), LOX (lysyl oxidase), MMP1, MMP2, MMP9, MMP13, PLAT (tPA), PLAU (uPA), Serpin A1 (AAT), Serpin E1 (PAI-1), TIMP3, ILK (integrin-linked kinase).

The impact of HGF in tissue repair and regeneration is well described in the scientific review: *The discovery of Hepatocyte Growth factor (HGF) and its significance for cell biology, life sciences and clinical medicine* from Nakamura and Mizuno, Proc. Jpn. Acad. Ser B86 (2010). This review article describes the role of HGF in tissue regeneration in liver, kidney, heart, and lung. Also, HGF is required for self-repair after injuries of skin, stomach, intestine, muscle and cartilage and is also involved in organ development (organogenesis including mitogenesis, motogenesis and morphogenesis). HGF is also implicated in the regeneration of injured tissue by its modulation of regeneration enzyme (metalloproteinases) and also by inhibiting apoptosis. Furthermore, recent reports suggest that HGF has an anti-inflammatory action and attenuated cellular senescence. Thus, HGF gene therapy or compound increasing HGF expression and secretion might be an anti-aging therapy in cardiovascular diseases (Nakagami, Morishita, 2009). HGF is also known to accelerate would healing (Li et al., *BioMed Research International*, Volume 2013 (2013), Article ID 470418.

Regeneration enzymes (including metalloproteinases) are also very important in repair and regeneration of injured organs.

A recent publication (abstract presented at Plastic surgery meeting 2014 by Radtke et al. entitled *Single treatment With Alpha-1 antitrypsin Enhances Nerve Regeneration After Peripheral Nerve Injury*) has demonstrated that AAT improves peripheral nerve regeneration. The application of AAT into an acute axotomy model led to the significantly improved axonal regeneration and re-myelination than compared control animals. Moreover, not only histological, but also functional improvement was observed following direct injection of AAT after acute peripheral nerve lesion. Their results indicate that AAT delivered into injured peripheral nerve participate in neural repair.

Cutaneous aging is a complex phenomenon responsible for progressive changes of the skin. Aging of the skin results from two processes: (1) an intrinsic process, corresponding to chronological aging, and (2) an extrinsic process resulting mainly from the deleterious effect of exposure environmental stresses. Genetic, UV exposure, climatic factors (harshness/wind/cold/warm), pollution (chemical, free radicals, contaminant, nitrogen oxide, metals), alcohol consumption or smoking are factors involved in cutaneous aging.

Exposure to irritants compromises the barrier function of the stratum corneum and decreases its ability to protect the skin against environmental stresses (e.g., ultraviolet irradiation, infections agents, etc.). Repeated and prolonged exposition to environmental irritants results in denatured skin proteins, disorganization of the lipid lamellae layers, removal of the protective intercellular lipids, loss of natural moisturizing factors and decreased cohesion between cells. These damages are also responsible for the loss of function of the enzymes responsible for desquamation of corneocytes. There is accentuation of these problems with exposure to pollution, cold, sun, wind, low humidity or chemical agents. An irritant is any agent that is capable of producing cell damage if there exposure for sufficient time and in sufficient concentrations. The severity of the damage is dependent of the type and intensity of exposure to these irritating factors. There are also endogenous factors that make one susceptible to damaged skin by external factors. These factors include having active skin disease such as eczema, inherited dry skin conditions, a previous history of skin disease, sensitive skin and/or older age.

Novel compounds and medicaments are needed to stimulate the tissue self-repair and the tissue regeneration in injured organ.

BRIEF SUMMARY OF THE INVENTION

General aspects of the invention relate to the pharmaceutical use of compounds according to Formula I as defined herein and pharmaceutically acceptable salts thereof.

Particular aspects of the invention relates to the use of compounds and compositions for the tissue self-repair and/or the tissue regeneration of an injured organ, and/or for modulating the expression of tissue self-repair markers and/or tissue regeneration markers such as metalloproteinases and growth factors, including without limitation HGF, LOX (Lysyl oxidase), MMP1, MMP2, MMP9, MMP13, PLAT (tPA), PLAU (uPA), Serpin A1 (AAT), Serpin E1 (PAI-1), TIMP3, and ILK (integrin-linked kinase).

A method for tissue self-repair or tissue regeneration of an organ in a subject in need thereof, comprising the step of administering to a subject in need thereof a compound represented by Formula I or a pharmaceutically acceptable salt thereof:

According to another aspect, the invention relates to a method for tissue self-repair or tissue regeneration of an organ in a subject in need thereof, comprising administering a compound represented by Formula I or a pharmaceutically acceptable salt thereof as defined herein to said subject. In an embodiment, the invention relates to a method for tissue self-repair of an organ in a subject in need thereof, comprising administering a compound represented by Formula I or a pharmaceutically acceptable salt thereof as defined herein to said subject. In an embodiment, the invention relates to a method for tissue remodelling of an organ in a subject in need thereof, comprising administering a compound represented by Formula I or a pharmaceutically acceptable salt thereof as defined herein to said subject. In an embodiment, the invention relates to a method for tissue regeneration of an organ in a subject in need thereof, comprising administering a compound represented by Formula I or a pharmaceutically acceptable salt thereof as defined herein to said subject.

According to another aspect, the invention relates to a method for stimulating the generation of tissue growth, with a compound represented by Formula I or a pharmaceutically acceptable salt thereof as defined herein.

According to another aspect, the invention relates to a method for stimulating the expression of tissue self-repair markers and/or tissue regeneration markers, with a compound represented by Formula I or a pharmaceutically acceptable salt thereof as defined herein. More particularly, said markers includes without limitation metalloproteinases, growth factors, hepatocyte growth factor (HGF), LOX (Lysyl oxidase), MMP1, MMP2, MMP9, MMP13, PLAT (tPA), PLAU (uPA), Serpin A1 (AAT), Serpin E1 (PAI-1), TIMP3, and ILK (integrin-linked kinase).

According to another aspect, the invention relates to a method for increasing HGF level in an organ, comprising the step of administering to said organ, a compound represented by Formula I or a pharmaceutically acceptable salt thereof as defined herein. The organ includes without limitation kidney, heart, liver, lung, skin, stomach, intestine, muscle and cartilage.

According to another aspect, the invention relates to a method for increasing AAT level in an organ, comprising the step of administering to said organ, a compound represented by Formula I or a pharmaceutically acceptable salt thereof as defined herein.

Further aspects of the invention will be apparent to a person skilled in the art from the following description, claims, and generalizations herein.

DETAILED DESCRIPTION OF THE INVENTION

Figure 1:
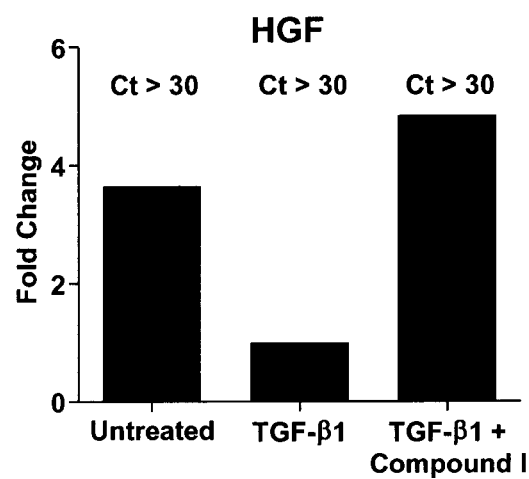
FIG. 1 is an illustration of the effect of Compound I on the increase of mRNA expression of Hepatocyte Growth Factor (HGF), a growth factor involved in tissue self-repair and regeneration.

The present discloses compounds of Formula I, pharmaceutically acceptable salts thereof, compositions comprising same and uses thereof. Various embodiments of the present invention include:
Compounds of the Invention According to one aspect, the invention concerns pharmaceutical uses of compounds represented by Formula I, or pharmaceutically acceptable salts thereof:

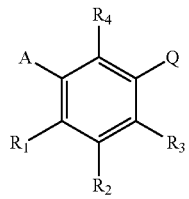

Formula I wherein
A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4; or is $C_5$ alkyl, $C_5$ alkenyl, C(O)—$(CH_2)_n$—$CH_3$ or CH(OH)—$(CH_2)_n$—$CH_3$ wherein n is 3; or is $C_6$ alkyl, $C_6$ alkenyl, C(O)—$(CH_2)_n$—$CH_3$ or CH(OH)—$(CH_2)_n$—$CH_3$ wherein n is 4;
$R_1$ is H, F or OH; or is H or OH;
$R_2$ is H, F, OH, $C_5$ alkyl, $C_6$ alkyl, CO alkenyl, $C_6$ alkenyl, C(O)—$(CH_2)_n$—$CH_3$ or CH(OH)—$(CH_2)_n$—$CH_3$ wherein n is 3 or 4; or is $C_5$ alkyl, $C_5$ alkenyl, C(O)—$(CH_2)_n$—$CH_3$ or CH(OH)—$(CH_2)_n$—$CH_3$ wherein n is 3; or is $C_6$ alkyl, $C_6$ alkenyl, C(O)—$(CH_2)_n$—$CH_3$ or CH(OH)—$(CH_2)_n$—$CH_3$ wherein n is 4
$R_3$ is H, F, OH or $CH_2Ph$; or is H, F or OH; or is H or OH;
$R_4$ is H, F or OH; or is H or OH;
Q is
1) $(CH_2)_mC(O)OH$ wherein m is 1 or 2,
2) $CH(CH_3)C(O)OH$,
3) $C(CH_3)_2C(O)OH$,
4) CH(F)—C(O)OH,
5) $CF_2$—C(O)OH, or
6) C(O)—C(O)OH.

According to a particular embodiment, A is $C_5$ alkyl or $C_6$ alkyl. Preferably, $C_5$ alkyl is a straight chain $C_5$ alkyl.

According to a particular embodiment, $R_1$ is H or OH.

According to a particular embodiment, $R_2$ is H, F, OH, $C_5$ alkyl or $C_6$ alkyl.

According to a particular embodiment, $R_3$ is H or OH.

According to a particular embodiment, $R_4$ is H or OH.

According to a particular embodiment, Q is:
1) $(CH2)_mC(O)OH$ wherein m is 1 or 2,
2) CH(F)—C(O)OH,
3) CF2—C(O)OH, or
4) C(O)—C(O)OH.

According to a particular embodiment, Q is $(CH_2)_mC(O)OH$ where m is 1 or 2.

According to another embodiment, the compound is of Formula I, wherein A is $C_5$ alkyl or $C_6$ alkyl; $R_1$ is H, F or OH; $R_2$ is H, F, OH, $C_5$ alkyl or $C_6$ alkyl; $R_3$ is H, OH or $CH_2Ph$; $R_4$ is H, F or OH; and Q is $(CH_2)_mC(O)OH$ where m is 1 or 2.

According to another embodiment, the compound is of Formula I; wherein A is $C_5$ alkyl; $R_1$ is H; $R_2$ is H or $C_5$ alkyl; $R_3$ is H; $R_4$ is H; and Q is $(CH_2)_mC(O)OH$ where m is 1.

As used herein, the term "alkyl" is intended to include a straight chain saturated aliphatic hydrocarbon group having the specified number of carbon atoms in a linear arrangement, and a branched chain saturated aliphatic hydrocarbon group having the specified number of carbon atoms in a non-linear arrangement, or a cyclic chain saturated aliphatic hydrocarbon group having the specified number of carbon atoms in a cyclic arrangement.

As used herein, the term, "alkenyl" is intended to mean unsaturated straight chain hydrocarbon groups having the specified number of carbon atoms therein, and in which at least two of the carbon atoms are bonded to each other by a double bond, and having either E or Z regiochemistry and combinations thereof.

Examples of compounds of Formula I include, but are not limited to, Compounds I to XXXIII and acid form thereof listed in Table 1 hereinbelow.

TABLE 1

Representative compounds of Formula I and acid form thereof

| Compound | Sodium Salt | Acid Form |
|---|---|---|
| I | | |
| II | | |
| III | | |
| IV | | |
| V | | |
| VI | | |
| VII | | |
| VIII | | |
| IX | | |
| X | | |
| XI | | |

TABLE 1-continued

Representative compounds of Formula I and acid form thereof

| Compound | Sodium Salt | Acid Form |
|---|---|---|
| XII | 3-pentyl-4-fluorophenylacetate sodium salt | 3-pentyl-4-fluorophenylacetic acid |
| XIII | sodium 2-(3-pentylphenyl)-2-fluoroacetate | 2-(3-pentylphenyl)-2-fluoroacetic acid |
| XIV | sodium 3,5-dipentylphenylacetate | 3,5-dipentylphenylacetic acid |
| XV | sodium 3,5-dihexylphenylacetate | 3,5-dihexylphenylacetic acid |
| XVI | sodium 3,5-dipentyl-2-hydroxyphenylacetate | 3,5-dipentyl-2-hydroxyphenylacetic acid |
| XVII | sodium 3,5-dihexyl-2-hydroxyphenylacetate | 3,5-dihexyl-2-hydroxyphenylacetic acid |
| XVIII | sodium 3,5-dipentyl-4-hydroxyphenylacetate | 3,5-dipentyl-4-hydroxyphenylacetic acid |
| XIX | sodium 3,5-dihexyl-4-hydroxyphenylacetate | 3,5-dihexyl-4-hydroxyphenylacetic acid |

TABLE 1-continued
Representative compounds of Formula I and acid form thereof
| Compound | Sodium Salt | Acid Form |
|---|---|---|
| XX | 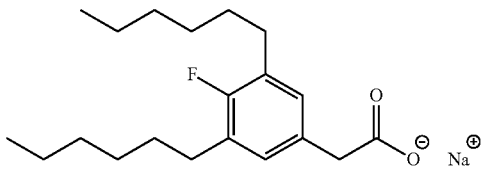 [SMILES: CCCCCCc1cc(CC(=O)[O-])cc(CCCCCC)c1F ; [Na+]] | 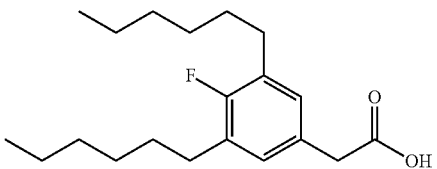 [SMILES: CCCCCCc1cc(CC(=O)O)cc(CCCCCC)c1F] |
| XXI | 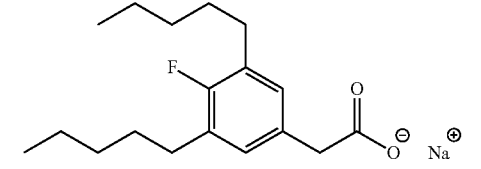 [SMILES: CCCCCc1cc(CC(=O)[O-])cc(CCCCC)c1F ; [Na+]] | 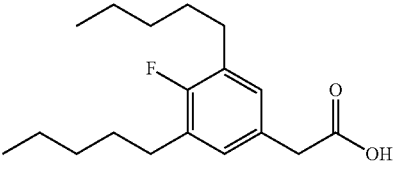 [SMILES: CCCCCc1cc(CC(=O)O)cc(CCCCC)c1F] |
| XXII | 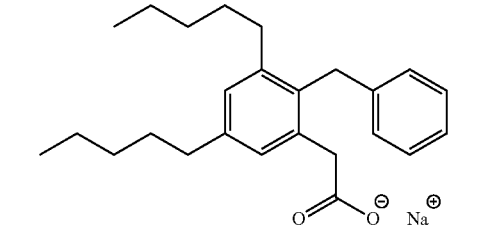 [SMILES: CCCCCc1cc(CCCCC)c(Cc2ccccc2)c(CC(=O)[O-])c1 ; [Na+]] | 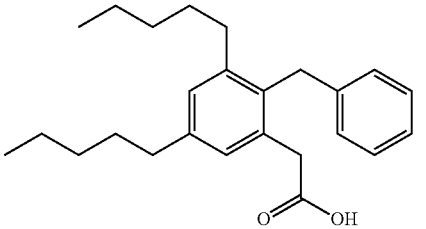 [SMILES: CCCCCc1cc(CCCCC)c(Cc2ccccc2)c(CC(=O)O)c1] |
| XXIII | 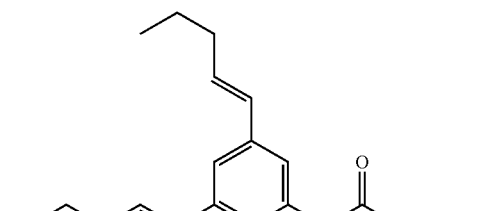 | 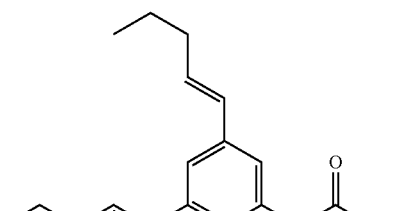 |
| XXIV | 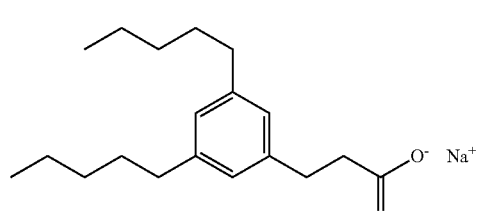 | 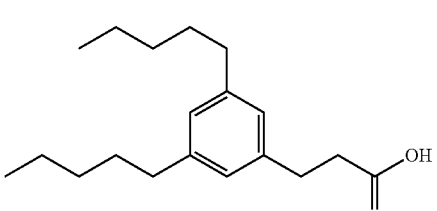 |
| XXV | 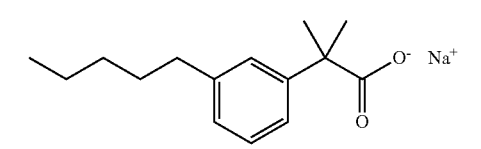 [SMILES: CCCCCc1cccc(C(C)(C)C(=O)[O-])c1 ; [Na+]] | 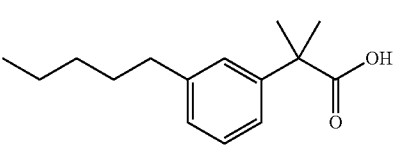 [SMILES: CCCCCc1cccc(C(C)(C)C(=O)O)c1] |
| XXVI | 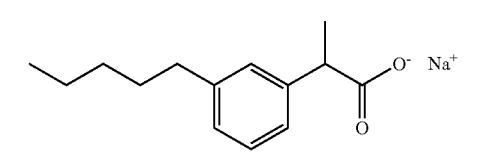 [SMILES: CCCCCc1cccc(C(C)C(=O)[O-])c1 ; [Na+]] | 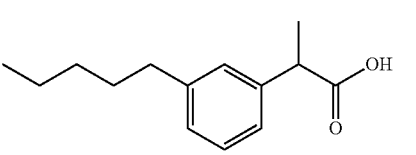 [SMILES: CCCCCc1cccc(C(C)C(=O)O)c1] |
| XXVII | 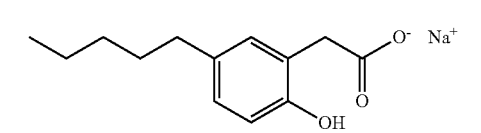 [SMILES: [Na+] ; CCCCCc1ccc(O)c(CC(=O)[O-])c1] | 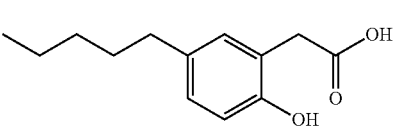 [SMILES: CCCCCc1ccc(O)c(CC(=O)O)c1] |

TABLE 1-continued

Representative compounds of Formula I and acid form thereof

| Compound | Sodium Salt | Acid Form |
|---|---|---|
| XXVIII | | |
| XXIX | | |
| XXX | | |
| XXXI | | |
| XXXII | | |
| XXXIII | | |

Salts

As used herein, the term "pharmaceutically acceptable salt" is intended to mean base addition salts. Example of pharmaceutically acceptable salts are also described, for example, in Berge et al., "Pharmaceutical Salts", J. Pharm. Sci. 66, 1-19 (1977). Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

The pharmaceutically acceptable salt of the compounds of Formula I may be selected from the group consisting of base addition salts of sodium, potassium, calcium, magnesium, lithium, ammonium, manganese, zinc, iron, or copper. In preferred embodiments, the pharmaceutically acceptable salt of the compounds according to the invention may be the sodium, potassium, calcium, magnesium or lithium salt. More preferably the pharmaceutically acceptable salt is sodium.

The compounds of Formula I disclosed herein may be in any form, including any acid, salt or other ionic and non-ionic forms. For example, if a compound is shown as an acid herein, the salt forms of the compound are also included. Likewise, if a compound is shown as a salt and the acid forms are also included.

Prodrugs

In certain embodiments, the compounds of Formula I disclosed herein, wherein said compounds are present in the free carboxylic acid form, may also include all pharmaceutically acceptable salts, isosteric equivalents such as tetrazole and prodrug forms thereof. Examples of the latter include the pharmaceutically acceptable esters or amides obtained upon reaction of alcohols or amines, including amino acids, with the free acids defined by Formula I.

Chirality

The compounds of Formula I disclosed herein, their pharmaceutically acceptable salts, or prodrugs thereof, may contain one or more asymmetric centers, chiral axes and chiral planes and may thus give rise to enantiomers, diastereomers, and other stereoisomeric forms and may be defined in terms of absolute stereochemistry, such as (R)- or (S)-. The present invention is intended to include all such possible isomers, as well as, their racemic and optically pure forms. Optically active (+) and (−), (R)- and (S)-, isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of Formula I or pharmaceutically acceptable salts thereof disclosed herein may exist in Zwitterionic form and the present invention includes the use of Zwitterionic forms of these compounds and mixtures thereof.

Hydrates

In addition, the compounds of Formula I or pharmaceutically acceptable salts thereof disclosed herein may also exist in hydrated and anhydrous forms. The present invention includes the use of hydrates of any of the compounds of Formula I or pharmaceutically acceptable salts thereof described herein, which may exist as a monohydrate or in the form of a polyhydrate.

Methods of Preparation

In general, all compounds of Formula I or pharmaceutically acceptable salts thereof disclosed herein may be prepared by any conventional methods, using readily available and/or conventionally preparable starting materials, reagents and conventional synthesis procedures. Of particular interest is the work of Hundertmark, T.; Littke, A. F.; Buchwald, S. L.; Fu, G. C. Org. Lett. 12, 1729-1731 (2000).

The exemplification section hereinafter provides general schemes and specific, but non limitative, examples for the synthesis of Compounds I-XXXIII.

Pharmaceutical Uses

The Compounds of Formula I or pharmaceutically acceptable salts thereof (or a composition comprising same) disclosed herein are useful: in the tissue self-repair and/or the tissue regeneration of an injured organ, tissue or cell, in stimulating the generation of new cells in an in vitro cell culture, and/or in modulating the expression of tissue self-repair markers and/or tissue regeneration markers such as metalloproteinases and growth factors. According to an embodiment, the Compounds of Formula I or pharmaceutically acceptable salts thereof disclosed herein are useful for an anti-aging treatment. In an embodiment, the treatment preferably comprises the administration of a Compound of Formula I or pharmaceutically acceptable salts thereof disclosed herein or a combination thereof, or a pharmaceutical composition comprising a therapeutically effective amount one or more of the compounds of Formula I or pharmaceutically acceptable salts thereof disclosed herein. The expressions "tissue self-repair" and "tissue regeneration" used herein may also refer to processes involved in an anti-aging treatment. Representative Compounds according to Formula I disclosed herein have been found to stimulate the expression of known markers associated with anti-aging, tissue regeneration and tissue self-repair, and to stimulate the generation of new cells.

In an embodiment, the injured organ, tissue or cell is not an organ, tissue or cell injured by an inflammatory-related disease. In an embodiment, the injured organ, tissue or cell is not an organ, tissue or cell injured by a cancer.

In an embodiment, the organ, tissue or cell injury results from a physical injury (i.e. following an acute exposure to an external agent or stress that results in some form of damage/injury to the organ, tissue or cell), for example an organ, tissue or cell injured by a physical trauma/insult (e.g., cut, bite, shock, tear, puncture, perforation, burn (heat or chemical), freezing, radiations, electrocution, physical overexertion), or a surgery. Physical injury as used herein excludes organ, tissue or cell damages resulting from (i.e. in which the primary cause of the organ, tissue or cell damages is) an underlying disease, for example inflammatory or autoimmune diseases such as inflammatory bowel diseases, glomerulonephritis, vasculitis, psoriatic arthritis, systemic lupus erythematoses (SLE), idiopathic thrombocytopenic purpura (ITP), psoriasis, Crohn's disease, inflammatory bowel disease, ankylosing spondylitis, Sjogren's syndrome, Still's disease (macrophage activation syndrome), uveitis, scleroderma, myositis, Reiter's syndrome, and Wegener's syndrome. However, the Compounds of Formula I or pharmaceutically acceptable salts thereof (or composition comprising same) disclosed herein may be used to promote tissue self-repair and/or the tissue regeneration to treat secondary tissue damages/injuries that result from the initial physical injury, for example secondary tissue damages/injuries caused by inflammation that may occur following the initial physical injury.

Thus, in another aspect, the present invention provides a method for treating a physical injury in an organ, tissue or cell (e.g., for promoting self-repair and/or tissue regeneration of the injured organ, tissue or cell), the method comprising contacting the organ, tissue or cell with an effective amount of the compound of Formula I or pharmaceutically acceptable salt thereof (or a composition comprising same) disclosed herein.

In another aspect, the present invention provides the use of the compound of Formula I or pharmaceutically acceptable salt thereof (or a composition comprising same) disclosed herein for treating a physical injury in an organ, tissue or cell (e.g., for promoting self-repair and/or tissue regeneration of the injured organ, tissue or cell). In another aspect, the present invention provides the compound of Formula I or pharmaceutically acceptable salt thereof (or a composition comprising same) disclosed herein for use in treating a physical injury in an organ, tissue or cell (e.g., for promoting self-repair and/or tissue regeneration of the injured organ, tissue or cell).

In an embodiment, the (physically) injured organ, tissue or cell is not a kidney or kidney tissue. In another embodiment, the (physically) injured organ, tissue or cell is not a bone or bone tissue. In an embodiment, the (physically) injured organ, tissue or cell is skin, muscle, tendon, ligament, liver, heart, pancreas, an organ/tissue of the digestive/gastrointestinal tract (e.g., mouth, esophagus, stomach, intestines), gallbladder, liver, an organ of the respiratory tract (e.g., lung), spinal cord, spleen, breast, ocular tissue, a blood vessel, a periodontal tissue, mucosa (e.g., oral mucosa, nasal mucosa) and/or cartilage.

In an embodiment, the compounds of Formula I or pharmaceutically acceptable salts thereof (or composition comprising same) disclosed herein are used/administered acutely, i.e. shortly after the injury. In an embodiment, the compounds of Formula I or pharmaceutically acceptable salts thereof (or composition comprising same) disclosed herein are used/administered to promote tissue self-repair and/or the tissue regeneration prior to the development of fibrosis in the injured organ, tissue or cell, e.g. prior to the development of a fibrotic disease.

In an embodiment, the compounds of Formula I or pharmaceutically acceptable salts thereof (or composition comprising same) disclosed herein are useful for promoting wound healing.

In another embodiment, the injured organ, tissue or cell is an organ, tissue or cell of the nervous system (e.g., a neural tissue), for example an organ, tissue or cell of the central nervous system or peripheral nervous system. In an embodiment, the compounds of Formula I or pharmaceutically acceptable salts thereof (or composition comprising same) disclosed herein are useful for tissue self-repair and/or tissue regeneration following neural injury, for example spinal cord injury, peripheral nerve injury, or neural injury associated with multiple sclerosis.

In an embodiment, the compounds of Formula I or pharmaceutically acceptable salts thereof (or composition comprising same) disclosed herein are useful for tissue self-repair and/or tissue regeneration in the skin, for example following a skin cut, puncture, bruise or burn.

In an embodiment, the injured organ, tissue or cell is an organ, tissue or cell of the respiratory system, for example lungs.

In an embodiment, the injured organ, tissue or cell is liver or a liver tissue.

In an embodiment, the injured organ, tissue or cell is bladder or a bladder tissue.

In an embodiment, the injured organ, tissue or cell is an ovary or an ovarian tissue.

In an embodiment, the injured organ, tissue or cell is prostate or a prostate tissue.

In an embodiment, the injured organ, tissue or cell is spleen or a spleen tissue.

In an embodiment, the injured organ, tissue or cell is breast or a breast tissue.

In an embodiment, the injured organ, tissue or cell is a muscle, for example a muscle injured by muscle strain, muscle tear and/or any other type of physical muscle injury.

In an embodiment, the injured organ, tissue or cell is a blood vessel (e.g., an artery).

In an embodiment, the injured organ, tissue or cell is an organ/tissue of the digestive/gastrointestinal tract (e.g., mouth, esophagus, stomach, intestines)

In particular embodiments, the methods and used described herein are not for bone remodelling and/or regeneration of Islets of Langerhans. In a particular embodiment, the tissue is not a bone. In an embodiment, the tissue is not a pancreatic tissue.

The present inventors have shown that representative compounds of formula I or pharmaceutically acceptable salts thereof (or composition comprising same) disclosed herein increase markers that stimulate tissue self-repair and tissue regeneration of an injured organ in a subject. In an embodiment, the compounds of formula I described herein exert a tissue regenerative activity.

In another aspect, the present invention relates to a cosmetic composition comprising a compound of formula I or pharmaceutically acceptable salts thereof (or composition comprising same) disclosed herein. In another aspect, the present invention relates to a skin care composition comprising a compound of formula I or pharmaceutically acceptable salts thereof (or composition comprising same) disclosed herein. In another aspect, the present invention relates to an anti-aging skin care composition comprising a compound of formula I or pharmaceutically acceptable salts thereof (or composition comprising same) disclosed herein.

In another aspect, the present invention relates to the above-mentioned compound of formula I or pharmaceutically acceptable salts thereof (or composition comprising same) for use in anti-aging skin care. In another embodiment, the above-mentioned compound of formula I or composition comprising same is for use in stimulating skin repair and/or regeneration following skin damage associated with aging. In another embodiment, the above-mentioned compound or composition is for use in stimulating skin repair and/or regeneration following skin damage or injury. In an embodiment, the skin damage or injury results from exposure to UV irradiation, e.g. exposure to sun (e.g., sunburns).

In an embodiment, the methods and uses disclosed herein further comprise identifying a subject having an injured organ, tissue or cell and who is in need of a treatment with the above-mentioned compound of formula I or pharmaceutically acceptable salts thereof (or composition comprising same) for promoting tissue self-repair and/or tissue regeneration in the injured organ, tissue or cell. The method may comprise identifying in a sample from a subject, such as an organ, tissue or cell sample, a decreased level of one or more tissue self-repair and/or tissue regeneration markers, such as metalloproteinases and growth factors, including without limitation HGF, LOX (Lysyl oxidase), MMP1, MMP2, MMP9, MMP13, PLAT (tPA), PLAU (uPA), Serpin A1 (AAT), Serpin E1 (PAI-1), TIMP3, and ILK (integrin-linked kinase), and contacting the organ, tissue or cell with an effective amount of the compound of formula I or pharmaceutically acceptable salts thereof (or composition comprising same) disclosed herein.

The term "subject" includes living organisms in need of a treatment as disclosed herein, for example in which an organ is injured. The term "subject" includes animals such as mammals or birds. Preferably, the subject is a mammal, including but not limited to human, horse, dog and cat. In some embodiments, the mammal is not a mouse. More preferably, the subject is a human.

Pharmaceutical Compositions and Formulations

In an embodiment, the compounds of Formula I or pharmaceutically acceptable salts thereof described herein are comprised in pharmaceutical compositions comprising a therapeutically effective amount of the compounds or pharmaceutically acceptable salts thereof. As indicated hereinbefore, the pharmaceutical compositions may be useful: in the tissue self-repair and/or the tissue regeneration of an injured organ, in stimulating the generation of new cells in an in vitro cell culture, and/or in modulating the expression of tissue self-repair markers and/or tissue regeneration markers such as metalloproteinases and growth factors.

As used herein, the term "therapeutically effective amount" means the amount of compound that, when administered to a subject for treating or preventing a particular disorder, disease or condition, or for exerting a biological effect (e.g., to stimulate tissue self-repair and/or the tissue regeneration of an injured organ, to stimulate the generation of new cells in an in vitro cell culture, and/or to modulate (increase) the expression of tissue self-repair markers and/or tissue regeneration markers), is sufficient to effect such treatment or prevention of that disorder, disease or condition, or to exert the biological effect. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject, the properties of the compounds (e.g., bioavailability, stability, potency, toxicity, etc.), and the particular disorder(s) the subject is suffering from. In addition, the therapeutically effective amount may depend on the subject's blood parameters (e.g., calcium levels, lipid profile, insulin levels, glycemia), the severity of the disease state, organ function, or underlying disease or complications. Such appropriate doses may be determined using any available assays including the assays described herein. When one or more of the compounds of Formula I or pharmaceutically acceptable salts thereof disclosed herein is to be administered to humans, a physician may for example, prescribe a relatively low dose at first, subsequently increasing the dose until an appropriate response is obtained. The dose to be administered will ultimately be at the discretion of the health care professional. In general, however, it is envisioned that the dose for the compounds of Formula I or pharmaceutically acceptable salts thereof disclosed herein may be in the range of about 1 to about 50 mg/kg per day in human. In selected embodiments, the range may be between 1 to 30 mg/kg per day in human. In selected embodiments, the range may be between 1 to 20 mg/kg per day in human. In selected embodiments, the range may be between 5 to 18 mg/kg per day in human. In selected embodiments, the range may be between 1 to 18 mg/kg per day in human.

As used herein, the term "pharmaceutical composition" refers to the presence of at least one compound according to Formula I or pharmaceutically acceptable salts thereof as defined herein and at least one pharmaceutically acceptable carrier, diluent, vehicle or excipient. As used herein, the term "pharmaceutically acceptable carrier", "pharmaceutically acceptable diluent" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

The composition of the present invention may include one or more compounds of Formula I as defined herein or pharmaceutically acceptable derivatives, salts, prodrugs, analogues, isomers or enantiomers thereof. Formulations of the active compound may be prepared so as to provide a pharmaceutical composition in a form suitable for enteral, mucosal (including oral, sublingual, ophthalmic, nasal, pulmonary and rectal), parenteral (including intramuscular, intradermal, subcutaneous and intravenous) or topical (including ointments, creams, lotions or drops) administration. The formulation may, where appropriate, be conveniently presented in discrete dosage units and may be prepared by any of the methods well-known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well-known to the art include the use of a bolus injection, continuous infusion, biocompatible polymers or liposomes.

The above-mentioned compound or composition may be formulated in a topically applicable cosmetic composition (e.g., a topical formulation). Non-limitative examples of such topically applicable compositions include skin care cream, cleansing cream, ointment, skin care lotion, skin care gel, skin care foam, sun care composition, sunscreen skin care, make-up removal cream, make-up removal lotion, foundation cream, liquid foundation, bath and shower preparation, deodorant composition, antiperspirant composition, shaving products composition, after-shave gel or lotion, beauty aids composition, depilatory cream, soap composition, hand cleaner composition, cleansing bar, baby care, hair care, shampoo, setting lotion, treatment lotion, hair cream, hair gel, colouring composition, restructuring composition, permanent composition, or any other composition which is adapted for the use in a topical cosmetic regimen. Such compositions may further comprise one or more cosmeceutically acceptable vehicles.

Creams, as is well known in the arts of pharmaceutical and cosmeceutical formulation, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a non-ionic, anionic, cationic or amphoteric surfactant.

Lotions are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other cosmeceutically acceptable chemicals to buffer, stabilize or preserve the solute. Common examples of solvents used in preparing solutions are ethanol, water, propylene glycol or any other cosmeceutically acceptable vehicles.

Gels are semisolid, suspension-type systems. Single-phase gels contain organic macromolecules distributed substantially uniformly throughout the carrier liquid, which is typically aqueous, but also, preferably contain an alcohol, and, optionally, oil. "Organic macromolecules," i.e., gelling agents, are crosslinked acrylic acid polymers such as the "carbomer" family of polymers, e.g., carboxypolyalkylenes that may be obtained commercially under Carbopol™. Other examples are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, no irritating, and no sensitizing. As explained in Remington: The Science and Practice of Pharmacy, 19th Ed. (Easton, Pa.: Mack Publishing Co., 1995), at pages 1399-1404, and ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the anti-aging formulations. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin™ (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar head groups form an outer spherical shell, while the hydrophobic, hydrocarbon chains are oriented towards the centre of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

Kits

The compound(s) of Formula I or pharmaceutically acceptable salts thereof disclosed herein may be packaged as part of a kit, optionally including a container (e.g., packaging, a box, a vial, etc.). The kit may be commercially used according to the methods described herein and may include instructions for use in a method disclosed herein. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of Formula I or pharmaceutically acceptable salts thereof disclosed herein may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of at least one compound of Formula I as defined herein, or a pharmaceutically acceptable salt thereof, and a unit dosage form of at least one additional active ingredient. Examples of additional active ingredients that may be used in conjunction with the compounds of the invention include, but are not limited to, any of the drugs indicated hereinbefore that could be used in combination with the compound(s) Formula I or pharmaceutically acceptable salts thereof as defined herein.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container or a suitable vehicle in which the active ingredient can be dissolved to form a particulate-free sterile solution that is suitable for parenteral administration. Examples of pharmaceutically acceptable vehicles are provided hereinbefore.

EXAMPLES

The following examples further illustrate the practice of this invention but are not intended to be limiting thereof.

Example 1

Experimental Procedures for the Preparation Certain Representative Compounds All HPLC chromatograms and mass spectra were recorded on an HP 1100 LC-MS Agilent™ instrument using an analytical C18 column (250×4.6 mm, 5 microns) with a gradient over 5 min of 15-99% CH$_3$CN—H$_2$O with 0.01% TFA as the eluent and a flow of 2 mL/min.

Compound I: Synthesis of sodium salt of (3-pentylphenyl) acetic acid Using a Modified Sonogashira Procedure

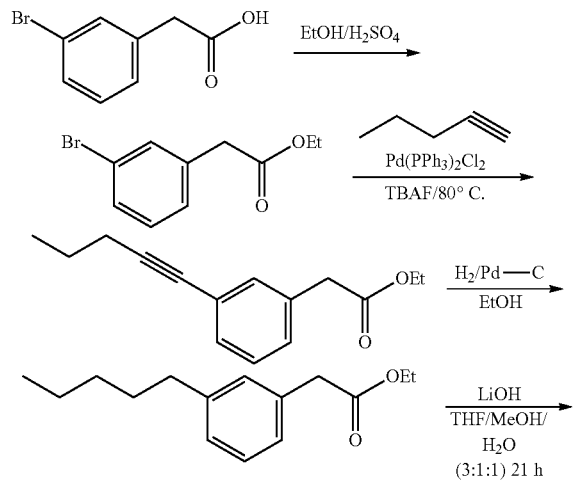

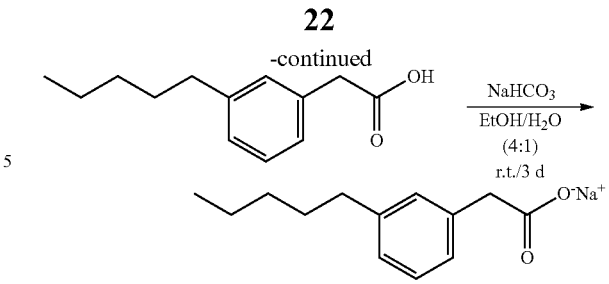

Step 1

To a solution/suspension of 3-bromophenylacetic acid (5.02 g, 23.33 mmol) in ethanol (100 mL) at room temperature was added concentrated sulfuric acid (1 mL). The colorless solid was then stirred overnight at 80° C. The solution was concentrated under reduced pressure. The residue was diluted with ethyl acetate (25 mL), water (25 mL) and the two layers were separated. The aqueous layer was extracted with ethyl acetate (2×25 mL) and brine (20 mL). The combined organic layers were washed with saturated solution of NaHCO$_3$ (2×25 mL), brine (25 mL) and dried over sodium sulfate. After filtration the solution it was evaporated to dryness. This gave a light yellow oil (5.4 g, 95%). $^1$H-NMR (400 MHz, CDCl$_3$): δ 1.26 (t, J=4.7 Hz, 3H), 3.57 (s, 2H), 4.15 (Q, J=7.0 and 14.3 Hz, 2H), 7.17-7.26 (m, 2H), 7.38-7.44 (m, 1H), 7.44 (d, J=1.56 Hz, 1H).

Step 2

A mixture of ethyl (3-bromophenyl)acetate (0.3 g, 1.24 mmol) and tetrabutylammonium fluoride hydrate (0.97 g, 3.72 mmol), was treated with PdCl$_2$(PPh$_3$)$_2$ (26 mg, 0.037 mmol; 3 mole %) and 1-pentyne (367 µL, 3.72 mmol) in a sealed tube. The tube was heated at 80° C. for 2 h. The mixture was treated with water, and was extracted with diethyl ether. The organic extract was dried over sodium sulfate, filtered and evaporated in vacuo to give the crude product. Purification on a Biotage™ 25 M column (silica), eluting with ethyl acetate/hexane 0:1 to 2:98, gave ethyl (3-(pentyne-1-yl)phenyl)acetate as a pale yellow oil (0.23 g, 79%).

Step 3

To ethyl[3-[pentyne-1-yl]phenyl]-acetate (0.23 g, 0.98 mmol) in ethanol (5 mL) under nitrogen atmosphere was added Pd on carbon (10%, 25 mg, 10% w/w). The mixture was vigorously stirred under hydrogen atmosphere at room temperature overnight. The solution was filtered and the palladium/carbon was washed with ethanol (20 mL). The filtrate was concentrated with silica gel. The crude product was purified by flash chromatography using a mixture of 10% hexanes/ethyl acetate. A clear oil was obtained (0.21 g, 90%).

Step 4

To a solution of the ester (0.2 g, 0.9 mmol) in tetrahydrofuran (5 mL), methanol (1.5 mL) and water (1.5 mL) was added lithium hydroxide (0.09 g, 3.6 mmol) at 0° C. The reaction mixture was stirred overnight at room temperature. Insolubles were filtered and the filtrate was concentrated under reduced pressure. The residue was then treated with 2 M HCl and extracted with ethyl acetate. The organic phase was dried over sodium sulfate and evaporated under reduced pressure. The crude material was purified on a 40 L Biotage column (silica) using ethyl acetate/hexanes (0:10 to 4:6) as eluant. This gave pure (3-pentylphenyl)acetic acid (0.19 g, 99%) as a white gummy solid. $^1$H NMR (400 MHz, CD$_3$OD): δ 0.90 (t, J=7.0 Hz, 3H), 1.28-1.38 (m, 4H), 1.61

(qt, J=7.6 Hz, 15.0 Hz, 2H), 2.58 (t, J=7.6 Hz, 2H), 3.56 (s, 2H), 7.07 (m, 3H), 7.20 (m, 1H); LRMS (ESI): m/z 207 (MH$^+$); HPLC: 4 min.

Step 5

To a stirred solution of the acid (0.19 g, 0.82 mmol) in ethanol (4 mL) and water (1 mL) was added sodium bicarbonate (0.07 g, 0.82 mmol). The reaction mixture was stirred at room temperature overnight. The solvent was evaporated and the white gummy solid was dissolved in water and the solution was lyophilized. This gave pure sodium salt of (3-pentylphenyl)acetic acid (0.17 g, 92%) as a white solid. mp 110-112° C.; $^1$H NMR (400 MHz, CD$_3$OD): δ 0.89 (t, J=6.8 Hz, 3H), 1.28-1.37 (m, 4H), 1.60 (qt, J=7.4 Hz, 15.0 Hz, 2H), 2.56 (t, J=7.6 Hz, 2H), 3.43 (s, 2H), 6.96 (m, 1H), 7.12 (m, 3H); LRMS (ESI): m/z 207 ((MH$^+$); HPLC: 4 min.

Compound II: Sodium salt of 3-(3-pentylphenyl)propionic acid

The above compound was prepared as for Compound I starting with 3-Oxo-3-bromophenylpropionic acid ethyl ester. The ketone group and the double bond were simultaneously reduced using palladium/carbon in ethanol under hydrogen pressure. White solid; $^1$H NMR (400 MHz, CDCl$_3$): δ 7.14-7.10 (m, 1H), 7.04-7.00 (m, 2H), 6.95-6.93 (m, 1H), 2.88-2.84 (m, 2H), 2.55 (t, J=7.4 Hz, 2H), 2.44-2.40 (m, 2H), 1.63-1.55 (m, 2H), 1.35-1.28 (m, 4H), 0.90 (m, 3H); $^{13}$C NMR (101 MHz, CD$_3$OD): δ 179.3, 141.2, 140.8, 126.7, 126.4, 124.0, 123.8, 38.6, 34.2, 31.2, 29.9, 29.8, 20.9, 11.7; LRMS (ESI): m/z 203 (MH$^+$—CO—NaOH); HPLC: 4.5 min.

Compound III: Sodium salt of 3-(3-butylphenyl)propionic acid

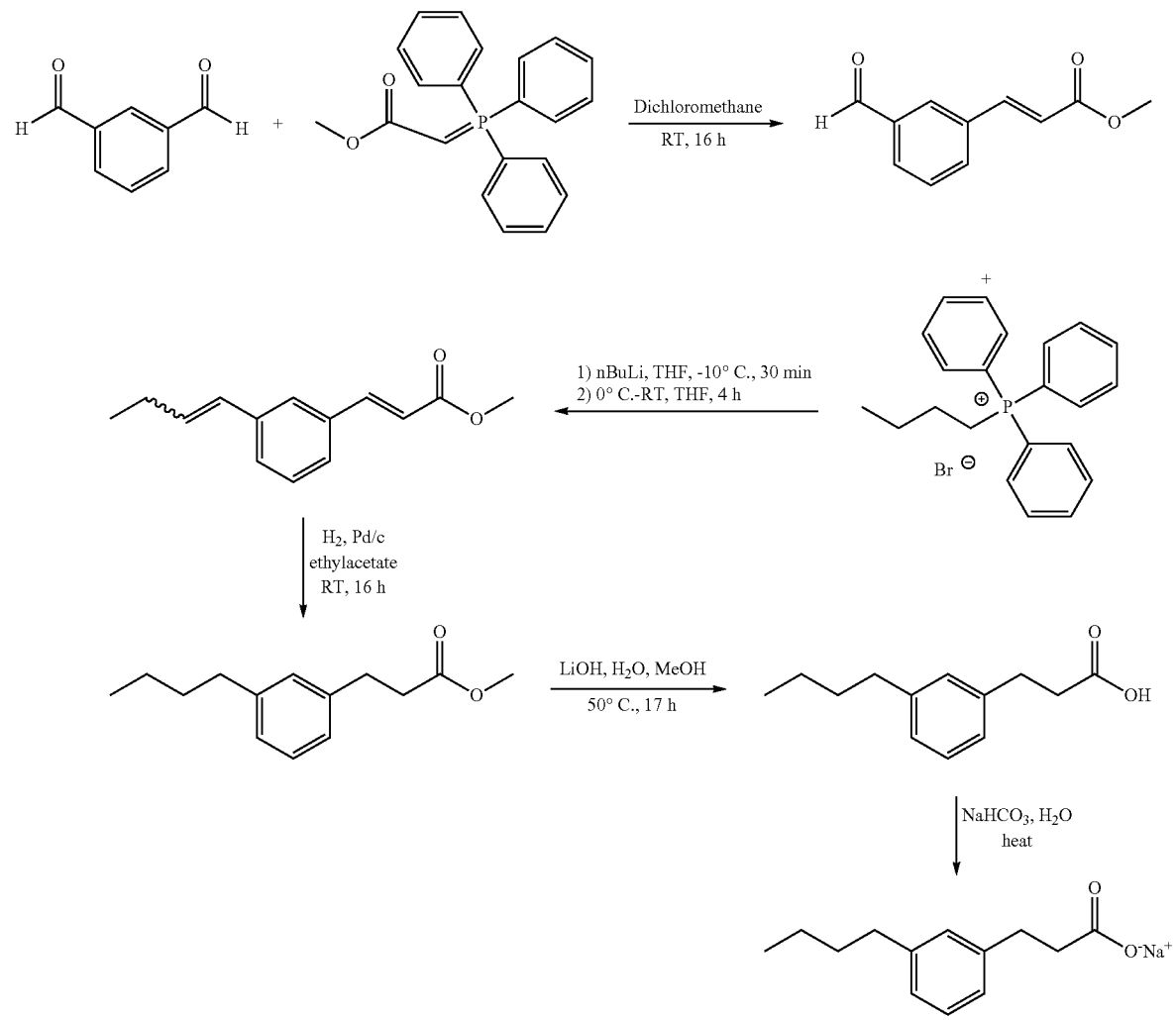

Step 1

In a round bottom flask (250 mL) was weight isophthalaldehyde (1.0 g, 7.5 mmol), followed by dichloromethane (100 mL). Via a separatory funnel with pressure equilibrium was added the Methyl (triphenyl-phosphoranylidene)acetate (2.7 g, 8.2 mmol) in dichloromethane (25 mL) at room temperature. The reaction was stirred at room temperature overnight. The mixture was filtered over a small pad of silica gel, and washed with dichloromethane (150 mL). The solvent was then evaporated under reduced pressure and the crude product was used in the next step without further purification.

Step 2

The Propyl triphenylphosphonium Bromide (3.2 g, 8.2 mmol) was placed in a round bottom flask, under nitrogen, and dry THF (5 mL) was added. The flask is cooled in an ice/acetone (−10° C.) bath, and nButyllithium (2.5 M in Hexanes, 3.28 mL, 8.2 mmol) was added slowly. The mixture turn dark colored with stirring for 30 minutes. In an ice/acetone (−10° C.) bath was placed the crude reaction mixture from the previous step in dry THF (5 mL) under nitrogen. The phosphonium solution was added slowly to the aldehyde solution at −10° C., and the reaction mixture was warmed slowly to room temperature and stirred for 4 h. Saturated ammonium chloride solution (10 mL) was added and the organic layer was extracted with ethyl acetate (3×). The organic layer was dried over anhydrous sodium sulfate, filtered and silica gel is added to obtain a drypack. Compound was purified with the SP1 (ethyl acetate/hexanes). This gave the expected product (8.8 g, 54%). $^1$H NMR (400 MHz, CDCl$_3$): δ 7.70-7.65 (m, 1H), 7.45-7.24 (m, 4.5H), 6.45-6.28 (m, 2.5H), 5.70-5.67 (m, 0.5H), 3.78 (m, 3H), 2.34-2.20 (m, 2H), 1.10-1.03 (m, 3H).

Step 3

In a round bottom flask (25 mL) is placed the unsaturated ester (140 mg, 0.65 mmol), dissolved in ethyl acetate (10 mL). To this solution was added 10% palladium on activated charcoal Pd/C (10 mg). The flask was capped with a septa, and a hydrogen balloon was placed on top. The flask was purged three times with hydrogen, and the reaction was stirred at room temperature overnight. The solid was then filtered over Celite™. Silica gel was added and a drypack is prepared. Purification by flash chromatography using 0-20% ethyl acetate/hexanes gave the desired product (124 mg, 87%). LRMS (ESI): m/z 221 (MH$^+$); HPLC: 5.0 min.

Step 4

In a round bottle flask was placed the ester (124 mg, 0.56 mmol) followed by methanol (4 mL) and lithium hydroxide (118 mg, 2.8 mmol). Water (1 mL) was added and the reaction was heated at 50° C. with agitation for 17 h. The reaction is transferred into a separatory funnel, acidified to pH lower than 4 with HCl (1M), and extracted with ethyl acetate (3×). The organic layer was dried over anhydrous sodium sulfate, filtered and evaporated. The crude material was purified by HPLC/Waters. This gave a white solid (80 mg, 70%). $^1$H NMR (400 MHz, CD$_3$OD): δ 7.16-7.12 (m, 1H), 7.01-6.96 (m, 3H), 2.88-2.84 (m, 2H), 2.57-2.53 (m, 4H), 1.60-1.52 (m, 2H), 1.37-1.28 (m, 2H), 0.91 (t, 3H, J=7.3 Hz); LRMS (ESI): m/z 205 (M-H); HPLC: 4.2 min.

Step 5

In a flask (20 mL) was placed the acid (80 mg, 0.39 mmol) followed by NaHCO$_3$ (33 mg, 0.39 mmol) and water (8 mL). To the mixtures was added acetonitrile (3 mL) and the reaction was sonicated, heated and agitated until almost all the solids were in solution. The solution was filtered over a nylon filter. The water is solidified by plunging the vial in a dry ice/acetone bath, and lyophilized overnight. This gave the desired product as a white solid. $^1$H NMR (400 MHz, CD$_3$OD): δ 7.14-7.10 (m, 1H), 7.04-6.93 (m, 3H), 2.88-2.84 (m, 2H), 2.57-2.54 (m, 2H), 2.44-2.40 (m, 4H), 1.61-1.53 (m, 2H), 1.39-1.30 (m, 2H), 0.93 (t, 3H, J=7.3 Hz); $^{13}$C NMR (101 MHZ, CD$_3$OD): δ 142.7, 142.4, 128.2, 128.0, 125.6, 125.4, 125.3, 40.1, 35.5, 33.9, 32.7, 22.2, 13.1; LRMS (ESI): m/z 251.0 (m, MNa$^+$), 229.0 (w, MH$^+$), 189.2 (100%, acylium ion [M-Na$^+$+2H$^+$—H2O]); HPLC: 4.1 min.

Compound IV: Sodium salt of E-(3-pent-1-enyl-phenyl) acetic acid

The above compound was prepared as for Compound I starting with E-(3-pent-1-enyl-phenyl)acetic acid methyl ester. The latter was prepared by reacting 3-bromophenyl acetic acid methyl ester with trans-1-pentenylboronic acid pinacol ester under Suzuki conditions. White solid; $^1$H NMR (400 MHz, CD$_3$OD): δ=7.32 (s, 1H), 7.11-7.18 (m, 3H), 6.35 (d, J=15.7 Hz, 1H), 6.20-6.27 (m, 1H), 3.44 (s, 2H), 2.19 (m, 2H), 1.45-1.54 (m, 2H), 0.96 (t, J=7.4, 3H); $^{13}$C NMR (101 MHz, CD$_3$OD): δ=179.26, 138.25, 137.92, 130.32, 130.04, 128.06, 127.59, 126.60, 123.52, 45.21, 35.06, 22.52, 12.89; LRMS (ESI): m/z 205 (MH$^+$); HPLC: 4.1 min.

Compound V: Sodium salt of 2-(3-(Hex-1-enyl]phenyl)acetic acid

The above compound was prepared by Suzuki coupling of methyl 2-(3-bromophenyl)acetate and (E)-hex-1-enylboronic acid pinacol ester as for Compound VII; followed by ester hydrolysis and sodium salt formation as for Compound I. White solid: $^1$H NMR (400 MHz, CD$_3$OD): δ 7.33 (s, 1H), 7.12-7.19 (m, 3H), 6.35 (d, J=15.8 Hz, 1H), 6.20 (dt, J=15.8, 6.8 Hz, 1H), 3.46 (s, 2H), 2.17-2.22 (m, 2H), 1.33-1.49 (m, 4H), 0.93 (t, J=7.2 Hz, 3H); $^{13}$C NMR (101 MHz, CD$_3$OD): δ 179.35, 138.27, 137.95, 130.27, 130.16, 128.10, 127.61, 126.64, 123.56, 45.24, 32.66, 31.67, 22.16, 13.22; LRMS (ESI): m/z 263.1 (100%, M+Na$^+$); HPLC: 4.4 min.

Compound VI: Sodium salt of 2-(3-Hexylphenyl)acetic acid

The above compound was prepared by Suzuki coupling of methyl 2-(3-bromophenyl)acetate and (E)-hex-1-enylboronic acid pinacol ester as for Compound VII; followed by hydrogenation, ester hydrolysis and sodium salt formation as for Compound I. White solid; $^1$H NMR (400 MHz, D$_2$O): δ 7.14 (dd, J=7.8, 7.6 Hz, 1H), 7.01 (s, 1H), 7.00 (d, J=7.8 Hz, 1H), 6.96 (d, J=7.6 Hz, 1H), 3.34 (s, 2H), 2.46 (d, J=7.5 Hz, 2H), 1.41-1.48 (m, 2H), 1.10-1.18 (m, 6H), 0.70 (t, J=6.8 Hz, 3H); $^{13}$C NMR (101 MHz, D$_2$O): δ 181.23, 143.98, 137.46, 129.47, 128.73, 126.63, 126.48, 44.58, 35.14, 31.12, 30.94, 28.23, 22.13, 13.53; LRMS (ESI): m/z 265 (100%, M+Na$^+$); HPLC: 4.6 min.

Compound VII: Sodium salt of 3-hydroxy-5-pentylphenylacetic acid

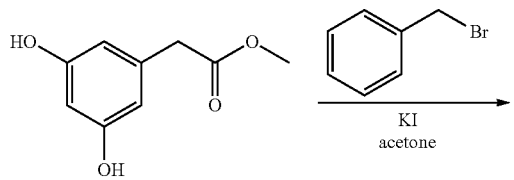

-continued

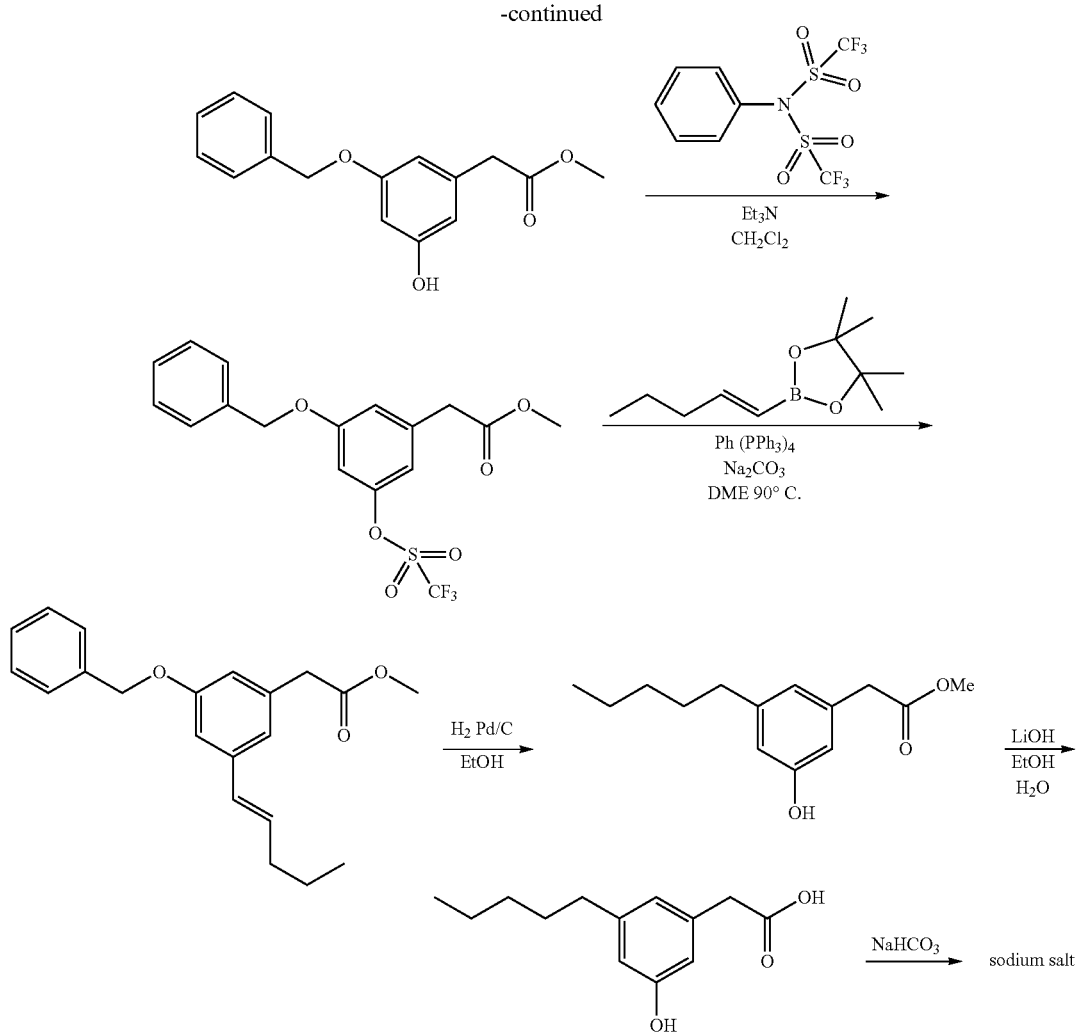

Step 1

A solution of methyl [3,5-dihydroxyphenyl]acetate (2.1 g, 11.5 mmol) in acetone (100 mL) was treated with potassium carbonate (2.4 g, 17.4 mmol), potassium iodide (383 mg, 2.31 mmol) and benzyl bromide (1.5 mL, 12.7 mmol), and the mixture was stirred at room temperature overnight. The reaction was diluted with water and extracted with dichloromethane (×3). Combined organic extracts were dried over sodium sulfate and evaporated in vacuo. The crude material was purified on a Biotage™ 40M column (silica), eluting with 40% ethyl acetate/hexane, to give methyl [3-benzyloxy-5-hydroxyphenyl]acetate (1.0 g, 33%). $^1$H NMR (400 MHz, CDCl$_3$): δ 7.32-7.42 (m, 5H), 6.48 (d, J=1.4 Hz, 1H), 6.38-6.39 (m, 2H), 4.99 (s, 2H), 3.69 (s, 3H), 3.53 (s, 2H).

Step 2

A solution of the benzyl ether (1.04 g, 3.8 mmol) in dichloromethane (15 mL) at 0° C., was treated with N-phenyl-bis(trifluorosulfonyl)imide (1.40 g, 3.9 mmol), and then triethylamine (0.6 mL, 4.1 mmol) was added slowly. The reaction was stirred at 00° C. for 1 h, and then at room temperature for 1 h. The reaction mixture was diluted with water, and then extracted with diethylether (×2). Combined organic extracts were washed with 1M aqueous sodium hydroxide, water (×2) and saturated aqueous sodium chloride, then dried over sodium sulfate, filtered and evaporated in vacuo, to give the crude product. Purification on a Biotage™ 40M column (silica), eluting with 25% ethyl acetate/hexane, gave methyl [3-benzyloxy-5-trifluoromethanesulfonyloxyphenyl]acetate (1.2 g, 79%). $^1$H NMR (400 MHz, CDCl$_3$): δ 7.36-7.46 (m, 5H), 6.98 (s, 1H), 6.97 (s, 1H), 6.84 (s, 1H), 5.06 (s, 2H), 3.72 (s, 3H), 3.63 (s, 2H).

Step 3

A solution of E-1-penten-1-ylboronic acid pinacol ester (0.8 g, 3.9 mmol) in dimethoxyethane (5 mL) was treated with a solution of the triflate (1.2 g, 3.0 mmol) in dimethoxyethane (5 mL). The solution was treated with palladium zero (0.7 g, 0.6 mmol) and 2M aqueous sodium carbonate (1.3 mL, 2.6 mmol). The mixture was then heated at 90° C. for 3 days. The reaction was cooled to room temperature and filtered through Celite™. The filtrate was evaporated in vacuo, and the crude material was purified on a Biotage™ 25M column (silica), eluting with 5% ethyl acetate/hexane, to give methyl [3-benzyloxy-5-[pent-1-enyl]phenyl]acetate (0.4 g, 40%). $^1$H NMR (400 MHz, CDCl$_3$): δ 7.36-7.47 (m, 5H), 6.90-6.92 (m, 2H), 6.79 (dd, J=2.0, 2.0 Hz, 1H), 6.35 (d, J=15.9 Hz, 1H), 6.24 (dt, J=15.9, 6.8 Hz, 1H), 5.07 (s, 2H), 3.70 (s, 3H), 3.59 (s, 2H), 2.20 (td, J=7.4, 6.8 Hz, 2H), 1.51 (dt, J=7.4 Hz, 2H), 0.98 (t, J=7.4 Hz, 3H).

Step 4

A solution of the alkene (0.4 g, 1.2 mmol) in ethanol (13 mL) was treated with 1% palladium on carbon (40 mg). The mixture was stirred under 1 atm. of hydrogen at room temperature overnight. The reaction was filtered, evaporated in vacuo, and purified on a Biotage™ 25S column (silica), eluting with 15% ethyl acetate/hexane, to give methyl [3-hydroxy-5-pentylphenyl]acetate (0.3 g, 93%). ¹H NMR (400 MHz, CDCl₃): δ 6.64 (s, 1H), 6.58-6.60 (m, 2H), 3.70 (s, 3H), 3.55 (s, 2H), 2.51 (t, J=7.7 Hz, 2H), 1.55-1.59 (m, 2H), 1.28-1.34 (m, 4H), 0.88 (t, J=7.0 Hz, 3H).

Step 5

A solution of the ester (0.3 g, 1.3 mmol) in ethanol (12 mL) was treated with water (3 mL) and lithium hydroxide (155 mg, 6.4 mmol), and the mixture was stirred vigorously at room temperature overnight. The reaction mixture was diluted with water (100 mL); washed with dichloromethane; then acidified to pH 1 with 1M aqueous hydrochloric acid acid and extracted with dichloromethane (×3). Combined organic extracts were dried over sodium sulfate (0.3 g, 95%). This material was used without further purification. ¹H NMR (400 MHz, CDCl₃): δ 6.66 (s, 1H), 6.58-6.59 (m, 2H), 3.55 (s, 2H), 2.52 (t, J=7.7 Hz, 2H), 1.55-1.59 (m, 2H).

Step 6

A solution of the acid (0.27 g, 1.23 mmol) in ethanol (6 mL) and water (6 mL) was treated with a sodium bicarbonate (0.1 g, 1.2 mmol), and the reaction was stirred at room temperature for a few hours. Solvent was concentrated in vacuo, and the solution was diluted with water, filtered (0.2 μm), and lyophilized to give sodium [3-hydroxy-5-pentylphenyl]acetate as a white solid (0.3 g, 95%). mp 63-66° C.; ¹H NMR (400 MHz, CD₃OD): δ 6.63 (s, 1H), 6.58 (s, 1H), 6.42 (s, 1H), 3.36 (s, 2H), 2.48 (t, J=7.6 Hz, 2H), 1.55-1.62 (m, 2H), 1.26-1.38 (m, 4H), 0.89 (t, J=6.8 Hz, 3H); ¹³C NMR (101 MHz, CD₃OD): δ 177.79, 155.31, 142.36, 137.62, 119.08, 111.66, 111.18, 43.70, 34.17, 29.95, 29.56, 20.87, 11.64; LRMS (ESI): m/z 445.2 (2M-2Na⁺+3H⁺), m/z 223 (M-Na⁺+2H⁺); HPLC: 3.5 min.

Compound VIII: Sodium salt of 2-(4-Hydroxy-3-pentylphenyl)acetic acid

The above compound was prepared by Suzuki coupling of benzyl 2-(4-(benzyloxy)-3-bromophenyl)acetate and (E)-pent-1-enylboronic acid pinacol ester as for example VII; followed by hydrogenation. White solid; melting point 192-195° C.; ¹H NMR (400 MHz, CD₃OD): δ 7.01 (d, J=2.3 Hz, 1H), 6.93 (dd, J=8.2, 2.3 Hz, 1H), 6.64 (d, J=8.2 Hz, 1H), 3.35 (s, 2H), 2.53 (t, J=7.7 Hz, 2H), 1.54-1.61 (m, 2H), 1.30-1.37 (m, 4H), 0.90 (t, J=7.2 Hz, 3H); ¹³C NMR (101 MHz, CD₃OD): δ 180.25, 153.20, 130.54, 128.80, 128.76, 127.10, 114.49, 44.45, 31.84, 30.10, 29.73, 22.52, 13.31; LRMS (ESI): m/z 245.2 (55%, MH⁺), 177.4 (100%, M-CO₂Na); HPLC: 1.9 min.

Compound IX: Sodium salt of 2-(2-Hydroxy-3-pentylphenyl)acetic acid

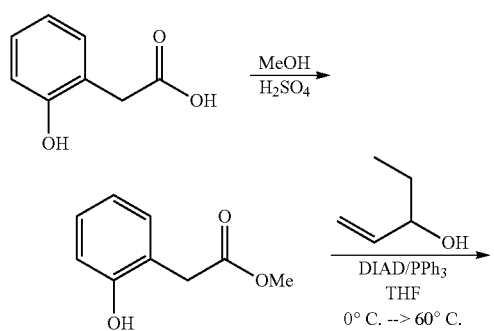

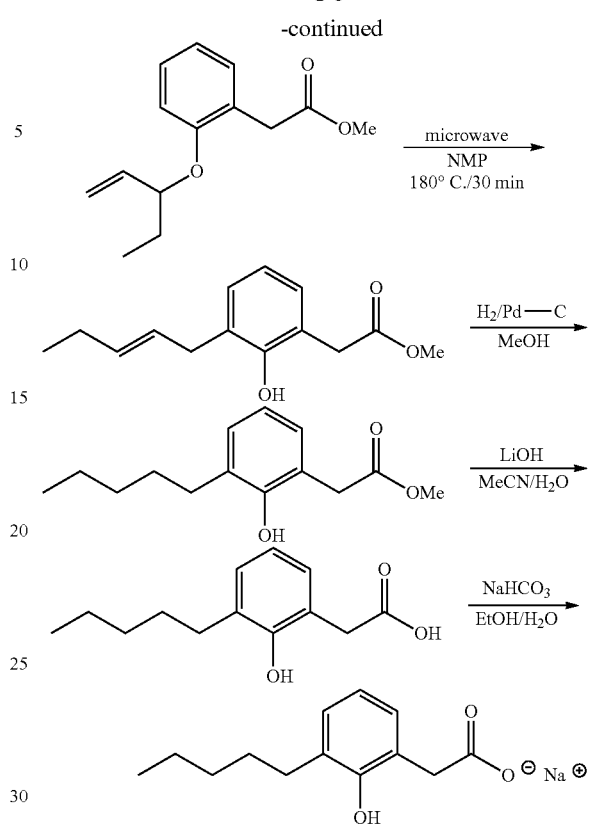

Step 1

A solution of 2-(2-hydroxyphenyl)acetic acid (3.00 g, 19.7 mmol) in methanol (40 mL) was treated with sulfuric acid (0.95 mL, 17.8 mmol) and the reaction was stirred at room temperature for 18 hours. The reaction mixture was diluted with ethyl acetate (250 mL), and the solution was washed with water (2×150 mL) and with saturated aqueous sodium chloride (150 mL); dried over sodium sulfate; filtered and evaporated in vacuo to give the crude product. Recrystallization from hot hexanes gave methyl 2-(2-hydroxyphenyl)acetate (2.83 g, 87%). ¹H NMR (400 MHz, CDCl₃): δ 7.20 (ddd, J=7.7, 7.4, 1.8 Hz, 1H), 7.09-7.11 (m, 1H), 6.94 (dd, J=8.0, 1.2 Hz, 1H), 6.88 (ddd, J=7.4, 7.4, 1.2 Hz, 1H), 3.75 (s, 3H), 3.69 (s, 2H).

Step 2

A solution of methyl 2-(2-hydroxyphenyl)acetate (1.00 g, 6.0 mmol), triphenylphosphine (2.37 g, 9.0 mmol) and pent-1-en-3-ol (0.78 g, 9.0 mmol) in tetrahydrofuran (30 mL) was cooled to 0° C. under nitrogen, and diisopropyl azodicarboxylate (1.86 mL; 9.0 mL) was added dropwise over 10 minutes. The reaction was then heated to 60° C. for 21.5 hours. Solvent was evaporated in vacuo and the residue was extracted with 5% ethyl acetate in hexanes. The extract was filtered and evaporated in vacuo to give the crude product. Purification on a Biotage™ SP1 system (120 g silica cartridge), eluting with 0-3% ethyl acetate in hexanes, gave methyl 2-(2-(pent-1-en-3-yloxy)phenyl)acetate (0.39 g, 28%). ¹H NMR (400 MHz, CDCl₃): δ 7.21-7.26 (m, 1H), 7.20 (d, J=7.6 Hz, 1H), 6.91 (ddd, J=7.4, 7.4, 1.0 Hz, 1H), 6.87 (d, J=8.0 Hz, 1H), 5.84 (ddd, J=17.4, 10.7, 6.0 Hz, 1H), 5.26 (d, J=17.4 Hz, 1H), 5.22 (d, J=10.7 Hz, 1H), 4.63 (dt, J=6.0, 6.0 Hz, 2H), 3.70 (s, 3H), 3.68 (s, 2H), 1.71-1.87 (m, 2H), 1.02 (t, J=7.5 Hz, 3H); ¹³C NMR (101 MHz, CDCl₃): δ 172.58, 156.28, 137.75, 131.19, 128.50, 123.87, 120.52, 116.66, 113.18, 79.76, 52.00, 36.61, 28.71, 9.62.

Step 3

A solution of methyl 2-(2-(pent-1-en-3-yloxy)phenyl)acetate (0.24 g, 1.0 mmol) in N-methyl-2-pyrrolidone (1.0 mL) was irradiated with microwave radiation in a Biotage Initiator at 180° C. for 30 minutes, then for 15 minutes. The solution was diluted with ethyl acetate (25 mL), then washed with water (4×25 mL) and with saturated aqueous sodium chloride (25 mL); dried over sodium sulfate; filtered and evaporated in vacuo to give the crude product. Purification on a Biotage™ SP1 system (40 g silica cartridge), eluting with 0-7% ethyl acetate in hexanes, gave methyl (E)-2-(2-hydroxy-3-(pent-2-enyl)phenyl)acetate (0.89 g, 37%). $^1$H NMR (400 MHz, CDCl$_3$): δ 7.09 (s, 1H), 7.08 (dd, J=7.4, 1.6 Hz, 1H), 7.01 (dd, J=7.6, 1.6 Hz, 1H), 6.85 (dd, J=7.6, 7.4 Hz, 1H), 5.59-5.70 (m, 2H), 3.75 (s, 3H), 3.69 (s, 2H), 3.41 (d, J=4.7 Hz, 2H), 2.04-2.11 (m, 2H), 1.01 (t, J=7.4 Hz, 3H); $^{13}$C NMR (101 MHz, CDCl$_3$): δ 174.31, 153.53, 134.44, 129.86, 129.32, 128.62, 127.13, 121.08, 120.82, 52.79, 37.59, 34.17, 25.77, 13.97.

Step 4

Methyl (E)-2-(2-hydroxy-3-(pent-2-enyl)phenyl)acetate (0.14 g, 0.6 mmol) was hydrogenated as for Compound I, step 3, but using methanol as solvent, to give methyl 2-(2-hydroxy-3-pentylphenyl)acetate (0.11 g, 76%). $^1$H NMR (400 MHz, CDCl$_3$): δ 7.57 (s, 1H), 7.11 (dd, J=7.4, 1.6 Hz, 1H), 6.96 (dd, J=7.4, 1.6 Hz, 1H), 6.84 (dd, J=7.4, 7.4 Hz, 1H), 3.76 (s, 3H), 3.70 (s, 2H), 2.68 (t, J=7.8 Hz, 2H), 1.61-1.67 (m, 2H), 1.36-1.43 (m, 4H), 0.93 (t, J=7.0 Hz, 3H); $^{13}$C NMR (101 MHz, CDCl$_3$): δ 175.01, 153.48, 131.75, 129.98, 128.75, 120.74, 120.60, 53.01, 38.30, 32.10, 30.50, 29.91, 22.87, 14.34.

Step 5

Methyl 2-(2-hydroxy-3-pentylphenyl)acetate (0.11 g, 0.5 mmol) was hydrolysed as for Compound I, step 4, using acetonitrile/water (4:1) as solvents, to give 2-(2-hydroxy-3-pentylphenyl)acetic acid (0.57 g, 57%). $^1$H NMR (400 MHz, CDCl$_3$): δ 8.70 (br s, 1H), 7.09 (dd, J=7.6, 1.6 Hz, 1H), 6.98 (dd, J=7.4, 1.6 Hz, 1H), 6.84 (dd, J=7.6, 7.4 Hz, 1H), 3.68 (s, 2H), 2.62 (t, J=7.8 Hz, 2H), 1.57-1.65 (m, 2H), 1.31-1.40 (m, 4H), 0.91 (t, J=7.0 Hz, 3H); $^{13}$C NMR (101 MHz, CDCl$_3$): δ 179.89, 152.79, 130.92, 130.04, 128.98, 121.08, 120.24, 37.74, 32.02, 30.34, 29.78, 22.80, 14.30.

Step 6

2-(2-Hydroxy-3-pentylphenyl)acetic acid (22 mg, 0.098 mmol) was converted to the sodium salt as for Compound I, step 5 to give sodium 2-(2-hydroxy-3-pentylphenyl)acetate (24 mg, 98%). $^1$H NMR (400 MHz, CD$_3$OD): δ 6.91 (dd, J=7.5, 1.6 Hz, 1H), 6.87 (dd, J=7.5, 1.6 Hz, 1H), 6.66 (dd, J=7.5, 7.5 Hz, 1H), 3.49 (s, 2H), 2.59 (t, J=7.7 Hz, 2H), 1.55-1.62 (m, 2H), 1.28-1.38 (m, 4H), 0.90 (t, J=7.0 Hz, 3H); $^{13}$C NMR (101 MHz, CD$_3$OD): δ 180.26, 154.27, 130.75, 128.21, 127.90, 124.24, 119.23, 42.91, 31.83, 30.21, 29.82, 22.51, 13.29; LRMS (ESI negative): m/z 220.8 (100%, M-Na$^+$); UPLC (System A): 5.0 min. UPLC System A: Mobile phase A=10 mM aqueous ammonium formate; mobile phase B=acetonitrile; solid phase=HSS T3 column; gradient=5-100% B in A over 10 minutes.

Compound X: Sodium salt of 2-(3-fluoro-5-pentylphenyl)acetic acid

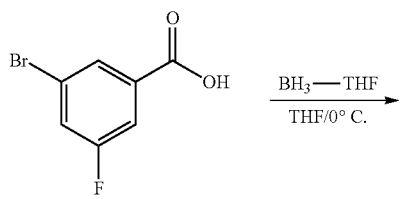

Step 1

A solution of 3-bromo-5-fluorobenzoic acid (2.74 g, 12.5 mmol) in tetrahydrofuran (6 mL), at 0° C. under nitrogen, was treated with borane-tetrahydrofuran complex (1M, 15 mL, 15 mmol) in small portions over 12 min, and the reaction was then stirred at 0° C. for 70 minutes, and at room temperature for 22 h. The reaction was quenched by addition of methanol (10 mL), and the methanolic mixture was stirred at room temperature for 3 h, and then evaporated in vacuo, with co-evaporation from methanol, then from ethyl acetate, to give the crude product. The material was dissolved in ethyl acetate (200 mL), and the solution was washed with 0.5M aqueous sodium hydroxide (200 mL), and with saturated aqueous sodium chloride (100 mL); then dried over sodium sulfate; filtered and evaporated in vacuo to give 3-bromo-5-fluorobenzyl alcohol (1.79 g, 67%). $^1$H NMR (400 MHz, CDCl$_3$): δ 7.29 (s, 1H), 7.15 (ddd, J$_{HF}$=8.2 Hz,

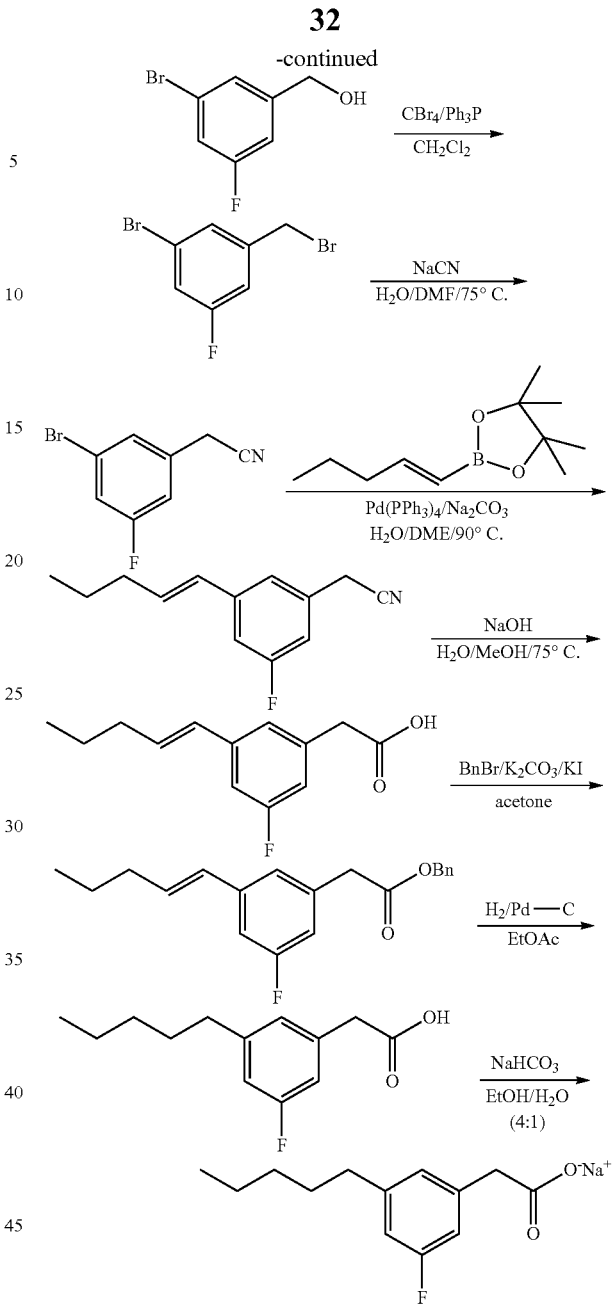

$J_{HH}$=2.2, 1.8 Hz, 1H), 7.00-7.02 and 7.02-7.04 (dm, $J_{HF}$=9.2 Hz, $J_{HH}$=unresolved, 1H), 4.66 (s, 2H), 2.04 (br s, 1H); $^{19}$F NMR (377 MHz, CDCl$_3$): δ −111.05 (dd, $J_{HF}$=9.3, 8.0 Hz, 1F); $^{13}$C NMR (101 MHz, CDCl$_3$): δ 162.87 (d, $J_{CF}$=250.6 Hz), 145.42 (d, $J_{CF}$=6.9 Hz), 125.45 (d, $J_{CF}$=3.1 Hz), 122.69 (d, $J_{CF}$=9.2 Hz), 118.01 (d, $J_{CF}$=24.6 Hz), 112.51 (d, $J_{CF}$=21.5 Hz), 63.60 (d, $J_{CF}$=2.3 Hz).

Step 2

A solution of 3-bromo-5-fluorobenzyl alcohol (1.79 g, 8.39 mmol) and triphenylphosphine (3.65 g, 10.10 mmol) in dichloromethane (45 mL), was treated with carbon tetrabromide (3.34 g, 10.10 mmol) in small portions over 10 min, and the reaction was then stirred at room temperature overnight. Solvent was evaporated in vacuo, and the residue was treated with diethyleher (50 mL). The resultant white slurry was stirred at room temperature, and then filtered through Celite™. The residue was washed with diethylether (2×50 mL), and the combined filtrate and washings were evaporated in vacuo to give the crude product. Purification on a silica pad, eluting with 2% ethyl acetate/hexane, gave 3-bromo-5-fluorobenzyl bromide (2.21 g, 98%). $^1$H NMR (400 MHz, CDCl$_3$): δ 7.33 (s, 1H), 7.18 (ddd, $J_{HF}$=8.2 Hz, $J_{HH}$=2.0, 2.0 Hz, 1H), 7.05 (ddd, $J_{HF}$=9.0 Hz, $J_{HH}$=1.8, 1.6 Hz, 1H), 4.38 (s, 2H); $^{19}$F NMR (377 MHz, CDCl$_3$): δ −110.19 to −110.14 (m, 1F); $^{13}$C NMR (101 MHz, CDCl$_3$): δ 162.67 (d, $J_{CF}$=252.1 Hz), 141.61 (d, $J_{CF}$=8.5 Hz), 128.17 (d, $J_{CF}$=3.1 Hz), 122.94 (d, $J_{CF}$=10.0 Hz), 119.39 (d, $J_{CF}$=24.6 Hz), 115.34 (d, $J_{CF}$=22.3 Hz), 31.31 (d, $J_{CF}$=2.3 Hz).

Step 3

A suspension of sodium cyanide (0.38 g, 7.73 mmol) in water (0.35 mL) was treated with a solution of 3-bromo-5-fluorobenzyl bromide (1.38 g, 5.15 mmol) in dimethylformamide (2.6 mL), and the reaction was heated at 75° C. in a sealed tube for 3 h. The reaction was cooled to room temperature and was partitioned between ethyl acetate (50 mL) and 2.5% w/v aqueous sodium bicarbonate (100 mL). The aqueous phase was extracted with a further portion of ethyl acetate (50 mL); and the combined extracts were washed with water (2×50 mL) and with saturated aqueous sodium chloride (50 mL); dried over sodium sulfate; filtered, and evaporated in vacuo to give the crude product. Purification on a Biotage™ 40iM column (silica), eluting with 10% ethyl acetate/hexane, gave 2-[3-bromo-5-fluorophenyl]acetonitrile (0.64 g, 58%). $^1$H NMR (400 MHz, CDCl$_3$): δ 7.26-7.28 (m, 1H), 7.17-7.19 & 7.19-7.21 (dm, $J_{HF}$=8.0 Hz, $J_{HH}$=unresolved, 1H), 6.98-7.00 & 7.00-7.02 (dm, $J_{HF}$=8.8 Hz, $J_{HH}$=unresolved, 1H), 3.73 (s, 2H); $^{19}$F NMR (377 MHz, CDCl$_3$): δ −109.46 (dd, $J_{HF}$=8.0, 8.0 Hz, 1F); $^{13}$C NMR (101 MHz, CDCl$_3$): δ 162.90 (d, $J_{CF}$=252.1 Hz), 133.95 (d, $J_{CF}$=8.5 Hz), 127.24 (d, $J_{CF}$=3.8 Hz), 123.53 (d, $J_{CF}$=10.0 Hz), 119.22 (d, $J_{CF}$=23.8 Hz), 117.00, 114.50 (d, $J_{CF}$=23.1 Hz), 23.30 (d, $J_{CF}$=1.5 Hz).

Step 4

A solution of the aryl bromide (0.55 g, 2.58 mmol) and (E)-1-penten-1-ylboronic acid pinacol ester (0.61 g, 3.13 mmol) in dimethoxyethane (13 mL) was treated with a solution of sodium carbonate (0.55 g, 5.17 mmol) in water (3 mL). The solution was deoxygenated with nitrogen, and was treated with tetrakis(triphenylphosphine)palladium (0.15 g, 0.13 mmol; 5 mole %). The mixture was then heated at 90° C., in a sealed tube for 17 h. The reaction was cooled to room temperature and was partitioned between ethyl acetate (50 mL) and 1M aqueous hydrochloric acid (50 mL). The organic phase was washed with saturated aqueous sodium chloride (30 mL); dried over sodium sulfate; filtered, and evaporated in vacuo to give the crude product. Purification on a Biotage™ 40iM column (silica), eluting with (3%) ethyl acetate/hexane, gave (E)-2-[3-fluoro-5-[pent-1-enyl]phenyl]acetonitrile (0.43 g, 82%). $^1$H NMR (400 MHz, CDCl$_3$): δ 7.04 (s, 1H), 6.97 (ddd, $J_{HF}$=9.8 Hz, $J_{HH}$=2.0, 1.5 Hz, 1H), 6.82-6.85 (m, 1H), 6.31 (d, J=15.8 Hz, 1H), 6.25 (ddd, J=15.8, 5.9, 0 Hz, 1H), 3.68 (s, 2H), 2.18 (td, J=7.2, 5.4 Hz, 2H), 1.49 (qt, J=7.4, 7.4 Hz, 2H), 0.95 (t, J=7.4 Hz, 3H); $^{19}$F NMR (377 MHz, CDCl$_3$): δ −112.93 (dd, $J_{HF}$=10.6, 9.3 Hz, 1F); $^{13}$C NMR (101 MHz, CDCl$_3$): δ 163.43 (d, $J_{CF}$=246.0 Hz), 141.44 (d, $J_{CF}$=8.5 Hz), 133.99, 132.37 (d, $J_{CF}$=8.5 Hz), 128.42 (d, $J_{CF}$=2.3 Hz), 121.60 (d, $J_{CF}$=3.1 Hz), 117.66, 113.40 (d, $J_{CF}$=23.1 Hz), 112.21 (d, $J_{CF}$=22.3 Hz), 35.22, 23.49 (d, $J_{CF}$=2.3 Hz), 22.51, 13.94.

Step 5

A solution of the phenylacetonitrile derivative (0.43 g, 2.10 mmol) in methanol (42 mL) was treated with aqueous sodium hydroxide (5M; 21 mL, 105 mmol), and the mixture was heated at 75° C. in a sealed tube for 4.5 h. The reaction mixture was cooled to room temperature, and was quenched with 6M aqueous hydrochloric acid (21 mL); stirred at room temperature for 10 min; then extracted with ethyl acetate (2×75 mL). The organic extract was washed with saturated aqueous sodium chloride (75 mL); dried over sodium sulfate; filtered, and evaporated in vacuo to give the crude product. Purification on a Biotage™ 40iM column (silica), eluting with 70% ethyl acetate/hexane, gave the methyl ester of the desired product (0.09 g, 18%), and ~95% pure (E)-2-[3-fluoro-5-[pent-1-enyl]phenyl]acetic acid (0.22 g, 48%). $^1$H NMR (400 MHz, CDCl$_3$): δ 11.17 (br s, 1H), 7.02 (s, 1H), 6.98 (ddd, $J_{HF}$=9.8 Hz, $J_{HH}$=2.0, 1.8 Hz, 1H), 6.85 (ddd, $J_{HF}$=9.0 Hz, $J_{HH}$=1.8, 1.6 Hz, 1H), 6.33 (d, J=15.8 Hz, 1H), 6.25 (dt, J=15.8, 6.4 Hz, 1H), 3.62 (s, 2H), 2.17-2.22 (m, 2H), 1.51 (qt, J=7.4, 7.4 Hz, 2H), 0.96 (t, J=7.4 Hz, 3H); $^{19}$F NMR (377 MHz, CDCl$_3$): δ −114.10 (dd, $J_{HF}$=9.3, 9.3 Hz, 1F).

Step 6

A solution of the partially-purified acid (0.28 g, 1.26 mmol) in acetone (5 mL) was treated with potassium carbonate (0.26 g, 1.90 mmol), potassium iodide (0.04 g, 0.25 mmol) and benzyl bromide (0.18 mL, 1.5 mmol), and the reaction was stirred at room temperature for 18 h. The reaction mixture was partitioned between ethyl acetate (25 mL) and 1M aqueous hydrochloric acid (25 mL). The organic phase was then washed with saturated aqueous sodium chloride (25 mL); dried over sodium sulfate; filtered, and evaporated in vacuo to give the crude product. Purification on a Biotage™ 40iM column (silica), eluting with 5% ethyl acetate/hexane gave benzyl (E)-2-[3-fluoro-5-[pent-1-enyl]phenyl]acetate (0.3 g, 75%). $^1$H NMR (400 MHz, CDCl$_3$): δ 7.32-7.40 (m, 5H), 7.03 (s, 1H), 6.97 (ddd, $J_{HF}$=10.0 Hz, $J_{HH}$=2.3, 1.5 Hz, 1H), 6.86 (ddd, $J_{HF}$=9.0 Hz, $J_{HH}$=2.0, 1.7 Hz, 1H), 6.33 (d, J=15.8 Hz, 1H), 6.23 (dt, J=15.8, 6.5 Hz, 1H), 5.16 (s, 2H), 3.64 (s, 2H), 2.17-2.23 (m, 2H), 1.52 (qt, J=7.4, 7.4 Hz, 2H), 0.97 (t, J=7.4 Hz, 3H); $^{19}$F NMR (377 MHz, CDCl$_3$): δ −114.34 (dd, $J_{HF}$=9.3, 9.3 Hz, 1F); $^{13}$C NMR (101 MHz, CDCl$_3$): δ 171.08, 163.32 (d, $J_{CF}$=244.4 Hz), 140.65 (d, $J_{CF}$=7.7 Hz), 136.17 (d, $J_{CF}$=8.5 Hz), 135.93, 133.05, 128.95 (d, $J_{CF}$=3.1 Hz), 128.84, 128.52 (d, $J_{CF}$=9.2 Hz), 128.48, 123.09 (d, $J_{CF}$=2.3 Hz), 114.78 (d, $J_{CF}$=22.3 Hz), 111.46 (d, $J_{CF}$=22.3 Hz), 67.04, 41.26 (d, $J_{CF}$=1.5 Hz), 35.27, 22.63, 14.00.

Step 7

A solution of the benzyl ester (0.16 g, 0.50 mmol) in ethyl acetate (2 mL) was treated with palladium on carbon (1% w/w Pd; 15 mg). The mixture was degassed with hydrogen, and was stirred under 1 atmosphere of hydrogen at room temperature overnight. The reaction was filtered, and evaporated in vacuo to give 2-[3-fluoro-5-pentylphenyl]-acetic acid (0.11 g, 97%). $^1$H NMR (400 MHz, CDCl$_3$): δ 11.47 (br s, 1H), 6.89 (s, 1H), 6.81-6.86 (m, 2H), 3.62 (s, 2H), 2.60 (t, J=7.8 Hz, 2H), 1.58-1.66 (m, 2H), 1.28-1.41 (m, 4H), 0.92 (t, J=6.8 Hz, 3H); $^{19}$F NMR (377 MHz, CDCl$_3$): δ −114.34 (dd, J$_{HF}$=9.3, 9.3 Hz, 1F); $^{13}$C NMR (101 MHz, CDCl$_3$): δ 178.15, 163.08 (d, J$_{CF}$=246.0 Hz), 145.02 (d, J$_{CF}$=7.7 Hz), 135.04 (d, J$_{CF}$=8.5 Hz), 125.49 (d, J$_{CF}$=2.3 Hz), 114.49 (d, J$_{CF}$=20.8 Hz), 113.83 (d, J$_{CF}$=22.3 Hz), 41.01 (d, J$_{CF}$=1.5 Hz), 35.87 (d, J$_{CF}$=1.5 Hz), 31.67, 31.03, 22.74, 14.24.

Step 8

A solution of the acid (0.11 g, 0.49 mmol) in ethanol (3 mL) was treated with a solution of sodium bicarbonate (0.041 g, 0.49 mmol) in water (0.75 mL), and the reaction was stirred at room temperature for 17 h. Ethanol was evaporated in vacuo, and the residual aqueous syrup was diluted with water (10 mL), filtered (0.2 μm), and lyophilised to give sodium 2-[3-fluoro-5-pentylphenyl]acetate as a white solid (0.12 g, 99%). mp 120-123° C.; $^1$H NMR (400 MHz, CD$_3$OD): δ 6.94 (s, 1H), 6.87 (ddd, J$_{HF}$=9.8 Hz, J$_{HH}$=2.0, 2.0 Hz, 1H), 6.70 (ddd, J$_{HF}$=10.0 Hz, J$_{HH}$=2.0, 2.0 Hz, 1H), 3.45 (s, 2H), 2.56 (t, J=7.7 Hz, 2H), 1.58-1.63 (m, 2H), 1.26-1.39 (m, 4H), 0.90 (t, J=7.0 Hz, 3H); $^{19}$F NMR (377 MHz, CD$_3$OD): δ −117.54 (dd, J$_{HF}$=10.0, 10.0 Hz, 1F); $^{13}$C NMR (101 MHz, CD$_3$OD): δ 178.66, 163.04 (d, J$_{CF}$=242.9 Hz), 145.07 (d, J$_{CF}$=7.7 Hz), 140.42 (d, J$_{CF}$=8.5 Hz), 125.03 (d, J$_{CF}$=2.3 Hz), 112.99 (d, J$_{CF}$=22.3 Hz), 112.30 (d, J$_{CF}$=20.8 Hz), 44.96, 35.53 (d, J$_{CF}$=1.5 Hz), 31.46, 31.00, 22.45, 13.30; HPLC: 1.2 min.

Compound XI: Sodium salt of 2-(2-Fluoro-3-pentylphenyl) acetic acid

The above compound was prepared as for Compound X, starting with 3-bromo-2-fluorobenzoic acid. White solid; $^1$H NMR (400 MHz, CD$_3$OD): δ 7.13 (ddd, J$_{HF}$=7.0 Hz, J$_{HH}$=7.4, 1.9 Hz, 2H), 7.03 (ddd, J$_{HF}$=7.0 Hz, J$_{HH}$=7.4, 1.9 Hz, 1H), 6.97 (dd, J$_{HH}$=7.4, 7.4 Hz, 1H), 3.51 (d, J$_{HF}$=1.4 Hz, 2H), 2.61 (t, J=7.6 Hz, 2H), 1.56-1.63 (m, 2H), 1.28-1.40 (m, 4H), 0.90 (t, J=6.9 Hz, 3H); $^{13}$C NMR (101 MHz, CD$_3$OD): δ 178.21, 159.70 (d, J$_{CF}$=242.9 Hz), 129.07 (d, J$_{CF}$=4.6 Hz), 128.88, 128.43 (d, J$_{CF}$=5.4 Hz), 125.02 (d, J$_{CF}$=17.7 Hz), 123.31 (d, J$_{CF}$=4.6 Hz), 37.89 (d, J$_{CF}$=3.8 Hz), 31.55, 29.98, 28.91 (d, J$_{CF}$=3.1 Hz), 22.41, 13.26; $^{19}$F NMR (377 MHz, CD$_3$OD): δ −126.09 to −126.05 (m, 1F); LRMS (ESI): m/z 220.0 (M-CO$_2$Na+acetonitrile), 179.4 (M-CO$_2$Na); HPLC: 1.2 min.

Compound XII: Sodium salt of 2-(4-Fluoro-3-pentylphenyl) acetic acid

The above compound was prepared from methyl 2-(3-bromo-4-fluorophenyl)acetate by Suzuki coupling as for Compound VII; followed by hydrogenation, ester hydrolysis and salt formation as for Compound I. The starting ester was prepared by reaction of 2-(3-bromo-4-fluorophenyl)acetic acid with methanol in the presence of sulfuric acid. White solid; $^1$H NMR (400 MHz, CD$_3$OD): δ 7.16 (dd, J$_{HF}$=7.4 Hz, J$_{HH}$=2.3 Hz, 2H), 7.08 (ddd, J$_{HF}$=5.0 Hz, J$_{HH}$=8.3, 2.3 Hz, 1H), 6.88 (dd, J$_{HF}$=10.1 Hz, J$_{HH}$=8.3 Hz, 1H), 3.40 (s, 2H), 2.59 (t, J=7.7 Hz, 2H), 1.55-1.63 (m, 2H), 1.28-1.40 (m, 4H), 0.90 (t, J=7.0 Hz, 3H); $^{13}$C NMR (101 MHz, CD$_3$OD): δ 179.12, 159.88 (d, J$_{CF}$=240.6 Hz), 133.88 (d, J$_{CF}$=3.8 Hz), 131.26 (d, J$_{CF}$=4.6 Hz), 128.78 (d, J$_{CF}$=16.1 Hz), 127.96 (d, J$_{CF}$=8.5 Hz), 114.26 (d, J$_{CF}$=23.1 Hz), 44.38, 31.51, 30.00, 28.76 (d, J$_{CF}$=1.5 Hz), 22.36, 13.18; $^{19}$F NMR (377 MHz, CD$_3$OD): δ −126.45 to −126.40 (m, 1F); LRMS (ESI): m/z 225.2 (M-Na$^+$+2H$^+$); HPLC: 1.9 min.

Compound XIII: Sodium salt of (RS)-2-Fluoro-2-(3-pentylphenyl)acetic acid

The above compound was prepared from ethyl 2-fluoro-2-(3-pentylphenyl)acetate as for Compound I. The ester was prepared by reaction of ethyl 2-(3-pentylphenyl)acetate with lithium diisopropylamide and N-fluorobenzenesulfonimide at −78° C. in Tetrahydrofuran. White solid; $^1$H NMR (400 MHz, CD$_3$OD): δ 7.34 (s, 1H), 7.30 (dd, J=7.6, 1.4 Hz, 1H), 7.24 (dd, J=7.6, 7.6 Hz, 1H), 7.13 (dd, J=7.4, 1.0 Hz, 1H), 5.53 (d, J$_{HF}$=51.3 Hz, 1H), 2.60 (t, J=7.7 Hz, 2H), 1.59-1.65 (m, 2H), 1.27-1.39 (m, 4H), 0.76 (t, J=6.9 Hz, 3H); $^{13}$C NMR (101 MHz, CD$_3$OD): δ 173.73 (d, J$_{CF}$=23.9 Hz), 141.34, 136.37 (d, J$_{CF}$=20.0 Hz), 126.79 (d, J$_{CF}$=2.3 Hz), 126.40, 125.41 (d, J$_{CF}$=5.4 Hz), 122.84 (d, J$_{CF}$=5.4 Hz), 90.34 (d, J$_{CF}$=183.4 Hz), 34.13, 29.91, 29.65, 20.85, 11.64; $^{19}$F NMR (377 MHz, CD$_3$OD): δ −168.83 (d, J$_{HF}$=51.7 Hz, 1F); LRMS (ESI negative): m/z 223.0 (100%, M-Na$^+$); HPLC: 4.1 min.

Compound XIV: Sodium 2-[3,5-Dipentylphenyl] acetate

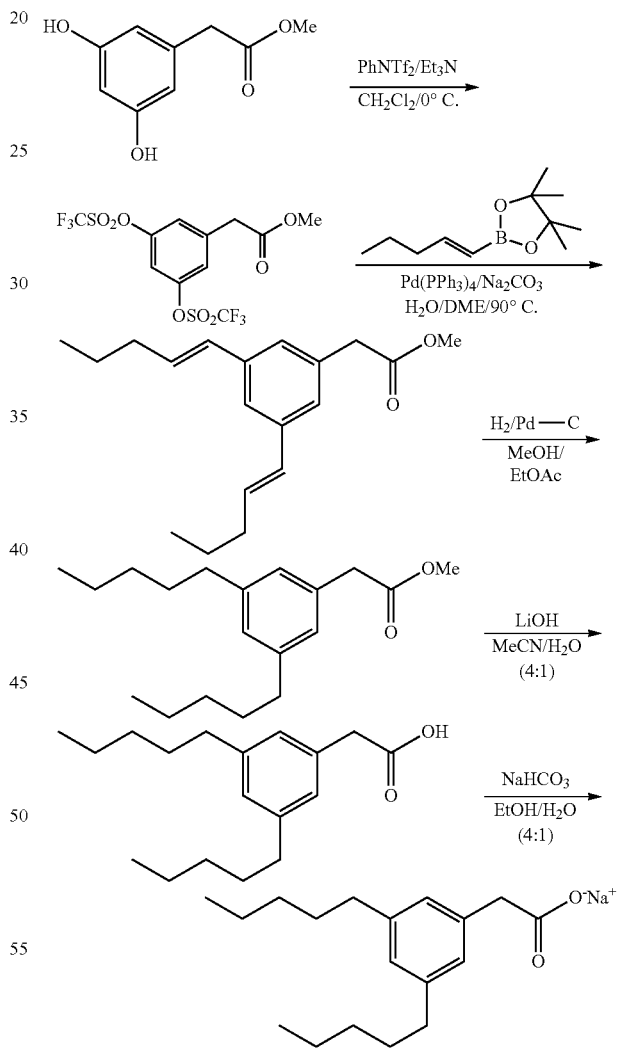

Step 1

A suspension of methyl 2-[3,5-dihydroxyphenyl]acetate (1.00 g, 5.49 mmol) and N-phenyl-bis(trifluoromethylsulfonyl)imide (4.31 g, 12.1 mmol) in dichloromethane (20 mL), at 0° C. under nitrogen, was treated with triethylamine (1.68 mL, 12.1 mmol). A clear solution formed. The reaction was then stirred under nitrogen at 00° C. for 2 h, and at room temperature for 21 h. The reaction was diluted with ethyl acetate (100 mL), and the solution was washed with 0.5M aqueous sodium hydroxide (2×100 mL), and with saturated aqueous sodium chloride (75 mL); then dried over sodium sulphate; filtered and evaporated in vacuo to give the crude product. Purification on a Biotage™ 40iM column (silica), eluting with ethyl acetate/hexane 0:1 to 1:9, gave methyl 2-[3,5-bis(trifluoromethylsulfonyloxy)phenyl]acetate (2.23 g, 91%) as pale oil. $^1$H NMR (400 MHz, CDCl$_3$): δ 7.32 (d, J=2.2 Hz, 2H), 7.18 (dd, J=2.2, 2.2 Hz, 1H), 3.72 (s, 5H); 19F NMR (377 MHz, CDCl$_3$): δ −73.20 (s, 3F); $^{13}$C NMR (101 MHz, CDCl$_3$): δ 170.05, 149.48, 139.01, 122.95, 118.87 (q, JCF=320.5 Hz), 114.42, 52.62, 40.29.

Step 2

A solution of the aryl bis(triflate) (2.23 g, 4.99 mmol) and (E)-1-penten-1-ylboronic acid pinacol ester (2.45 g, 12.5 mmol) in 1,2-dimethoxyethane (25 mL) was treated with a solution of sodium carbonate (1.59 g, 15.0 mmol) in water (8 mL). The solution was deoxygenated with nitrogen, and was then treated with Tetrakis(triphenylphosphine) palladium (0.58 g, 0.50 mmol). The mixture was heated at 90° C., in a sealed tube for 17 h. The reaction was cooled to room temperature and was partitioned between ethyl acetate (200 mL) and 1M aqueous hydrochloric acid (150 mL). The organic phase was washed with 5% aqueous sodium bicarbonate (150 mL), and with saturated aqueous sodium chloride (150 mL); then dried over sodium sulphate; filtered, and evaporated in vacuo to give the crude product. Purification on a Biotage™ 40iL column (silica), eluting with ethyl acetate/hexane 0:1 to 3:97, gave methyl 2-[3,5-di[(E)-1-pent-1-enyl]phenyl] acetate as an inseparable 10:4 mixture with excess (E)-1-penten-1-ylboronic acid pinacol ester (1.12 g, 61%). $^1$H NMR (400 MHz, CDCl$_3$): δ 7.21 (s, 1H), 7.10 (d, J=1.3 Hz, 2H), 6.34 (d, J=15.8 Hz, 1H), 6.22 (dd, J=15.8, 6.7 Hz, 1H), 3.65 (s, 3H), 3.55 (s, 2H), 2.18 (tdd, J=6.8, 6.8, 1.0 Hz, 2H), 1.49 (qt, J=7.4, 7.2 Hz, 2H), 0.96 (t, J=7.4 Hz, 3H); $^{13}$C NMR (101 MHz, CDCl$_3$): δ 172.04, 138.59, 134.47, 131.34, 129.97, 125.57, 122.75, 52.07, 41.32, 35.39, 22.77, 13.97.

Step 3

A solution of the unsaturated compound (1.12 g, 78.5% w/w, 3.07 mmol) in ethyl acetate (1 mL) and methanol (1 mL) was treated with palladium on carbon (10% w/w Pd; 0.12 g). The mixture was degassed with hydrogen, and was stirred under 1 atm. of hydrogen at room temperature for 22 h. The reaction was filtered, and evaporated in vacuo to give methyl 2-[3,5-dipentylphenyl] acetate as an inseparable 10:4 mixture with pentylboronic acid pinacol ester (0.86 g, 76%). $^1$H NMR (400 MHz, CDCl$_3$): δ 6.93 (s, 3H), 3.70 (s, 3H), 3.59 (s, 2H), 2.58 (t, J=7.9 Hz, 2H), 1.58-1.66 (m, 2H), 1.32-1.38 (m, 4H), 0.91 (t, J=6.8 Hz, 3H).

Step 4

A solution of the methyl ester (0.86 g, 79% w/w, 2.34 mmol) in acetonitrile (24 mL) was treated with a solution of lithium hydroxide (0.28 g, 11.7 mmol) in water (6 mL), and the reaction was stirred at room temperature for 22 h. The reaction was quenched with 1M aqueous hydrochloric acid (55 mL), and then extracted with ethyl acetate (100 mL). The organic extract was washed with saturated aqueous sodium chloride (50 mL); then dried over sodium sulphate; filtered, and evaporated in vacuo to give the crude product. Purification on a SiliaSep silicon oxide column, eluting with ethyl acetate/hexane 0:1 to 1:4, gave 2-[3,5-dipentyl]phenyl] acetic acid as a colorless oil (0.55 g, 84%). $^1$H NMR (400 MHz, CDCl$_3$): δ 6.99 (s, 3H), 3.65 (s, 2H), 2.63 (t, J=7.8 Hz, 2H), 1.64-71 (m, 2H), 1.36-1.44 (m, 4H), 0.97 (t, J=6.9 Hz, 3H); $^{13}$C NMR (101 MHz, CDCl$_3$): δ 178.96, 143.55, 133.21, 127.93, 127.06, 41.47, 36.13, 31.94, 31.47, 22.86, 14.34.

Step 5

A solution of the acid (0.48 g, 1.75 mmol) in ethanol (12 mL) was treated with a solution of sodium bicarbonate (0.15 g, 1.75 mmol) in water (3 mL), and the reaction was stirred at room temperature for 3 d. Ethanol was evaporated in vacuo, and the residual aqueous syrup was diluted with water (50 mL), filtered (PES, 0.2 Lm), and lyophilised to give sodium 2-[3,5-dipentylphenyl] acetate as a white solid (0.52 g, quantitative). mp 225-230° C.; $^1$H NMR (400 MHz, CD$_3$OD+D$_2$O): δ 6.92 (s, 2H), 6.76 (s, 1H), 3.41 (s, 2H), 2.50 (t, J=7.5 Hz, 2H), 1.52-1.59 (m, 2H), 1.23-1.33 (m, 4H), 0.85 (t, J=6.9 Hz, 3H); $^{13}$C NMR (101 MHz, CD$_3$OD+D$_2$O): δ 179.99, 142.66, 137.63, 126.66, 126.16, 45.11, 35.61, 31.36, 31.19, 22.41, 13.47; LRMS (ESI): m/z 277.5 (w, [M-Na++2H+]), 231.1 (100%, tropylium ion from loss of carboxy group); HPLC: 3.0 min.

Compound XV: Sodium salt of 2-(3,5-Dihexylphenyl)acetic acid

The above compound was prepared from (E)-hex-1-enyl-boronic acid pinacol ester as for Compound XIV. White solid; $^1$H NMR (400 MHz, CD$_3$OD): δ 6.96 (s, 2H), 6.79 (s, 1H), 3.43 (s, 2H), 2.54 (d, J=7.7 Hz, 4H), 1.55-1.63 (m, 4H), 1.28-1.36 (m, 12H), 0.89 (t, J=6.8 Hz, 6H); 13C NMR (101 MHz, CD$_3$OD): δ 179.68, 142.38, 137.82, 126.55, 126.07, 45.30, 35.87, 31.83, 31.67, 29.02, 22.61, 13.42; LRMS (ESI): m/z 322.0 (100%, M-Na++H++NH$_4$+) and 259.0 (35%, M-CO$_2$Na); UPLC (System A): 8.9 min. UPLC System A: Mobile phase A=10 mM aqueous ammonium bicarbonate; mobile phase B=acetonitrile; solid phase=HSS T3 column; gradient=5-100% B in A over 10 minutes.

Compound XVI: Sodium salt of 2-(2-Hydroxy-3,5-dipentylphenyl)acetic acid

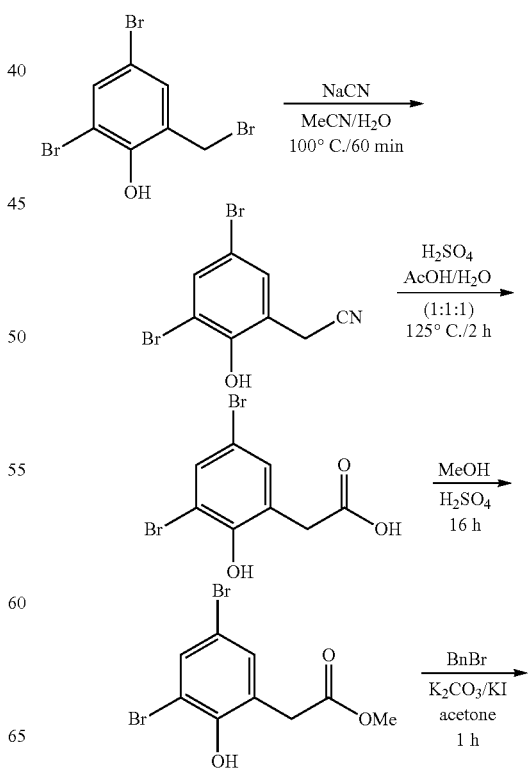

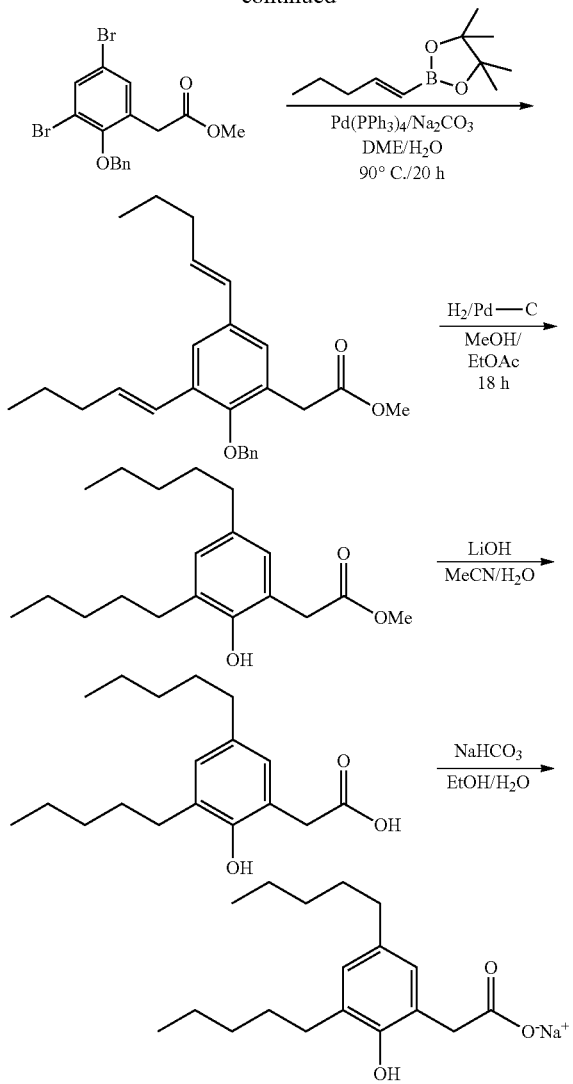

Step 1

A solution of 2,4-dibromo-6-(bromomethyl)phenol (3.5 g, 10.0 mmol) in acetonitrile (17 mL) was treated with a solution of sodium cyanide (2.5 g, 50.0 mmol) and the reaction was heated at 100° C. under reflux for 1 h. The reaction mixture cooled to room temperature and was poured into water (100 mL). The pH was adjusted from 10 to 8 with 1M aqueous hydrochloric acid, and the mixture was extracted with ethyl acetate (3×250 mL). Combined extracts were washed with 1M aqueous hydrochloric acid (250 mL) and with saturated aqueous sodium chloride (250 mL); dried over sodium sulfate; filtered and evaporated in vacuo to give the crude product. Extraction with acetone; filtration; and evaporation in vacuo gave 2-(3,5-dibromo-2-hydroxyphenyl)acetonitrile (2.6 g, 90%). $^1$H NMR (400 MHz, d6-acetone): δ 8.75 (br s, 1H), 7.69 (d, J=2.3 Hz, 1H), 7.54 (d, J=2.3 Hz, 1H), 3.92 (s, 2H); $^{13}$C NMR (101 MHz, d6-acetone): δ 151.31, 134.51, 131.92, 122.80, 117.43, 111.89, 111.53, 18.70.

Step 2

2-(3,5-Dibromo-2-hydroxyphenyl)acetonitrile (2.6 g, 9.0 mmol) was treated with a mixture of sulfuric acid (2.5 mL), acetic acid (2.5 mL) and water (2.5 mL), and the reaction was heated at 125° C. under reflux for 2 h. The reaction mixture was cooled to room temperature and was poured into a mixture of ice (50 mL) and water (50 mL), and was then stirred until the ice had melted. The mixture was extracted with ethyl acetate (250 mL); and the extract was then washed with water (100 mL) and with saturated aqueous sodium chloride (100 mL); dried over sodium sulfate; filtered and evaporated in vacuo to give the crude 2-(3,5-dibromo-2-hydroxyphenyl)acetic acid (3.1 g). This material was used directly in the next step without further purification or characterization.

Step 3

A solution of crude 2-(3,5-dibromo-2-hydroxyphenyl)acetic acid (3.1 g, 9.0 mmol) in methanol (17 mL) was treated with sulfuric acid (0.43 mL, 8.1 mmol) and the reaction was stirred at ambient temperature for 16 h. Methanol was evaporated in vacuo, and the residue was dissolved in ethyl acetate (270 mL). The solution was washed with water (2×200 mL) and with saturated aqueous sodium chloride (130 mL); dried over sodium sulfate; filtered and evaporated in vacuo to give the crude product. Purification on a Biotage™ SP1 system (120 g silica cartridge), eluting with 0-20% ethyl acetate in hexanes, gave methyl 2-(3,5-dibromo-2-hydroxyphenyl)acetate (1.4 g, 49%). $^1$H NMR (400 MHz, CDCl$_3$): δ 7.52 (d, J=2.2 Hz, 1H), 7.23 (d, J=2.2 Hz, 1H), 6.42 (br s, 1H), 3.72 (s, 3H), 3.65 (s, 2H); 13C NMR (101 MHz, CDCl$_3$): δ 172.06, 150.60, 133.74, 133.50, 123.94, 112.62, 111.77, 52.78, 36.61.

Step 4

A solution of methyl 2-(3,5-dibromo-2-hydroxyphenyl)acetate (0.5 g, 1.54 mmol) in acetone (5 mL) was treated with potassium carbonate (0.26 g, 1.86 mmol), potassium iodide (0.05 g, 0.32 mmol) and benzyl bromide (0.20 mL, 1.7 mmol), and the reaction was stirred at room temperature for 1 h. Acetone was evaporated in vacuo, and the residue was partitioned between ethyl acetate (50 mL) and 1M aqueous hydrochloric acid (50 mL). The organic phase was washed with saturated aqueous sodium chloride (50 mL); dried over sodium sulfate; filtered and evaporated in vacuo to give the crude product. Purification on a Biotage™ SP1 system (40 g silica cartridge), eluting with 0-10% ethyl acetate in hexanes, gave methyl 2-(2-(benzyloxy)-3,5-dibromophenyl)acetate (0.6 g, 95%). $^1$H NMR (400 MHz, CDCl$_3$): δ 7.67 (d, J=2.4 Hz, 1H), 7.48-7.51 (m, 2H), 7.37 (d, J=2.4 Hz, 1H), 7.34-7.43 (m, 3H), 4.99 (s, 2H), 3.66 (s, 3H), 3.60 (s, 2H); 13C NMR (101 MHz, CDCl$_3$): δ 171.26, 153.79, 136.56, 135.38, 133.57, 132.04, 128.82, 128.64, 128.52, 118.69, 117.56, 75.53, 52.50, 35.86.

Step 5

Methyl 2-(2-(benzyloxy)-3,5-dibromophenyl)acetate (0.3 g, 0.73 mmol) and (E)-pent-1-enylboronic acid pinacol ester (0.4 g, 1.79 mmol) were coupled as for Compound I, step 2, to give methyl 2-(2-(benzyloxy)-3,5-di((E)-pent-1-enyl)phenyl)acetate (0.21 mg, 72%). $^1$H NMR (400 MHz, CDCl$_3$): δ 7.50 (d, J=7.2 Hz, 2H), 7.44 (dd, J=7.2, 7.2 Hz, 2H), 7.43 (d, J=2.1 Hz, 1H), 7.38 (dd, J=7.2, 7.2 Hz, 1H), 7.18 (d, J=2.1 Hz, 1H), 6.72 (d, J=15.8 Hz, 1H), 6.39 (d, J=15.8 Hz, 1H), 6.32 (dt, J=15.8, 7.0 Hz, 1H), 6.22 (dt, J=15.8, 6.8 Hz, 1H), 4.87 (s, 2H), 3.69 (s, 3H), 3.67 (s, 2H), 2.20-2.29 (m, 4H), 1.50-1.60 (m, 4H), 1.01 (t, J=7.3 Hz, 3H), 1.00 (t, J=7.4 Hz, 3H); 13C NMR (101 MHz, CDCl$_3$): δ 172.49, 153.59, 137.58, 134.35, 132.91, 131.91, 130.84, 129.53, 128.78, 128.32, 128.30, 128.24, 127.26, 125.21, 123.89, 75.89, 52.21, 35.94, 35.74, 35.42, 22.87, 22.77, 14.07, 14.06.

Step 6

Methyl 2-(2-(benzyloxy)-3,5-di((E)-pent-1-enyl)phenyl)acetate (0.2 g, 0.53 mmol) was hydrogenated as for Compound I, step 3, to give methyl 2-(2-hydroxy-3,5-dipentylphenyl)acetate (0.12 g, 73%). $^1$H NMR (400 MHz, CDCl$_3$): δ 7.37 (s, 1H), 6.92 (d, J=2.1 Hz, 2H), 6.77 (d, J=2.1 Hz, 1H), 3.76 (s, 3H), 3.67 (s, 2H), 2.65 (t, J=7.8 Hz, 2H), 2.51 (t, J=7.8 Hz, 2H), 1.58-1.66 (m, 4H), 1.31-1.41 (m, 8H), 0.93 (t, J=7.0 Hz, 3H), 0.92 (t, J=6.9 Hz, 3H); 13C NMR (101 MHz, CDCl$_3$): δ 175.01, 151.27, 135.14, 131.48, 129.92, 128.52, 120.30, 52.95, 38.35, 35.34, 32.15, 31.86, 31.74, 30.61, 30.03, 22.87, 22.83, 14.34, 14.31.

Step 7

Methyl 2-(2-hydroxy-3,5-dipentylphenyl)acetate (0.2 g, 0.53 mmol) was hydrolysed as for Compound I, step 4, to give the crude product mixed with lactonised material. A small portion was purified on a Biotage™ SP1 system (120 g silica cartridge), eluting with 0-100% ethyl acetate in hexanes, to give 2-(2-hydroxy-3,5-dipentylphenyl)acetic acid (13.5 mg). $^1$H NMR (400 MHz, CDCl$_3$): δ 10.5 (br s, 1H), 6.89 (d, J=2.2 Hz, 1H), 6.78 (d, J=2.2 Hz, 1H), 6.32 (br s, 1H), 3.66 (s, 2H), 2.58 (t, J=7.9 Hz, 2H), 2.48 (t, J=7.8 Hz, 2H), 1.52-1.63 (m, 4H), 1.26-1.37 (m, 8H), 0.90 (t, J=7.0 Hz, 3H), 0.88 (t, J=6.8 Hz, 3H).

Step 8

2-(2-Hydroxy-3,5-dipentylphenyl)acetic acid (13.5 mg, 0.046 mmol) was converted to the sodium salt as for Compound I, step 5 to give sodium 2-(2-hydroxy-3,5-dipentylphenyl)acetate (11 mg, 77%). $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.6 Hz, 2H), 1.50-1.61 (m, 4H), 1.25-1.37 (m, 8H), 0.90 (t, J=6.8 Hz, 3H), 0.88 (t, J=7.0 Hz, 3H); 13C NMR (101 MHz, CD$_3$OD): δ 180.33, 151.94, 133.47, 130.37, 128.21, 127.81, 123.99, 42.90, 34.97, 31.81, 31.60, 31.40, 30.25, 29.88, 22.51, 22.45, 13.29, 13.24; LRMS (ESI negative): m/z 291.2 (100%, M-Na+); UPLC (System B): 7.7 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound XVII: Sodium salt of 2-(3,5-Dihexyl-2-hydroxyphenyl)acetic acid

The above compound was prepared as for Compound XVI, using (E)-hex-1-enylboronic acid pinacol ester. $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.80 Hz, 3H); LRMS (ESI negative): m/z 319 (100%, M-Na+); UPLC (System B): 8.7 min. ULC System B: Mobile phase A=0.1% aqueous formic acid; mobile phase B=0.1% formic acid in acetonitrile; solid phase=HSS T3 column; gradient=5-100% B in A over 10 minutes.

Compound XVIII: Sodium salt of 2-(4-Hydroxy-3,5-dipentylphenyl)acetic acid

The above compound was prepared as for Compound XVI, from 2-(3,5-dibromo-4-hydroxyphenyl)acetic acid. $^1$H NMR (400 MHz, CD$_3$OD): δ 6.87 (s, 2H), 3.33 (s, 2H), 2.55 (t, J=7.7 Hz, 4H), 1.53-1.61 (m, 4H), 1.31-1.37 (m, 8H), 0.90 (t, J=7.0 Hz, 6H); LRMS (ESI negative): m/z 291.1 (100%, M-Na+); UPLC (System B): 6.8 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound XIX: Sodium salt of 2-(3,5-Dihexyl-4-hydroxyphenyl)acetic acid

The above compound was prepared as for Compound XVI, from 2-(3,5-dibromo-4-hydroxyphenyl)acetic acid, and (E)-hex-1-enylboronic acid pinacol ester. $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.8 Hz, 3H); LRMS (ESI negative): m/z 319.1 (100%, M-Na+); UPLC (System B): 7.6 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound XX: Sodium salt of 2-(4-Fluoro-3,5-dihexylphenyl)acetic acid

The above compound was prepared as for Compound XVI, starting from 3,5-dibromo-4-fluorobenzyl bromide and (E)-hex-1-enylboronic acid pinacol ester. 3,5-Dibromo-4-fluorobenzyl bromide was prepared by bromination of 3,5-dibromo-4-fluorotoluene with N-bromosuccinimide and azobisisobutyronitrile in acetonitrile at 80° C. $^1$H NMR (400 MHz, CD$_3$OD): δ 6.98 (d, JHF=7.0 Hz, 2H), 3.38 (s, 2H), 2.57 (t, J=7.7 Hz, 4H), 1.54-1.61 (m, 4H), 1.28-1.37 (m, 12H), 0.89 (t, J=6.7 Hz, 6H); 19F NMR (377 MHz, CD$_3$OD): δ −132.17 (d, JHF=6.6 Hz, 1F); 13C NMR (101 MHz, CD$_3$OD): δ 179.44, 158.11 (d, JCF=239.8 Hz), 133.26 (d, JCF=3.8 Hz), 128.73 (d, JCF=5.4 Hz), 128.56 (d, JCF=16.9 Hz), 44.52, 31.69, 30.35 (d, JCF=1.5 Hz), 28.98, 28.97 (d, JCF=3.1 Hz), 22.51, 13.29; LRMS (ESI negative): m/z 321.0 (100%, M-Na+); UPLC (System B): 9.2 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound XXI: Sodium salt of 2-(4-Fluoro-3,5-dipentylphenyl)acetic acid

The above compound was prepared as for Compound XVI, starting from 3,5-dibromo-4-fluorobenzyl bromide. $^1$H NMR (400 MHz, CD$_3$OD): δ 6.98 (d, JHF=6.8 Hz, 2H), 3.37 (s, 2H), 2.57 (t, J=7.6 Hz, 4H), 1.54-1.62 (m, 4H), 1.28-1.37 (m, 8H), 0.90 (t, J=7.0 Hz, 6H); 19F NMR (377 MHz, CD$_3$OD): δ −132.34 (d, J$_{HF}$=6.6 Hz, 1F); 13C NMR (101 MHz, CD$_3$OD): δ 179.41, 158.10 (d, JCF=239.8 Hz), 133.26 (d, JCF=3.8 Hz), 128.72 (d, JCF=4.6 Hz), 128.56 (d, JCF=16.9 Hz), 44.51, 31.54, 30.07, 28.92 (d, JCF=3.1 Hz), 22.38, 13.22; LRMS (ESI negative): m/z 293.0 (100%, M-Na+); UPLC (System B): 8.4 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound XXII: Sodium salt of 2-(2-Benzyl-3,5-dipentylphenyl)acetic Acid

The title compound was prepared as for Compound XIV, from methyl 2-(2-benzyl-3,5-di((E)-pent-1-enyl)phenyl)acetate. The latter was isolated as a side product (1.1% yield) from the scale-up of Compound XIV. $^1$H NMR (400 MHz, CD$_3$OD): δ 7.17 (dd, J=7.3, 7.3 Hz, 2H), 7.09 (dd, J=7.3, 7.3 Hz, 1H), 6.97-6.99 (m, 3H), 6.86 (d, J=1.8 Hz, 1H), 4.13 (s, 2H), 3.40 (s, 2H), 2.55 (t, J=7.7 Hz, 2H), 2.49 (t, J=7.8 Hz, 2H), 1.59-1.67 (m, 2H), 1.31-1.45 (m, 6H), 1.21-1.26 (m, 4H), 0.91 (t, J=7.0 Hz, 3H), 0.82 (t, J=7.0 Hz, 3H); $^{13}$C NMR (101 MHz, CD$_3$OD): δ 179.48, 141.46, 141.24, 140.47, 137.46, 133.70, 128.36, 128.05, 127.86, 127.75, 125.42, 43.25, 35.54, 33.90, 33.61, 31.86, 31.65, 31.25, 30.96, 22.49, 22.40, 13.31, 13.23; LRMS (ESI negative): m/z 365.0 (20%, M-Na$^+$), 321.1 (100%, M-CO$_2$Na); UPLC (System B): 9 min. (UPLC System B: Mobile phase A=0.1% aqueous formic; mobile phase B=0.1% formic in acetonitrile; solid phase=HSS T3; gradient=5-100% B in A over 10 min.)

Compound XXIII: Sodium 2-[3,5-Di[(E)-Pent-1-enyl]phenyl]acetate

The title compound was prepared using the same procedure as for Compound XIV, but with the omission of the hydrogenation step. mp 226-30° C.; $^1$H NMR (400 MHz, CD$_3$OD): δ 7.18 (d, J=1.2 Hz, 2H), 7.11 (d, J=1.2 Hz, 1H), 6.34 (d, J=15.9 Hz, 2H), 2.23 (dt, J=15.9, 6.7 Hz, 2H), 3.44 (s, 2H), 2.14-2.19 (m, 4H), 1.49 (tq, J=7.4, 7.4 Hz, 4H), 0.95 (t, J=7.3 Hz, 6H); $^{13}$C NMR (101 MHz, CD$_3$OD): δ 179.41, 138.34, 138.06, 130.30, 130.16, 125.26, 121.60, 45.24, 35.10, 22.55 & 12.98; LRMS (negative mode): m/z 271 (w, [M-Na$^+$]), 227.2 (100%, [M-Na$^+$—CO$_2$]); UPLC: 8 min. (UPLC; Conditions solvent A=0.1% formic acid in water; Solvent B=0.1% formic acid in acetonitrile; Gradient: 5-100% B in A over 10 m in at 0.7 mL/min.)

Compound XXIV: Sodium 3-[3,5-Dipentylphenyl]propanoate

The title compound was prepared using the same procedure as for Compound XIV starting from 3-[3,5-dibromophenyl]propanoic acid. mp 211-217° C.; $^1$H NMR (400 MHz, CDCl$_3$): δ 6.73 (s, 1H), 6.68 (s, 2H), 2.73-2.77 (m, 2H), 2.42-2.46 (m, 2H), 2.38 (t, J=7.8 Hz, 4H), 1.43-1.51 (m, 4H), 1.19-1.28 (m, 8H), 0.83 (t, J=6.9 Hz, 6H); $^{13}$C NMR (101 MHz, CDCl$_3$): δ 182.55, 142.93, 141.85, 125.96, 125.77, 39.80, 36.13, 32.77, 31.99, 31.47, 22.79 & 14.27; LRMS (negative mode): m/z 289.4 (100%, [M-Na$^+$]); UPLC: 9 min. (UPLC: Conditions solvent A=0.1% formic acid in water, solvent B=0.1% formic acid in acetonitrile, Gradient: 5-100% B in A over 10 min at 0.7 mL/min.

Compound XXV: Sodium salt of 2-Methyl-2-(3-pentylphenyl)propanoic Acid

The tittle compound was prepared from methyl 2-[3-bromophenyl]acetate as for compound XIV, with the additional step of alkylation of the methyl 2-[3-pentylphenyl]acetate intermediate with sodium hydride and methyl iodide; and with the temperature of the ester hydrolysis step being raised to 50° C. Off-white solid: 1H NMR (400 MHz, D2O): δ 7.11 (dd, J=7.7, 7.7 Hz, 1H), 7.07 (s, 1H), 7.02 (d, J=7.6 Hz, 1H), 6.95 (d, J=7.4 Hz, 1H), 2.44 (t, J=7.7 Hz, 2H), 1.43 (tt, J=7.4, 7.4 Hz, 2H), 1.28 (s, 6H), 1.09-1.17 (m, 4H), 0.68 (t, J=7.0 Hz, 3H); 13C NMR (101 MHz, D$_2$O): δ 186.51, 148.17, 143.67, 128.48, 126.27, 126.24, 123.26, 48.67, 35.33, 30.90, 30.77, 27.20, 22.01, 13.46; LRMS (ESI+ve): m/z 189.1 (100%. MH+—CO2Na); HPLC: 5 min (15-99% acetonitrile in water over 5 min (trifluoroacetic acid in both solvents).

Compound XXVI: Sodium salt of (RS)-2-(3-Pentylphenyl) propanoic Acid

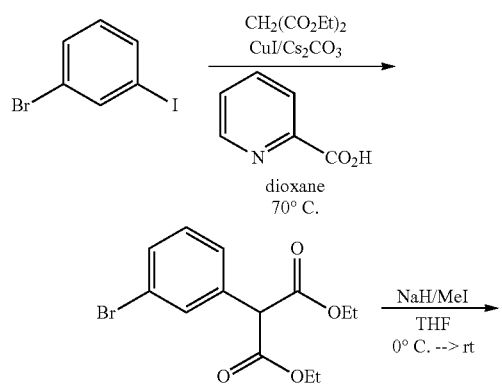

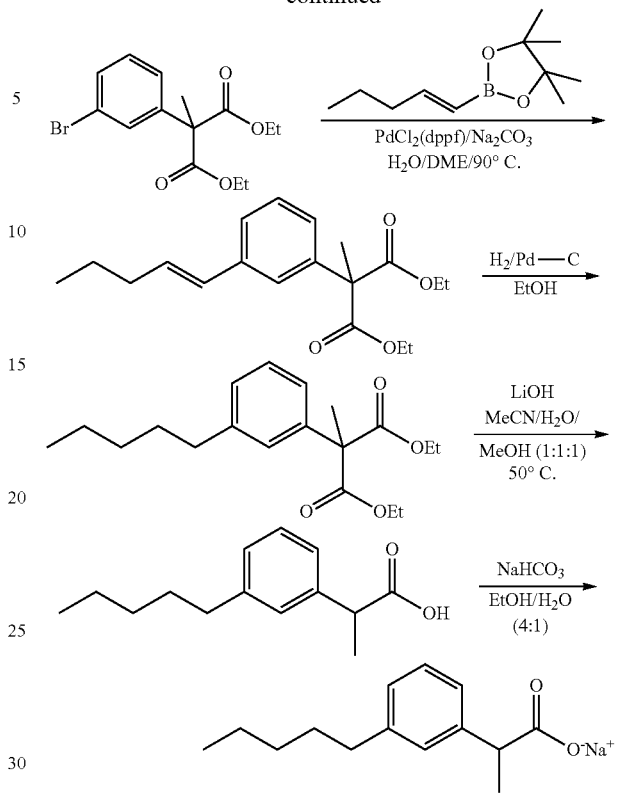

Step 1

A mixture of copper(I) iodide (17 mg, 0.09 mmol), 2-picolinic acid (22 mg, 0.18 mmol) and cesium carbonate (1.7 g, 5.30 mmol), under argon, was treated with anhydrous 1,4-dioxane (3 ml), diethyl malonate (0.54 ml, 3.5 mmol) and 1-bromo-3-iodobenzene (0.23 ml, 1.77 mmol). The reaction was then heated at 70° C., under argon, for 15 h. The crude reaction mixture was evaporated onto silica gel and purified on a SiliaSep SiO2 column, eluting with ethyl acetate in hexanes (0-12%) to give diethyl 2-[3-bromophenyl]malonate (0.34 g, 64%). 1H NMR (400 MHz, CDCl3): δ 7.30-7.47 (m, 3H), 7.20-7.26 (m, 1H), 4.16-4.24 (m, 4H), 3.36 (s, 1H), 1.23-1.29 (m, 6H).

Step 2

A suspension of sodium hydride (60% w/w; 0.53 g, 13.3 mmol) in anhydrous THF (16 ml) was cooled to 00° C. under argon, and was treated with a solution of diethyl 2-[3-bromophenyl]malonate (3.0 g, 9.52 mmol) in anhydrous THF (20 ml). The reaction mixture was stirred at 0° C. for 30 min, and was then treated dropwise with methyl iodide (0.8 ml, 13.3 mmol). The reaction mixture was then warmed to room temperature, and was stirred at room temperature, under argon, overnight. The reaction was quenched with saturated aqueous ammonium chloride solution (100 ml), and the mixture was extracted with ethyl acetate (3×100 ml). The combined organic extracts were dried (magnesium sulfate), and evaporated in vacuo to give the crude compound. Purification on a SiliaSep SiO2 column, eluting with ethyl acetate in hexanes (0-5%) gave diethyl 2-[3-bromophenyl]-2-methylmalonate (2.6 g, 82%). 1H NMR (400 MHz, CDCl3): δ 7.52 (ddd, J=1.9, 1.9, 0.4 Hz, 1H), 7.43 (ddd, J=7.9, 1.9, 1.0 Hz, 1H), 7.31 (ddd, J=8.0, 1.9, 1.0 Hz, 1H), 7.20 (ddd, J=7.9, 7.9, 0.4 Hz, 1H), 4.21-4.26 (m, 4H), 1.84 (s, 3H), 1.26 (t, J=7.2 Hz, 6H).

Step 3

Diethyl 2-[3-bromophenyl]-2-methylmalonate (2.6 g, 7.8 mmol) was coupled with (E)-1-penten-1-ylboronic acid pinacol ester (2.1 g, 10.9 mmol) using the method described for compound X, Step 4, to give diethyl (E)-2-methyl-2-[3-[pent-1-enyl]phenyl]malonate (1.7 g, 68%). 1H NMR (400 MHz, CDCl3): δ 7.24-7.32 (m, 3H), 7.21 (ddd, J=7.1, 1.9, 1.9 Hz, 1H), 6.37 (d, J=15.9 Hz, 1H), 6.20 (dt, J=15.9, 6.9 Hz, 1H), 4.21-4.26 (m, 4H), 2.15-2.21 (m, 2H), 1.87 (s, 3H), 1.49 (tt, J=7.3, 7.3 Hz, 2H), 1.26 (t, J=7.2 Hz, 6H), 0.95 (t, J=7.4 Hz, 3H).

Step 4

Diethyl (E)-2-methyl-2-[3-[pent-1-enyl]phenyl]malonate (1.4 g, 4.27 mmol) was hydrogenated using the method described for compound I, Step 3, to give diethyl 2-methyl-2-[3-pentylphenyl]malonate (1.2 g, 91%). 1H NMR (400 MHz, CDCl3): δ 7.24 (dd, J=7.3, 7.3 Hz, 1H), 7.16 (d, J=7.3 Hz, 1H), 7.15 (s, 1H), 7.10 (d, J=7.6 Hz, 1H), 4.20-4.25 (m, 4H), 2.59 (t, J=7.9 Hz, 2H), 1.85 (s, 3H), 1.49 (tt, J=7.6, 7.6 Hz, 2H), 1.28-1.34 (m, 4H), 1.25 (t, J=7.0 Hz, 6H), 0.88 (t, J=7.0 Hz, 3H).

Step 5

A solution of diethyl 2-methyl-2-[3-pentylphenyl]malonate (1.1 g, 3.5 mmol) in acetonitrile (9 ml), methanol (3 ml) and water (3 ml), was treated with lithium hydroxide (1.3 g, 52.8 mmol), and the mixture was heated at 50° C. for 48 h. The reaction mixture was concentrated in vacuo, diluted with water (10 ml), and then washed with dichloromethane (15 ml). The pH of the aqueous phase was then adjusted to pH 4 with 1M aqueous hydrochloric acid, and the mixture was extracted with dichloromethane (3×25 ml). The combined organic extracts were dried (magnesium sulphate) and evaporated in vacuo to give the crude compound. Purification on a SiliaSep SiO2 column, eluting with ethyl acetate in hexanes (0-20%) gave (RS)-2-[3-pentylphenyl]propanoic acid (0.4 g, 52%). 1H NMR (400 MHz, CD3OD): δ 7.20 (dd, J=7.6, 7.6 Hz, 1H), 7.03-7.12 (m, 3H), 3.66 (q, J=7.1 Hz, 1H), 2.58 (t, J=7.8 Hz, 2H), 1.60 (tt, J=7.6, 7.6 Hz, 2H), 1.42 (d, J=7.1 Hz, 3H), 1.27-1.38 (m, 4H), 0.90 (t, J=7.1 Hz, 3H).

Step 6

(RS)-2-[3-Pentylphenyl]propanoic acid (0.4 g, 1.8 mmol) was converted to the sodium salt using the method described for compound I, Step 5, to give sodium (RS)-2-[3-pentylphenyl]propanoate (0.44 g, quantitative). 1H NMR (400 MHz, CD3OD): δ 7.19 (s, 1H), 7.14-7.17 (m, 1H), 7.13 (dd, J=7.5, 7.5 Hz, 1H), 6.95 (d, J=6.9 Hz, 1H), 3.54 (q, J=7.1 Hz, 1H), 2.56 (t, J=7.8 Hz, 2H), 1.60 (tt, J=7.5, 7.5 Hz, 2H), 1.39 (d, J=7.2 Hz, 3H), 1.29-1.35 (m, 4H), 0.90 (t, J=7.0 Hz, 3H); 13C NMR (101 MHz, CD3OD): δ 182.18, 144.23, 142.49, 127.76, 127.55, 125.82, 124.73, 49.17, 35.85, 31.54, 31.33, 22.43, 18.95, 13.22; HPLC: 5 min (15-99% acetonitrile in water over 5 min (trifluoroacetic acid in both solvents).

Compound XXVII: Sodium salt of 2-(2-Hydroxy-5-pentylphenyl)acetic Acid

The above compound was prepared in the same manner as compound VII, Steps 3-6, using methyl 2-[2-(benzyloxy)-5-bromophenyl]acetate (prepared in 2 steps from 2-[5-bromo-2-hydroxyphenyl]acetic acid. White solid: 1H NMR (400 MHz, CD3OD): δ 6.82-6.88 (m, 2H), 6.69 (d, J=8.6 Hz, 1H), 3.47 (s, 2H), 2.47 (t, J=7.7 Hz, 2H), 1.51-1.59 (m, 2H), 1.24-1.36 (m, 4H), 0.89 (t, J=7.0 Hz, 3H); 13C NMR (101 MHz, CD3OD): δ 180.04, 154.04, 134.05, 130.25, 127.36, 124.15, 116.57, 42.50, 34.90, 31.59, 31.42, 22.44, 13.23; LRMS (ESI −ve): m/z 221.1 (100%, M-Na+), 177.1 (m, M-Na+—CO2); HPLC: 2 min (Gradient uses 70-99% acetonitrile in water over 5 min and trifluoroacetic acid in both solvents).

Compound XXVIII: Sodium salt of 2-Oxo-2-[3-pentylphenyl]acetic Acid

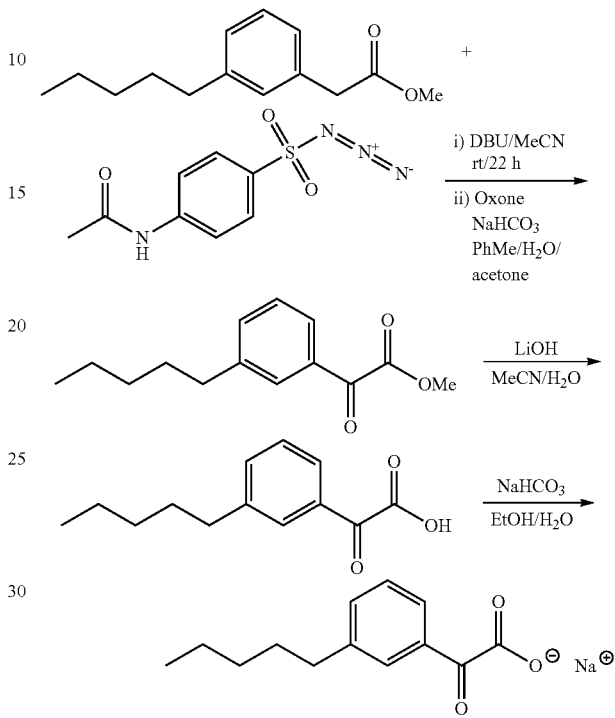

Step 1:

i) A solution of methyl 2-[3-pentylphenyl]acetate (0.5 g, 2.0 mmol) in acetonitrile (15 ml), under nitrogen, was treated with 1,8-diazabicyclo[5.4.0]undec-7-ene (0.22 ml, 1.5 mmol) and the reaction was stirred at room temperature for 15 min. The reaction was cooled to 0° C., and 4-acetamidobenzenesulfonyl azide (0.6 g, 2.4 mmol) was added slowly. The reaction was then warmed to room temperature, and was stirred, under nitrogen, for 22.5 h.

ii) This solution of the methyl 2-diazo-2-[3-pentylphenyl]acetate intermediate was diluted with toluene (15 ml), acetone (11 ml), and water (15 ml), and was then treated with sodium bicarbonate (6.4 g, 75.7 mmol). Oxone (12.1 g, 19.7 mmol) was added slowly, and the reaction mixture was then stirred vigorously at room temperature for 25 min. The reaction was diluted with water (30 ml), and then extracted with ethyl acetate (3×30 ml). The combined extracts were washed with saturated aqueous sodium chloride (30 ml), dried over sodium sulphate, and evaporated in vacuo to give the crude product. Extraction with dichloromethane and purification on a SiliaSep SiO2 column, eluting with ethyl acetate in hexanes (0-2%) gave methyl 2-oxo-2-[3-pentylphenyl]acetate (0.13 g, 30%). 1H NMR (400 MHz, CDCl3): δ 7.79-7.82 (m, 2H), 7.47 (d, J=7.6 Hz, 1H), 7.66 (dd, J=7.6, 7.6 Hz, 1H), 3.97 (s, 3H), 2.66 (d, J=7.8 Hz, 2H), 1.58-1.64 (m, 2H), 1.27-1.35 (m, 4H), 0.88 (t, J=6.9 Hz, 3H); 13C NMR (101 MHz, CDCl3): δ 186.61, 164.48, 144.17, 135.53, 132.61, 129.88, 129.01, 127.97, 52.96, 35.87, 31.58, 31.18, 22.70, 14.22.

Step 2

Methyl 2-oxo-2-[3-pentylphenyl]acetate (64 mg, 0.8 mmol) was hydrolysed as described for Compound IX, Step 5, to give 2-oxo-2-[3-pentylphenyl]acetic acid (60 mg, quant.). 1H NMR (400 MHz, CDCl3): δ 10.32 (br s, 1H), 7.98 (d, J=7.4 Hz, 1H), 7.96 (s, 1H), 7.43 (d, J=7.5 Hz, 1H), 7.36 (dd, J=7.4, 7.4 Hz, 1H), 2.60 (d, J=7.7 Hz, 2H), 1.52-1.59 (m, 2H), 1.20-1.29 (m, 4H), 0.81 (t, J=6.8 Hz, 3H); 13C NMR (101 MHz, CDCl3): δ 185.51, 164.18, 144.28, 136.10, 132.04, 130.81, 129.12, 128.85, 35.90, 31.59, 31.19, 22.71, 14.23.

Step 3

2-Oxo-2-[3-pentylphenyl]acetic acid (57 mg, 0.3 mmol) was converted to the sodium salt using the method described for compound I, Step 5, to give sodium 2-oxo-2-[3-pentylphenyl]acetate (51 mg, 95%). 1H NMR (400M Hz, CD3OD): δ 7.79-7.81 (m, 2H), 7.45 (ddd, J=7.6, 1.5, 1.5 Hz, 1H), 7.41 (ddd, J=7.8, 7.8, 1.0 Hz, 1H), 2.67 (t, J=7.6 Hz, 2H), 1.64 (tt, J=7.5, 7.5 Hz, 2H), 1.28-1.39 (m, 4H), 0.90 (t, J=7.1 Hz, 3H); 13C NMR (101 MHz, CD3OD): δ 196.19, 172.77, 143.54, 133.89, 133.76, 129.34, 128.47, 127.03, 35.45, 31.32, 31.06, 22.38, 13.20; LRMS (ESI −ve): m/z 219.1 (100%, M-Na+); HPLC: 3.3 min (Gradient uses 15-99% acetonitrile in water over 5 min and trifluoroacetic acid in both solvents).

Compound XXIX: Sodium salt of (E)-2-[2-Fluoro-5-[pent-1-enyl]phenyl]acetic Acid

The above compound was prepared from methyl 2-[2-fluoro-5-bromophenyl]acetate as for compound XIV, with the omission of the hydrogenation step. White solid; 1H NMR (400 MHz, CD3OD): δ 7.32 (dd, $J_{HF}$=7.4 Hz, $J_{HH}$=2.1 Hz, 1H), 7.15-7.18 (m, 1H), 6.92 (dd, JHF=9.4 Hz, JHH=8.8 Hz, 1H), 6.33 (d, J=15.8 Hz, 1H), 6.16 (dd, J=15.8, 7.0 Hz, 1H), 2.16 (td, J=7.1, 7.1 Hz, 2H), 1.48 (tt, J=7.3, 7.3 Hz, 2H), 0.95 (t, J=7.3 Hz, 3H); 19F NMR (377 MHz, CD3OD): δ −122.74 to −122.26 (m, 1F), 13C NMR (101 MHz, CD3OD): δ 177.91, 160.51 (d, JCF=243.6 Hz), 134.08 (d, JCF=3.8 Hz), 129.87 (d, JCF=1.5 Hz), 129.23, 128.94 (d, JCF=4.6 Hz), 125.09-125.26 (m, 2C), 114.63 (d, JCF=22.3 Hz), 37.75 (d, JCF=1.5 Hz), 35.00, 22.50, 12.87; LRMS (ESI −ve): m/z 176.9 (100%, M-Na+—CO2); HPLC: 6 min (UPLC Gradient: Mobile phase A=0.1% formic acid in water; mobile phase B=0.1% formic acid in acetonitrile; solid phase=HSS T3; gradient=5-100% B in A over 10 min).

Compound XXX: Sodium salt of 2-[2-Benzyl-5-pentylphenyl]acetic acid

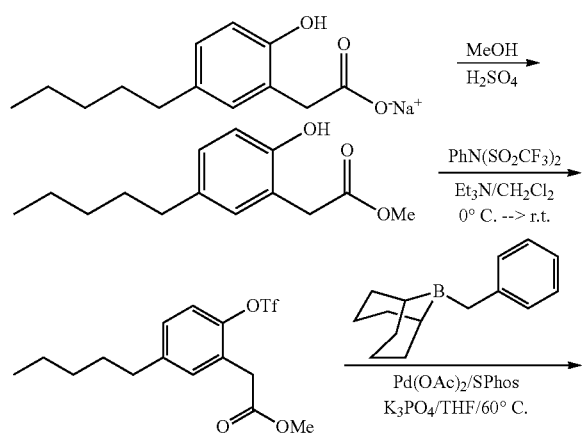

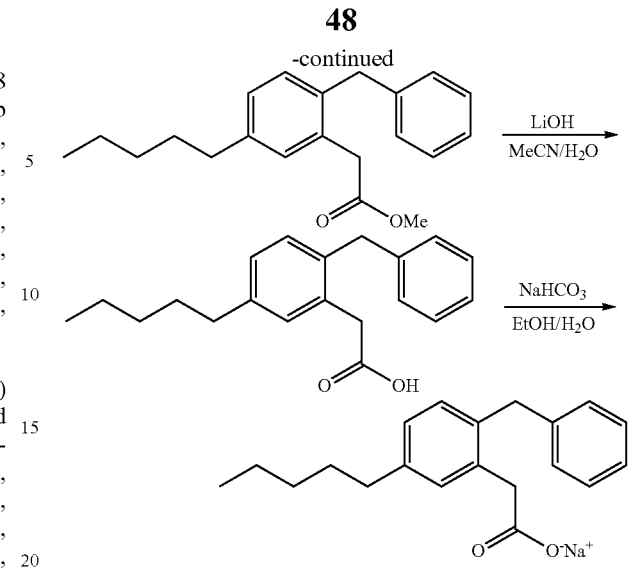

Step 1

Compound XXVII (2.4 g, 10.0 mmol) was esterified in the same manner as compound IX, Step 1, to give methyl 2-[2-hydroxy-5-pentylphenyl]acetate (2.3 g, 96%). 1H NMR (400 MHz, CDCl3): δ 7.24 (br s, 1H), 6.98 (dd, J=8.2, 2.3 Hz, 1H), 6.90 (d, J=2.3 Hz, 1H), 6.83 (d, J=8.2 Hz, 1H), 3.73 (s, 3H), 3.65 (s, 2H), 2.50 (t, J=7.9 Hz, 2H), 1.52-1.60 (m, 2H), 1.25-1.36 (m, 4H), 0.86-0.90 (m, 3H).

Step 2

Methyl 2-[2-hydroxy-5-pentylphenyl]acetate (2.3 g, 9.6 mmol) was converted to the trifluoromethanesulfonate-derivative as described for Compound VII, Step 2, to give methyl 2-[5-pentyl-2-(trifluoromethylsulfonyloxy)phenyl]acetate (3.4 g, 97%). 1H NMR (400 MHz, CDCl3): δ 7.20 (d, J=8.6 Hz, 1H), 7.18 (d, J=2.4 Hz, 1H), 7.16 (dd, J=8.6, 2.4 Hz, 1H), 3.72 (s, 3H), 3.71 (s, 2H), 2.60 (t, J=7.8 Hz, 2H), 1.56-1.64 (m, 2H), 1.27-1.37 (m, 4H), 0.89 (t, J=6.9 Hz, 3H); 19F NMR (377 MHz, CDCl3): δ −73.92 (s, 3F); 13C NMR (101 MHz, CDCl3): δ 170.59, 146.25, 143.76, 132.42, 129.30, 126.95, 121.31, 118.76 (q, JCF=319.8 Hz), 52.38, 35.70, 35.40, 31.62, 31.08, 22.66, 14.10.

Step 3

A nitrogen-flushed pressure vessel was charged sequentially with tribasic potassium phosphate (5.4 g, 25.3 mmol), palladium(II) acetate (74 mg, 0.33 mmol), 2-dicyclohexylphosphino-2',6'-dimethoxy-1,1'-biphenyl (0.14 g, 0.33 mmol), a solution of methyl 2-[5-pentyl-2-(trifluoromethylsulfonyloxy)phenyl]acetate (3.1 g, 8.3 mmol) in anhydrous tetrahydrofuran (20 ml) and a 0.5M solution of 9-benzyl-9-borabicyclo[3.3.1]nonane in tetrahydrofuran (34 ml, 17 mmol). The vessel was then sealed, and the reaction was heated at 60° C. After 17 h, the reaction mixture was cooled to room temperature and was partitioned between ethyl acetate (300 ml) and 0.5M aqueous sodium hydroxide (250 ml). The organic phase was washed with saturated aqueous sodium chloride (200 ml), dried over sodium sulphate, filtered and evaporated in vacuo to give the crude compound. Purification on a SiliaSep SiO2 column, eluting with ethyl acetate in hexanes (0-2%) gave methyl 2-[2-benzyl-5-pentylphenyl]acetate (2.5 g, 96%). 1H NMR (400 MHz, CDCl3): δ 7.29 (dd, J=7.4, 7.0 Hz, 2H), 7.21 (dd, J=7.4, 7.0 Hz, 1H), 7.13-7.15 (m, 2H), 7.08-7.09 (m, 3H), 4.04 (s, 2H), 3.63 (s, 3H), 3.60 (s, 2H), 2.61 (t, J=7.8 Hz, 2H), 1.61-1.68 (m, 2H), 1.34-1.39 (m, 4H), 0.93 (t, J=7.1 Hz, 3H); 13C NMR (101 MHz, CDCl3): δ 172.29, 141.66, 140.65, 136.61, 132.84, 131.21, 130.87, 129.03, 128.67, 127.83, 126.28, 52.19, 39.01, 39.00, 35.73, 31.89, 31.40, 22.84, 14.35.

Step 4

Methyl 2-[2-benzyl-5-pentylphenyl]acetate (2.9 g, 9.3 mmol) was hydrolysed as described for Compound IX, Step 5, to give 2-[2-benzyl-5-pentylphenyl]acetic acid (2.48 g, 90%). 1H NMR (400 MHz, CDCl3): δ 7.26 (dd, J=7.3, 7.3 Hz, 2H), 7.16 (dd, J=7.5, 7.5 Hz, 1H), 7.10-7.13 (m, 2H), 7.05-7.07 (m, 3H), 4.01 (s, 2H), 3.58 (s, 2H), 2.58 (t, J=7.8 Hz, 2H), 1.57-1.65 (m, 2H), 1.30-1.37 (m, 4H), 0.90 (t, J=7.0 Hz, 3H); 13C NMR (101 MHz, CDCl3): δ 178.67, 141.80, 140.51, 136.84, 132.20, 131.37, 130.95, 129.08, 128.75, 128.13, 136.39, 39.07, 38.98, 35.74, 31.93, 31.41, 22.87, 14.38.

Step 5

2-[2-Benzyl-5-pentylphenyl]acetic acid (2.5 g, 8.4 mmol) was converted to the sodium salt using the method described for compound I, Step 5, to give sodium 2-[2-benzyl-5-pentylphenyl]acetate (2.5 g, 93%). 1H NMR (400 MHz, CD3OD): δ 7.22 (dd, J=8.4, 7.4 Hz, 2H), 7.09-7.15 (m, 3H), 6.92-6.93 (m, 3H), 4.03 (s, 2H), 3.47 (s, 2H), 2.55 (t, J=7.8 Hz, 2H), 1.57-1.65 (m, 2H), 1.28-1.38 (m, 4H), 0.90 (t, J=7.0 Hz, 3H); 13C NMR (101 MHz, CD3OD): δ 179.25, 141.25, 140.60, 136.90, 136.48, 130.45, 129.78, 128.83, 128.13, 126.13, 125.64, 42.70, 38.49, 35.49, 31.64, 31.32, 22.51, 13.35; LRMS (ESI −ve): m/z 295.2 (40%, M-Na+), 251.2 (100%, M-Na+—CO2); HPLC: 5.0 min (Gradient uses 70-99% MeCN in water over 5 min and trifluoroacetic acid in both solvents).

Compound XXXI: Sodium salt of 2-(3,5-Di((E)-hex-1-enyl) phenyl)acetic acid

The title compound was prepared in the same manner as compound II, but with the omission of the hydrogenation step. Off-white solid: 1H NMR (400 MHz, CD3OD): δ 7.17 (d, J=1.1 Hz, 2H), 7.10 (s, 1H), 6.33 (d, J=15.8 Hz, 2H), 6.22 (dt, J=15.8, 6.7 Hz, 2H), 3.44 (s, 2H), 2.16-2.21 (m, 4H), 1.34-1.46 (m, 8H), 0.93 (t, J=7.3 Hz, 6H); 13C NMR (101 MHz, CD3OD): δ 179.44, 138.34, 138.07, 130.37, 130.13, 125.27, 121.60, 45.26, 32.70, 31.67, 22.19, 13.27; LRMS (ESI negative mode): m/z 299.2 (m, M-Na+) and 255.2 (100%, M-Na+—CO2); UPLC: 8.7 min. (UPLC conditions solvent A=0.1% formic acid in water; mobile phase B=0.1% formic acid in acetonitrile; solid phase=HSS T3; gradient=5-100% B in A over 10 min)

Compound XXXII: Sodium salt of 2-(2-Fluoro-3,5-dipentylphenyl)acetic Acid

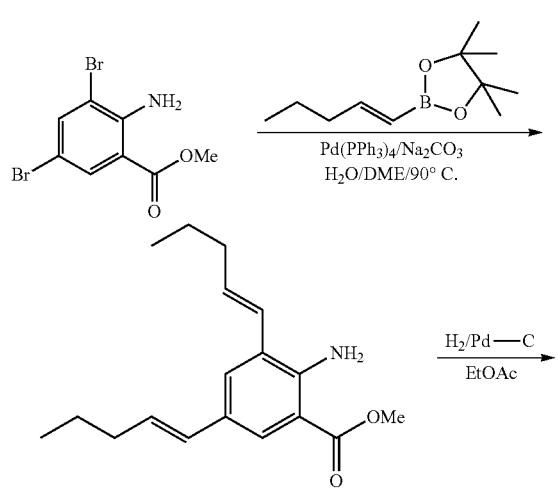

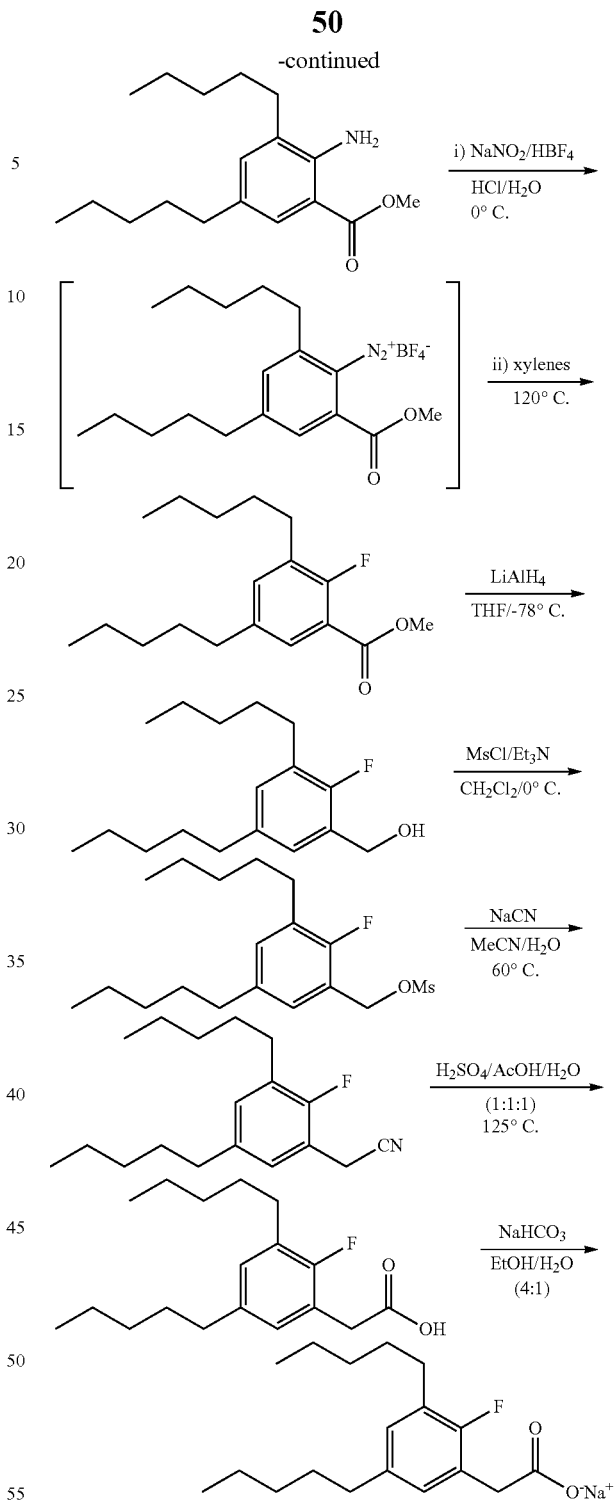

Step 1:

Methyl 2-amino-3,5-dibromobenzoate (10.0 g, 32.4 mmol) was coupled with (E)-1-penten-1-ylboronic acid pinacol ester (15.2 g, 77.7) using the method described for compound I to give methyl 2-amino-3,5-di[(E)-pent-1-enyl] benzoate (6.00 g, 64%). 1H NMR (400 MHz, CDCl3): δ 7.76 (d, J=2.2 Hz, 1H), 7.37 (d, J=2.2 Hz, 1H), 6.35 (d, J=15.4 Hz, 1H), 6.26 (d, J=15.8 Hz, 1H), 6.08 (dt, J=15.6, 7.0 Hz, 1H), 6.06 (dt, J=15.8, 7.0 Hz, 1H), 5.5-6.5 (br s, 2H), 3.87 (s, 3H), 2.19-2.25 (m, 2H), 2.13-2.18 (m, 2H), 1.43-1.56 (m, 8H), 0.97 (t, J=7.3 Hz, 3H), 0.94 (t, J=7.3 Hz, 3H).

Step 2:

Methyl 2-amino-3,5-di[(E)-pent-1-enyl]benzoate (5.7 g, 19.9 mmol) was hydrogenated as described for compound I to give methyl 2-amino-3,5-dipentylbenzoate (5.50 g, 95%). 1H NMR (400 MHz, CDCl3): δ 7.50 (d, J=2.2 Hz, 1H), 6.95 (d, J=2.2 Hz, 1H), 5.5-6.1 (br s, 2H), 3.79 (s, 3H), 2.40 (t, J=7.2 Hz, 4H), 1.45-1.58 (m, 4H), 1.20-1.32 (m, 8H), 0.84 (t, J=7.2 Hz, 3H), 0.82 (t, J=7.1 Hz, 3H).

Step 3:

Methyl 2-amino-3,5-dipentylbenzoate (4.5 g, 15.4 mmol) was treated with aqueous tetrafluoroboric acid (5.5M, 3.7 ml, 20 mmol) and aqueous hydrochloric acid (8.5M, 3.3 ml, 28 mmol). The mixture was cooled to 00° C., and was then treated dropwise with an aqueous solution of sodium nitrite (2.1M, 8.8 ml, 18.5 mmol) over 2 minutes. After 60 minutes at 0° C., the reaction mixture was extracted with xylenes (30 ml). The xylenes extract was dried over sodium sulfate, and was then heated from 60° C. to 120° C. over 55 minutes. Filtration and evaporation of xylenes in vacuo gave the crude compound, which was purified on a SiliaSep SiO2 column, eluting with ethyl acetate in hexanes (0-5%) to give methyl 2-fluoro-3,5-dipentylbenzoate (3.1 g, 69%). 1H NMR (400 MHz, CDCl3): δ 7.50 (dd, JHF=6.5 Hz, JHH=2.4 Hz, 1H), 7.15 (dd, JHF=6.5 Hz, JHH=2.4 Hz, 1H), 3.91 (s. 3H), 2.62 (td, JHH=7.7 Hz, JHF=1.2 Hz, 2H), 2.56 (t, J=7.7 Hz, 2H), 1.55-1.63 (m, 4H), 1.26-1.37 (m, 8H), 0.89 (t, J=7.0 Hz, 6H); 19F NMR (377 MHz, CDCl3): δ −121.31 (dd, JHF=6.6, 6.6 Hz, 1F).

Step 4:

A solution of methyl 2-fluoro-3,5-dipentylbenzoate (3.1 g, 10.6 mmol) in anhydrous tetrahydrofuran (60 ml) was cooled to −78° C., and was treated slowly with lithium aluminium hydride (0.5 g, 13.8 mmol). The reaction mixture was stirred at −78° C. for 25 minutes, then at 0° C. for 30 minutes. The reaction was quenched by addition of ethyl acetate. The mixture was washed with aqueous potassium sodium tartrate (1M, 100 ml), and with saturated aqueous sodium chloride (100 ml); and was then dried over sodium sulfate, filtered and evaporated in vacuo to give the crude compound. Purification on a SiliaSep SiO2 column, eluting with ethyl acetate in hexanes (3-20%) gave 2-fluoro-3,5-dipentylbenzyl alcohol (1.8 g, 65%). 1H NMR (400 MHz, CDCl3): δ 7.02 (dd, JHF=6.8 Hz, JHH=2.3 Hz, 1H), 6.92 (dd, JHF=7.1 Hz, JHH=2.4 Hz, 1H), 4.71 (s. 2H), 2.59 (td, JHH=7.6 Hz, JHF=1.2 Hz, 2H), 2.54 (t, J=7.8 Hz, 2H), 1.73 (s, 1H), 1.54-1.62 (m, 4H), 1.25-1.36 (m, 8H), 0.894 (t, J=7.0 Hz, 3H), 0.890 (t, J=7.1 Hz, 3H); 19F NMR (377 MHz, CDCl3): δ −131.25 (dd, JHF=6.7, 6.6 Hz, 1F); 13C NMR (101 MHz, CDCl3): δ 157.41 (d, JCF=242.9 Hz), 138.48 (d, JCF=4.3 Hz), 130.07 (d, JCF=5.4 Hz), 129.33 (d, JCF=16.2 Hz), 127.33 (d, JCF=15.6 Hz), 126.67 (d, JCF=4.6 Hz), 59.84 (d, JCF=5.4 Hz), 35.50, 31.86, 31.77, 31.62, 30.21, 29.21 (d, JCF=2.4 Hz), 22.80, 22.74, 14.28 (2C).

Step 5:

A solution of 2-fluoro-3,5-dipentylbenzyl alcohol (1.4 g, 5.3 mmol) in anhydrous dichloromethane (35 ml) was cooled to 00° C., and was treated dropwise with methanesulfonyl chloride (0.5 ml, 5.8 mmol) over 10 minutes. The reaction was stirred at 00° C. for 20 minutes, and was then quenched by addition of ice-cold water (35 ml). The organic phase was washed with aqueous hydrochloric acid (1M, 35 ml), saturated aqueous sodium bicarbonate (35 ml) and with saturated aqueous sodium chloride (35 ml); and was then dried over sodium sulfate, filtered and evaporated in vacuo to give the crude 2-fluoro-3,5-dipentylbenzyl methanesulfonate (1.7 g, 93%). This material was used in the next step without purification. 1H NMR (400 MHz, CDCl3): δ 7.02-7.05 (m, 2H), 5.26 (d, JHF=1.0 Hz, 2H), 2.98 (s. 3H), 2.52-2.63 (m, 2H), 2.54 (t, J=7.8 Hz, 2H), 1.54-1.62 (m, 4H), 1.27-1.37 (m, 8H), 0.892 (t, J=7.0 Hz, 3H), 0.888 (t, J=7.0 Hz, 3H).

Step 6:

The pH of a solution of sodium cyanide (0.4 g, 7.4 mmol) in water (5 ml) was adjusted to pH 10 with 6M aqueous hydrochloric acid. A solution of 2-fluoro-3,5-dipentylbenzyl methanesulfonate (1.7 g, 4.9 mmol) in acetonitrile (25 ml) was then added, and the reaction was heated at 60° C. for 2 h. The reaction mixture was concentrated to 15 ml in vacuo, and was extracted with ethyl acetate (100 ml). The organic extract was washed with water (100 ml), and with saturated aqueous sodium chloride (100 ml); and was then dried over sodium sulfate, filtered and evaporated in vacuo to give the crude compound. Purification on a SiliaSep SiO2 column, eluting with ethyl acetate in hexanes (1-10%) gave 2-[2-fluoro-3,5-dipentylphenyl]acetonitrile (0.7 g, 55%). 1H NMR (400 MHz, CDCl3): δ 7.04 (dd, JHF=6.9 Hz, JHH=2.2 Hz, 1H), 6.96 (dd, JHF=7.1 Hz, JHH=2.2 Hz, 1H), 3.72 (s. 2H), 2.59 (td, JHH=7.7 Hz, JHF=0.9 Hz, 2H), 2.55 (t, J=7.8 Hz, 2H), 1.54-1.62 (m, 4H), 1.27-1.37 (m, 8H), 0.90 (t, J=7.0 Hz, 6H); 19F NMR (377 MHz, CDCl3): δ −131.25 (ddd, JHF=7.0, 7.0, 0.8 Hz, 1F); 13C NMR (101 MHz, CDCl3): δ 157.02 (d, JCF=244.5 Hz), 139.16 (d, JCF=4.7 Hz), 130.84 (d, JCF=4.6 Hz), 129.93 (d, JCF=16.1 Hz), 126.97 (d, JCF=3.1 Hz), 117.52, 116.79 (d, JCF=16.2 Hz), 35.38, 31.74, 31.66, 31.54, 30.06, 29.16 (d, JCF=2.4 Hz), 22.74, 22.68, 17.90 (d, JCF=6.1 Hz), 14.26, 14.23.

Step 7:

A mixture of 2-[2-fluoro-3,5-dipentylphenyl]acetonitrile (0.7 g, 2.7 mmol), acetic acid (4 ml) and water (4 ml) was treated dropwise with concentrated sulfuric acid (4 ml); and the mixture was then heated at 125° C. for 3.5 h. The reaction was cooled to room temperature and was then quenched by addition of ice (40 ml). The mixture was extracted with ethyl acetate (40 ml), and the organic extract was then washed with saturated aqueous sodium chloride (40 ml); dried over sodium sulfate, filtered and evaporated in vacuo to give 2-[2-fluoro-3,5-dipentylphenyl]acetic acid (537 mg, 67%). 1H NMR (400 MHz, CDCl3): δ 6.84 (dd, JHF=7.0 Hz, JHH=2.3 Hz, 1H), 6.80 (dd, JHF=6.8 Hz, JHH=2.2 Hz, 1H), 3.59 (d, JHF=1.2 Hz, 2H), 2.52 (t, J=7.5 Hz, 2H), 2.45 (t, J=7.8 Hz, 2H), 1.46-1.55 (m, 4H), 1.20-1.30 (m, 8H), 0.80-0.84 (m, 6H).

Step 8:

2-[2-Fluoro-3,5-dipentylphenyl]acetic acid (537 mg, 1.8 mmol) was converted to the sodium salt as described for compound I to give sodium 2-[2-fluoro-3,5-dipentylphenyl]acetate (465 mg, 81%) as a pale brown, sticky solid: 1H NMR (400 MHz, CD3OD): δ 6.94 (dd, JHF=6.9 Hz, JHH=2.2 Hz, 1H), 6.83 (dd, JHF=7.0 Hz, JHH=2.3 Hz, 1H), 3.48 (d, JHF=1.1 Hz, 2H), 2.58 (t, J=7.6 Hz, 2H), 2.51 (t, J=7.6 Hz, 2H), 1.54-1.62 (m, 4H), 1.28-1.38 (m, 8H), 0.90 (t, J=7.0 Hz, 3H), 0.89 (t, J=7.0 Hz, 3H); 19F NMR (377 MHz, CD3OD): δ −130.71 (dd, JHF=6.6, 6.6 Hz, 1F); 13C NMR (101 MHz, CD3OD): δ 178.31, 157.95 (d, JCF=240.6 Hz), 137.64 (d, JCF=3.8 Hz), 128.72 (d, JCF=4.6 Hz), 128.42 (d, JCF=17.7 Hz), 128.21 (d, JCF=5.4 Hz), 124.50 (d, JCF=17.7 Hz), 37.94 (d, JCF=3.1 Hz), 35.05, 31.52, 31.45, 31.37, 30.00, 28.96 (d, JCF=2.3 Hz), 22.43, 22.38, 13.23, 13.21; LRMS (ESI negative mode): m/z 293 (w, M-Na+) and 249.1 (100%, M-Na+—CO2); UPLC: 8.4 min (UPLC conditions Mobile phase A=0.1% formic acid in water; mobile phase B=0.1% formic acid in acetonitrile; solid phase=HSS T3; gradient=5-100% B in A over 10 min.

Compound XXXIII: Sodium salt of 2-(3,5-Dipentylphenyl)-2-methylpropanoic Acid

The above compound was prepared in the same manner as compound I, with the additional step of alkylation of the methyl 2-[3,5-dipentylphenyl]acetate intermediate with sodium hydride and methyl iodide; and with the temperature of the ester hydrolysis step being raised to 100° C. Off-white solid: $^1$H NMR (400 MHz, CD$_3$OD): δ 7.04 (d, J=1.3 Hz, 2H), 6.76 (s, 1H), 2.54 (t, J=7.7 Hz, 4H), 1.55-1.63 (m, 4H), 1.46 (s, 6H), 1.27-1.38 (m, 8H), 0.90 (t, J=7.0 Hz, 6H); $^{13}$C NMR (101 MHz, CD$_3$OD): δ 184.58, 148.51, 141.98, 125.57, 123.46, 36.02, 48.26, 31.59, 31.42, 27.57, 22.47, 13.29; LRMS (ESI negative mode): m/z 303.1 (100%, M-Na$^+$); UPLC: 8.9 min (UPLC conditions mobile phase A=0.1% formic acid in water; mobile phase B=0.1% formic acid in acetonitrile; solid phase=HSS T3; gradient=5-100% B in A over 10 min).

Example 2

Effect of Representative Compounds of Formula I on Expression of Hepatocyte Growth Factor (HGF), for Tissue Self-Repair, Regeneration and Anti-aging Experiments were undertaken to determine the effect of compounds on hepatocyte growth factor expression in vitro normal human dermal fibroblasts (NHDF) from adult donor (Clonetics #CC-2511). NHDF were starved overnight in DMEM/F12+0.5% FBS and treated with or without rhTGF-β1 (10 ng/ml) and compound I (500 μM) for 24 h. RNA was isolated with miRNeasy® kit (QIAGEN®), including on-column DNase digestion step. cDNA synthesis was done (0.5 μg RNA/reaction) using the RT$^2$ First Strand kit (QIAGEN® #330401). Real-Time PCR was performed as described in the RT$^2$ Profiler PCR Array handbook on a AB-7900HT real-time cycler. Real-Time PCR data was analyzed using the ΔΔCt method on the RT$^2$ Profiler PCR Array Data Analysis Web Portal. All Ct values >35 or non amplified were changed to the cut-off value of 35. The housekeeping genes used for normalization are GAPDH and RPLP0. The control group is TGF-β1 treated cells.

As illustrated in FIG. 1, Compound I increases the expression of HGF, growth factor associated with tissue repair, regeneration and anti-aging. The following Table 2 shows that HGF expression in NHDF cells (Untreated) is reduced by TGF-β1 which is corrected or increased with representative Compounds of formula I disclosed herein (Compound #).

TABLE 2

| Cells | Compound Concentration (μM) | HGF Relative Quantitation |
|---|---|---|
| Untreated | — | 7.23 |
| TGF-β1 | — | 1.00 |
| TGF-β1 + Compound I | 500 | 4.23 |
| TGF-β1 + Compound XVIII | 25 | 1.40 |
| TGF-β1 + Compound XXXIII | 6 | 1.54 |
| TGF-β1 + Compound XXXII | 10 | 1.73 |
| TGF-β1 + Compound IV | 500 | 3.80 |
| TGF-β1 + Compound III | 500 | 2.41 |
| TGF-β1 + Compound II | 250 | 1.37 |
| TGF-β1 + Compound XII | 500 | 2.47 |
| TGF-β1 + Compound V | 100 | 2.73 |
| TGF-β1 + Compound VI | 100 | 2.77 |
| TGF-β1 + Compound XIII | 500 | 1.71 |
| TGF-β1 + Compound VII | 500 | 2.66 |

TABLE 2-continued

| Cells | Compound Concentration (μM) | HGF Relative Quantitation |
|---|---|---|
| TGF-β1 + Compound VIII | 500 | 1.44 |
| TGF-β1 + Compound XI | 250 | 3.38 |
| TGF-β1 + Compound X | 250 | 3.06 |

Figure 2:
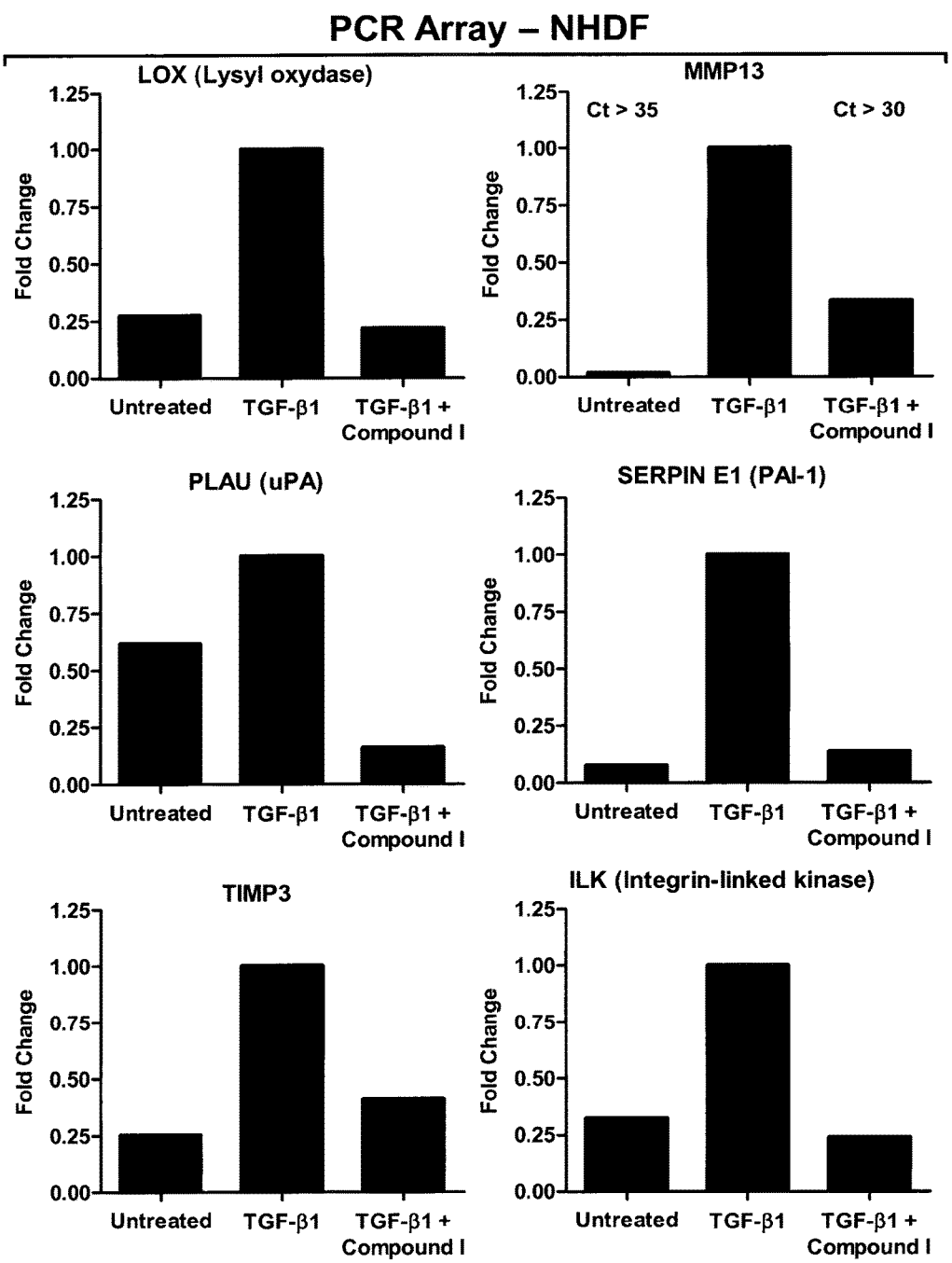
FIG. 2 is an illustration of the effect of Compound I on the modulation of regeneration markers expressed in injured fibroblast (NHDF) involved in self-repair and regeneration of tissue.
Figure 3:
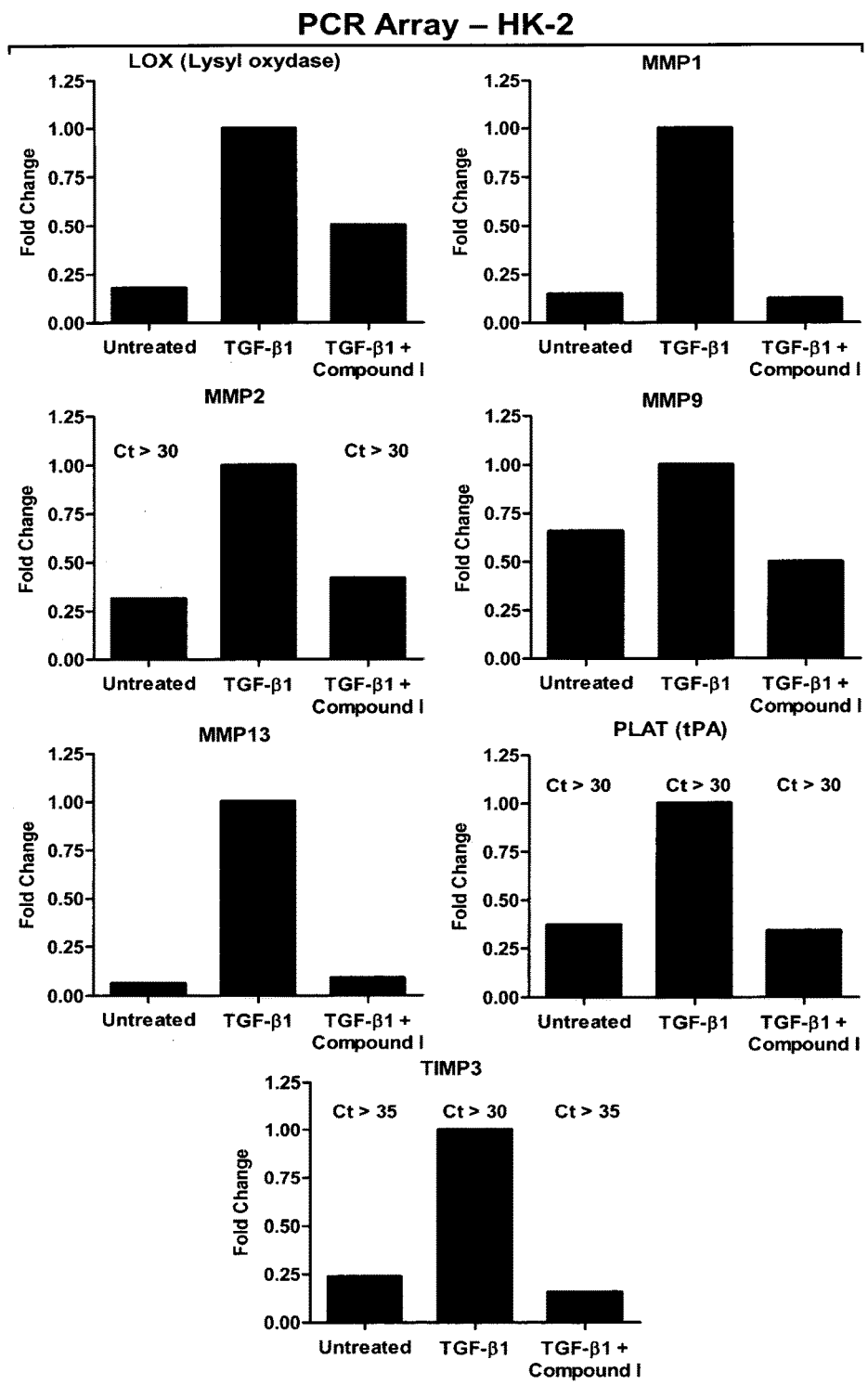
FIG. 3 is an illustration of the effect of Compound I on the modulation of regeneration markers expressed in injured epithelial cells (HK-2) involved in self-repair and regeneration of tissue.

An experiment was undertaken to determine the effect of compounds on the expression of regeneration markers. This experiment was performed with NHDF (Normal Human Dermal Fibroblasts) and human epithelial cells (renal tubular epithelial cells, HK-2) involved in tissue regeneration after single, multiple or constant injury. Injury was simulated by incubation of the cells with TGF-β1. NHDF was used as previously described and HK-2 human epithelial proximal tubule cells (ATCC #CRL-2190) were starved overnight in DMEM/F12+0.2% FBS and treated with or without rhTGF-β1 (10 ng/ml) and compound I (500 μM) for 24 h. Results indicated that compound I brings the expression level of the regeneration markers at a normal control level indicating a self-repair mechanism of the injured cells. In NHDF (FIG. 2), LOX, MMP13, PLAU (uPA), serpin E1, TIMP3 and ILK are all expressed at a normal level, additionally in HK-2 cells (FIG. 3), LOX, MMP1, MMP2, MMP9, MMP13, TIMP3 and PLAT (tPA) are also all expressed at a level close to the normal level observed in healthy cells.

Example 3

Figure 4:
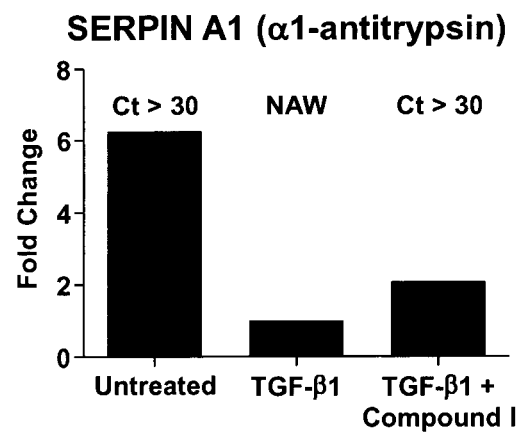
FIG. 4 demonstrates that Compound I can increase mRNA expression of Serpin A1 (AAT) involved in nerve generation.
Figure 5:
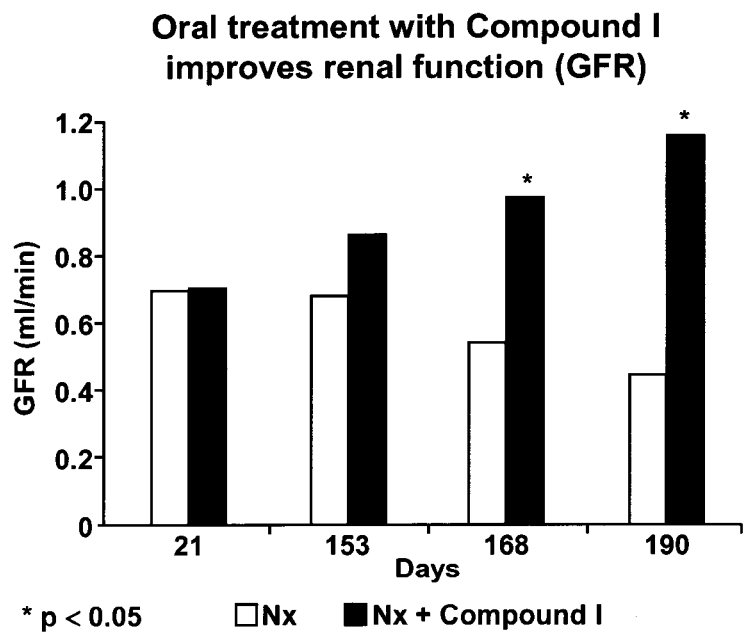
FIG. 5 is a representation of the increase in organ function (GFR) observed with Compound I and indicating tissue regeneration of an injured kidney.

Effect of Compound I on Endogenous Production of AAT and Regeneration of Nerve Tissue As mentioned above, AAT can induce nerve regeneration. Through a qPCR-panel on NHDF (method described in Example 2), Compound I has demonstrated an ability to increase AAT mRNA expression (FIG. 4) in injured cells, indicating that Compound I can increase nerve regeneration or other injured tissues. Compound I is representative of the compounds of formula I disclosed herein. Therefore, the compounds of formula I disclosed herein may increase regeneration of nerves via the production of endogenous AAT at the site of injury.

* * *

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for tissue regeneration of an organ or for stimulating the generation of tissue growth in a subject in need of tissue regeneration, wherein the subject is not in need of a treatment of fibrosis, the method comprising administering to the subject a compound represented by Formula I or a pharmaceutically acceptable salt thereof, or a combination thereof:

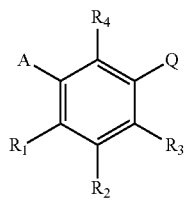

Formula I wherein
A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_1$ is H, F or OH;
$R_2$ is H, F OH, $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_3$ is H, F, OH or $CH_2Ph$;
$R_4$ is H, F or OH;
Q is
  1) $(CH_2)_mC(O)OH$ wherein m is 1 or 2,
  2) $CH(CH_3)C(O)OH$,
  3) $C(CH_3)_2C(O)OH$,
  4) CH(F)—C(O)OH,
  5) $CF_2$—C(O)OH, or
  6) C(O)—C(O)OH; and
wherein the organ that is regenerated or the tissue that is stimulated to grow is selected from the group consisting of heart, liver, lung, skin, stomach, intestine, muscle or cartilage.

2. The method of claim 1, wherein A is $C_5$ alkyl or $C_6$ alkyl.

3. The method of claim 1, wherein $R_2$ is H, F, OH, $C_5$ alkyl or $C_6$ alkyl.

4. The method of claim 1, wherein $R_3$ is H, OH or $CH_2Ph$.

5. The method of claim 1, wherein Q is $(CH_2)_mC(O)OH$ where m is 1 or 2.

6. The method of claim 1, wherein A is $C_5$ alkyl or $C_6$ alkyl; $R_1$ is H, F or OH; $R_2$ is H, F, OH, $C_5$ alkyl or $C_6$ alkyl; $R_3$ is H, OH or $CH_2Ph$; $R_4$ is H, F or OH; and Q is $(CH_2)_mC(O)OH$ where m is 1 or 2.

7. The method of claim 1, wherein A is $C_5$ alkyl; $R_1$ is H; $R_2$ is H or $C_5$ alkyl; $R_3$ is H; $R_4$ is H; and Q is $(CH_2)_mC(O)$OH where m is 1.

8. The method of claim 1, wherein said compound is selected from the group consisting of the compounds represented by the following structures:

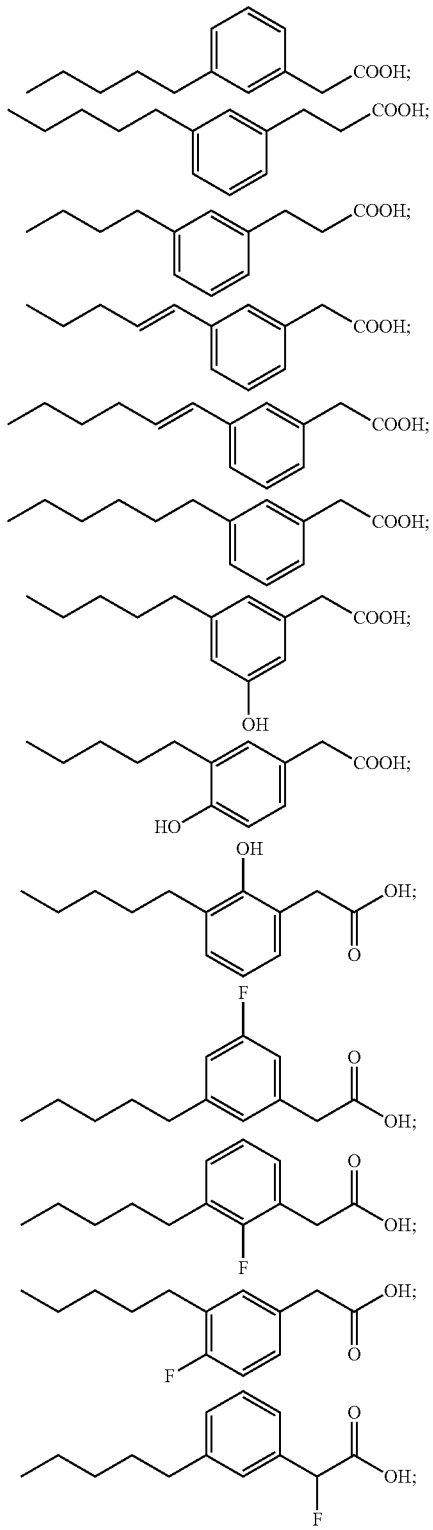

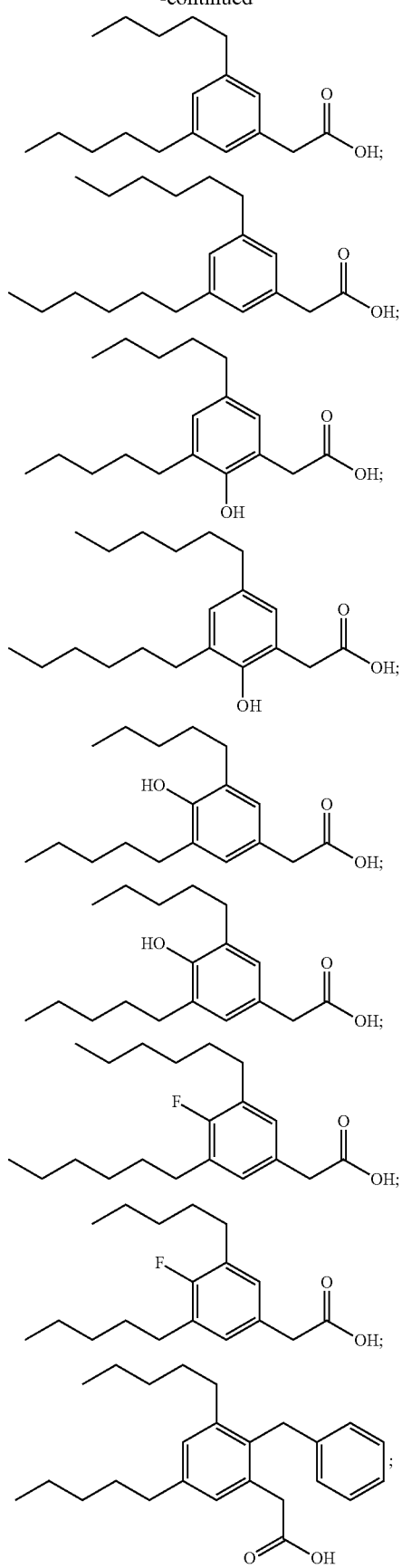
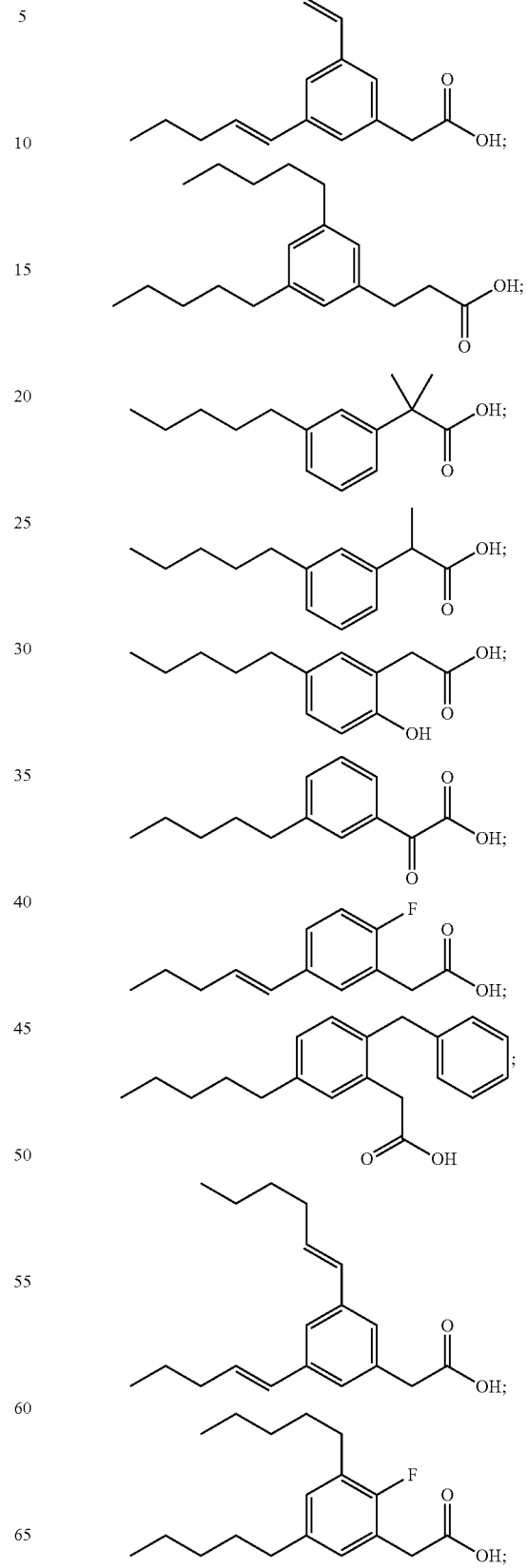

-continued

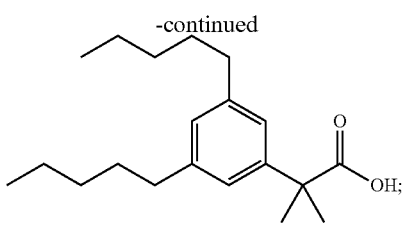

and pharmaceutically acceptable salts thereof.

9. The method of claim 1, wherein said compound is represented by the following structure:

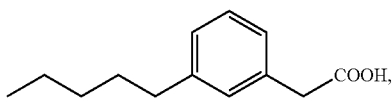

or pharmaceutically acceptable salt thereof.

10. The method of claim 1, wherein said compound is represented by the following structure:

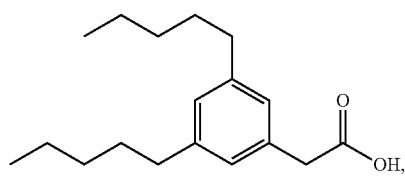 [SMILES: CCCCCc1cc(CCCCC)cc(CC(=O)O)c1]

or pharmaceutically acceptable salt thereof.

11. The method of claim 1, wherein the pharmaceutically acceptable salt is a base addition salt comprising a metal counterion selected from the group consisting of sodium, potassium, calcium, magnesium, lithium, ammonium, manganese, zinc, iron, or copper.

12. The method of claim 1, wherein the pharmaceutically acceptable salt is a sodium salt.

13. The method of claim 1, wherein the organ is an injured organ.

14. A method for modulating the expression of a tissue self-repair marker or a tissue regeneration marker in a cell or an organ of a subject, wherein the cell or organ is not fibrotic and the cell or organ is selected from the group consisting of heart, liver, lung, skin, stomach, intestine, muscle and cartilage, the method comprising the step of administering to a subject in need of tissue regeneration a compound represented by Formula I or a pharmaceutically acceptable salt thereof, or a combination thereof:

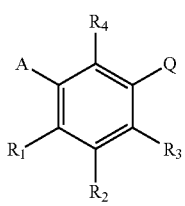

Formula I wherein
A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4;
$R_1$ is H, F or OH;
$R_2$ is H, F, OH, $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4;
$R_3$ is H, F, OH or $CH_2Ph$;
$R_4$ is H, F or OH;
Q is
1) $(CH_2)_m C(O)OH$ wherein m is 1 or 2,
2) $CH(CH_3)C(O)OH$,
3) $C(CH_3)_2 C(O)OH$,
4) $CH(F)$—$C(O)OH$,
5) $CF_2$—$C(O)OH$, or
6) $C(O)$—$C(O)OH$; and
wherein the tissue self-repair marker or the tissue regeneration marker is expressed in the heart, liver, lung, skin, stomach, intestine, muscle or cartilage.

15. The method of claim 14, wherein the marker is a metalloproteinase or a growth factor.

16. The method of claim 14, wherein the marker is hepatocyte growth factor (HGF) or Serpin A1 (AAT).

17. A method for treating a physical injury in an organ or tissue in a subject in need of tissue regeneration, wherein the organ or tissue is not fibrotic and is selected from the group consisting of heart, liver, lung, skin, stomach, intestine, muscle and cartilage, the method comprising contacting the organ or tissue with an effective amount of a compound represented by Formula I or a pharmaceutically acceptable salt thereof, or a combination thereof:

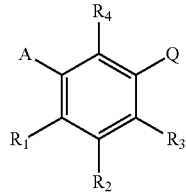

Formula I wherein
A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4;
$R_1$ is H, F or OH;
$R_2$ is H, F, OH, $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4;
$R_3$ is H, F, OH or $CH_2Ph$;
$R_4$ is H, F or OH;
Q is
1) $(CH_2)_m C(O)OH$ wherein m is 1 or 2,
2) $CH(CH_3)C(O)OH$,
3) $C(CH_3)_2 C(O)OH$,
4) $CH(F)$—$C(O)OH$,
5) $CF_2$—$C(O)OH$, or
6) $C(O)$—$C(O)OH$; and
wherein said contacting treats the physical injury to the heart, liver, lung, skin, stomach, intestine, muscle or cartilage.

18. The method of claim 17, wherein the physical injury comprises a wound and said treating comprises promoting wound healing.

19. A method for treating aging of skin in a subject in need of an anti-aging treatment due to UV exposure, climatic conditions exposure, pollution exposure, alcohol consumption or smoking, the method comprising administering to the skin of the subject an effective amount of a compound represented by Formula I or a pharmaceutically acceptable salt thereof, or a combination thereof:

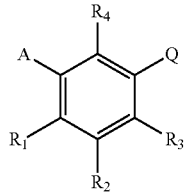

Formula I wherein
A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_1$ is H, F or OH;
$R_2$ is H, F, OH, $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_3$ is H, F, OH or $CH_2Ph$;
$R_4$ is H, F or OH;
Q is
1) $(CH_2)_m C(O)OH$ wherein m is 1 or 2,
2) $CH(CH_3)C(O)OH$,
3) $C(CH_3)_2 C(O)OH$,
4) CH(F)—C(O)OH,
5) $CF_2$—C(O)OH, or
6) C(O)—C(O)OH.

\* \* \* \* \*

UNITED STATES PATENT AND TRADEMARK OFFICE
CERTIFICATE OF CORRECTION

PATENT NO.         : 10,391,073 B2
APPLICATION NO.    : 15/526405
DATED              : August 27, 2019
INVENTOR(S)        : Lyne Gagnon and Pierre Laurin Page 1 of 1

It is certified that error appears in the above-identified patent and that said Letters Patent is hereby corrected as shown below:

In the Claims

Column 55 at Line 41, delete "F OH" and insert -- F, OH --; and

Column 58 at Line 55 (second structure from bottom), delete " 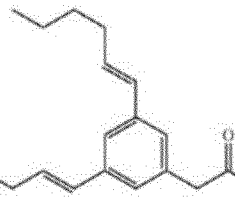 " and insert -- [structure] --.

Signed and Sealed this
Twelfth Day of November, 2019

Andrei Iancu
*Director of the United States Patent and Trademark Office*